United States Patent
Jørgensen et al.

(10) Patent No.: US 6,808,896 B2
(45) Date of Patent: Oct. 26, 2004

(54) METHOD FOR STABLE CHROMOSOMAL MULTI-COPY INTEGRATION OF GENES

(75) Inventors: Steen Troels Jørgensen, Allerød (DK); Jens Toenne Andersen, Nærum (DK); Michael Dolbjerg Rasmussen, Vallensbæk (DK); Carsten Olsen, Bagsværd (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 09/928,847

(22) Filed: Aug. 13, 2001

(65) Prior Publication Data

US 2003/0032186 A1 Feb. 13, 2003

Related U.S. Application Data

(63) Continuation of application No. PCT/DK01/00436, filed on Jun. 21, 2001.
(60) Provisional application No. 60/217,929, filed on Jul. 13, 2000.

(30) Foreign Application Priority Data

Jun. 23, 2000 (DK) .......................... 2000 00981

(51) Int. Cl.$^7$ .............................. C12P 21/00; C12N 1/00
(52) U.S. Cl. ................. 435/69.1; 435/41; 435/71.1; 435/71.2; 435/440; 435/471; 435/476; 435/477; 435/320.1; 435/243; 435/252.1; 435/252.3; 435/252.31; 435/252.5

(58) Field of Search .................. 435/41, 69.1, 71.1, 435/71.2, 440, 471, 476, 477, 479, 481, 485, 320.1, 243, 252.1, 252.3, 252.31, 252.5; 536/22.1, 23.1, 24.1

(56) References Cited

U.S. PATENT DOCUMENTS

2003/0044940 A1 * 3/2003 Rasmussen ................ 435/91.2

FOREIGN PATENT DOCUMENTS

| EP | 0 185 512 | 6/1986 |
| EP | 0 972 838 | 1/2000 |
| WO | WO 91/09129 | 6/1991 |
| WO | WO 94/14968 | 7/1994 |
| WO | WO 99/32641 * | 7/1999 |
| WO | WO 99/41358 | 8/1999 |

OTHER PUBLICATIONS

Hone et al., Microbial Pathogenesis 1988; 5: 407–418.

* cited by examiner

*Primary Examiner*—James Ketter
*Assistant Examiner*—David Lambertson
(74) *Attorney, Agent, or Firm*—Elias J. Lambiris

(57) ABSTRACT

The present invention solves the problem of integrating multiple copies of a gene of interest by homologous recombination into well defined positions adjacent to conditionally essential genes in a bacterial host strain chromosome, which already comprises at least one copy of the gene of interest in a different position.

21 Claims, 3 Drawing Sheets

METHOD FOR STABLE CHROMOSOMAL MULTI-COPY INTEGRATION OF GENES

CROSS-REFERENCE TO RELATED APPLICATIONS

Figure 1:
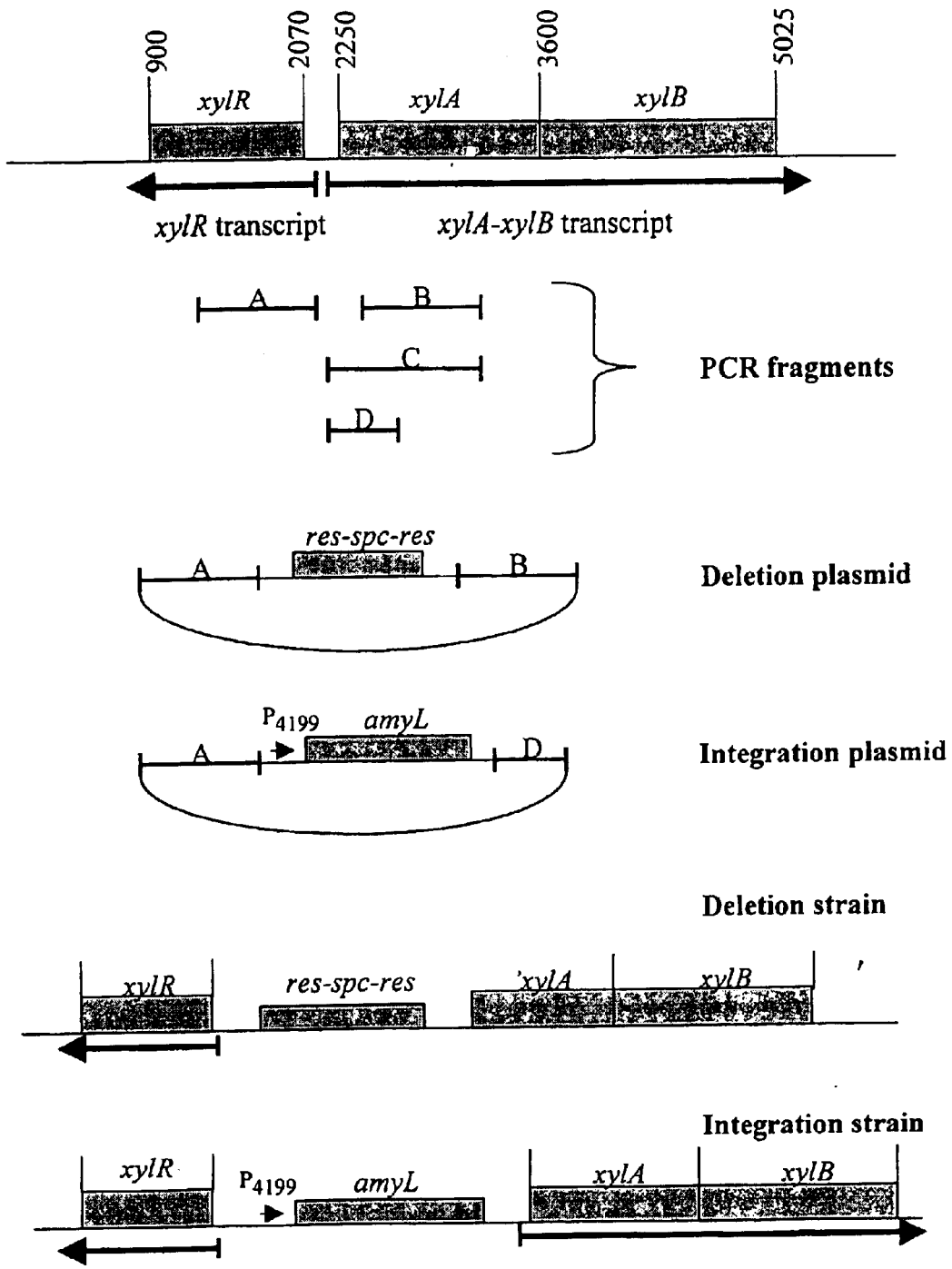

This application is a continuation of PCT/DK01/00436 filed Jun. 21, 2001 (the international application was published under PCT Article 21(2) in English) and claims, under 35 U.S.C. 119, priority or the benefit of Danish application no. PA 2000 00981 filed Jun. 23, 2000 and U.S. provisional application No. 60/217,929 filed Jul. 13, 2000, the contents of which are fully incorporated herein by reference.

FIELD OF THE INVENTION

The invention relates to a method for inserting genes into the chromosome of bacterial strains, and the resulting strains. In the biotech industry it is desirable to construct polypeptide production strains having several copies of a gene of interest stably chromosomally integrated, without leaving antibiotic resistance marker genes in the strains.

BACKGROUND OF THE INVENTION

In the industrial production of polypeptides it is of interest to achieve a product yield as high as possible. One way to increase the yield is to increase the copy number of a gene encoding a polypeptide of interest. This can be done by placing the gene on a high copy number plasmid, however plasmids are unstable and are often lost from the host cells if there is no selective pressure during the cultivation of the host cells. Another way to increase the copy number of the gene of interest is to integrate it into the host cell chromosome in multiple copies. It has previously been described how to integrate a gene into the chromosome by double homologous recombination without using antibiotic markers (Hone et al., Microbial Pathogenesis, 1988, 5: 407–418); integration of two genes has also been described (Novo Nordisk: WO 91/09129 and WO 94/14968). A problem with integrating several copies of a gene into the chromosome of a host cell is instability. Due to the sequence identity of the copies there is a high tendency for the them to recombine out of the chromosome again during cultivation of the host cell unless a selective marker or other essential DNA is included between the copies and selective pressure is applied during cultivation, especially if the genes are located in relative close vicinity of each other. It has been described how to integrate two genes closely spaced in anti-parallel tandem to achieve better stability (Novo Nordisk: WO 99/41358).

The present day public debate concerning the industrial use of recombinant DNA technology has raised some questions and concern about the use of antibiotic marker genes. Antibiotic marker genes are traditionally used as a means to select for strains carrying multiple copies of both the marker genes and an accompanying expression cassette coding for a polypeptide of industrial interest. In order to comply with the current demand for recombinant production host strains devoid of antibiotic markers, we have looked for possible alternatives to the present technology that will allow substitution of the antibiotic markers we use today with non-antibiotic marker genes. Thus in order to provide recombinant production strains devoid of antibiotic resistance markers, it remains of industrial interest to find new methods to stably integrate genes in multiple copies into host cell chromosomes.

SUMMARY OF THE INVENTION

The present invention solves the problem of integrating multiple copies of a gene of interest by homologous recombination into well defined chromosomal positions of a bacterial host strain which already comprises at least one copy of the gene of interest in a different position. This can be done by making a deletion of part of one or more conditionally essential gene(s) (hereafter called the "integration gene") in the host chromosome of a strain which already comprises at least one copy of a gene of interest, or by otherwise altering the gene(s) to render it non-functional; or by integrating at least one partial non-functional conditionally essential gene into the host chromosome, so that the resulting strain has a deficiency (e.g. specific carbon-source utilization) or a growth requirement (e.g. amino acid auxotrophy) or is sensitive to a given stress. The next (i.e. second or third etc.) copy of the gene of interest is then introduced on a vector, on which the gene is flanked upstream by a partial fragment of the integration gene, and downstream is flanked by a fragment homologous to a DNA sequence downstream of the integration gene on the host chromosome. Thus, neither host chromosome nor the incoming vector contain a full version of the integration gene. In a non-limiting example the host chromosome may comprise the first two thirds of the integration gene and the vector the last two thirds, effectively establishing a sequence overlap of one third of the integration gene on the vector and the chromosome.

Expression of the full version of the integration gene will only occur if homologous recombination between vector and host chromosome takes place via the partial integration gene sequences, and this particular recombination event can be efficiently selected for, even against the background of homologous integration into the chromosome directed by the gene of interest into the identical gene(s) comprised on the chromosome already.

This strategy will enable directed gene integration by homologous recombination at predetermined loci, even though extended homology exists between the gene of interest on the incoming vector and other copies of this gene at other locations in the chromosome, and even though it is not feasible to identify the desired integrants based on the qualitative phenotype resulting from expression of the gene of interest, as this gene is already present in one or more copies in the host.

In a non-limiting example herein a *Bacillus* enzyme production strain is provided that comprises two anti-parallel copies (inverted orientation) of a gene encoding the commercially available amylase Termamyl® (Novo Nordisk, Denmark). A gene homologous to the dal gene of *Bacillus subtilis*, encoding a D-alanine racemase, was identified in the *Bacillus* production strain, it was sequenced and a partial deletion was made in the dal gene of the *Bacillus* two-copy Termamyl® strain. A vector was constructed to effect a stable non-tandem chromosomal insertion of a third Termamyl® gene copy adjacent to the dal locus, in the process effectively restoring the complete dal gene, according to the above strategy.

In another non-limiting example herein, an additional copy of the amylase encoding gene was introduced into the xylose isomerase operon of the *Bacillus* enzyme production strain which already comprised at least two copies of the amylase gene located elsewhere on the chromosome.

Also in a non-limiting example we demonstrate the method of the invention by integrating an additional amylase-encoding gene into the gluconat operon of the *Bacillus* enzyme production strain. Other non-limiting examples of integration into conditionally essential genes are given below.

Accordingly in a first aspect the invention relates to a method for constructing a cell comprising at least two copies of a gene of interest stably integrated into the chromosome in different positions, the method comprising the steps of:
- a) providing a host cell comprising at least one chromosomal copy of the gene of interest, and comprising one or more conditionally essential chromosomal gene(s) which has been altered to render the gene(s) non-functional;
- b) providing a DNA construct comprising:
  - i) an altered non-functional copy of the conditionally essential gene(s) of step a); and
  - ii) at least one copy of the gene of interest flanked on one side by i) and on the other side by a DNA fragment homologous to a host cell DNA sequence located on the host cell chromosome adjacent to the gene(s) of step a); wherein a first recombination between the altered copy of i) and the altered chromomosomal gene(s) of step a) restores the conditionally essential chromosomal gene(s) to functionality and renders the cell selectable;
- c) introducing the DNA construct into the host cell and cultivating the cell under selective conditions that require a functional conditionally essential gene(s); and
- d) selecting a host cell that grows under the selective conditions of the previous step; wherein the at least one copy of the gene of interest has integrated into the host cell chromosome adjacent to the gene(s) of step a); and optionally
- e) repeating steps a) to d) at least once using a different chromosomal gene(s) in step a) in each repeat.

Another way of describing the first aspect of the invention relates to a method for constructing a cell comprising at least two copies of a gene of interest stably integrated into the chromosome in different positions, the method comprising the steps of:
- a) providing a host cell comprising at least one chromosomal copy of the gene of interest;
- b) altering a conditionally essential chromosomal gene(s) of the host cell whereby the gene becomes non-functional;
- c) making a DNA construct comprising:
  - i) an altered non-functional copy of the chromosomal gene(s) of step b); and
  - ii) at least one copy of the gene of interest flanked on one side by i) and on the other side by a DNA fragment homologous to a host cell DNA sequence adjacent to the gene(s) of step b); wherein a first recombination between the altered copy of i) and the altered chromomosomal gene(s) of step b) restores the chromosomal gene(s) to functionality and renders the cell selectable;
- d) introducing the DNA construct into the host cell and cultivating the cell under selective conditions that require a functional gene(s) of step b); and
- e) selecting a host cell that grows under the selective conditions of step d); wherein the at least one copy of the gene of interest has integrated into the host cell chromosome adjacent to the gene(s) of step b); and optionally
- f) repeating steps a) to e) at least once using a different chromosomal gene(s) in step b) in each repeat.

Herein genetic tools are also described in the form of DNA constructs necessary for carrying out the method of the invention.

Consequently in a second aspect the invention relates to a DNA construct comprising:
- i) an altered non-functional copy of a conditionally essential chromosomal gene(s) from a host cell, preferably the copy is partially deleted; and
- ii) at least one copy of a gene of interest flanked on one side by i) and on the other side by a DNA fragment homologous to a host cell DNA sequence located on the host cell chromosome adjacent to the conditionally essential gene(s) of i).

The present invention provides a method for obtaining a host cell comprising at least two copies of a gene of interest stably integrated on the chromosome adjacent to conditionally essential loci.

Accordingly in a third aspect the invention relates to a host cell comprising at least two copies of a gene of interest stably integrated into the chromosome, where at least one copy is integrated adjacent to a conditionally essential locus and wherein the cell is obtainable by any of the methods defined in the first aspects.

Another way of describing an aspect of the invention relates to a host cell comprising at least two copies of a gene of interest stably integrated into the chromosome, where each copy is integrated adjacent to different conditionally essential loci and wherein the cell is obtainable by any of the methods defined in the first aspects.

The method of the invention relies on complementing a conditionally essential gene(s) that was rendered non-functional, and a number of suitable host cells comprising such non-functional genes are described herein. To carry out multiple rounds of gene integration according to the invention it is advantageous to provide a host cell comprising several non-functional conditionally essential genes.

In a fourth aspect the invention relates to a *Bacillus licheniformis* cell, wherein at least two conditionally essential genes are rendered non-functional, preferably the genes are chosen from the group consisting of xylA, galE, gntK, gntP, glpP, glpF, glpK, glpD, araA, metC, lysA, and dal.

Any host cell as described herein for use in a method of the invention is intended to be encompassed by the scope of the invention.

Another aspect of the invention relates to the use of a cell as defined in the previous aspect in a method as defined in the first aspects.

As mentioned above, genetic tools of the invention are described herein, and it is intended that the scope of the invention comprises such constructs when present in or propagated in host cells as is common in the art.

Yet another aspect of the invention relates to a cell comprising a DNA construct as defined in the second aspect.

In a final aspect the invention relates to a process for producing an enzyme of interest, comprising cultivating a cell as defined in any of the preceding aspects under conditions appropriate for producing the enzyme, and optionally purifying the enzyme.

FIGURES

FIG. 1: Schematic representation of the *B. licheniformis* xylose isomerase region, PCR fragments, Deletion and Integration plasmids and strains.

Figure 2:
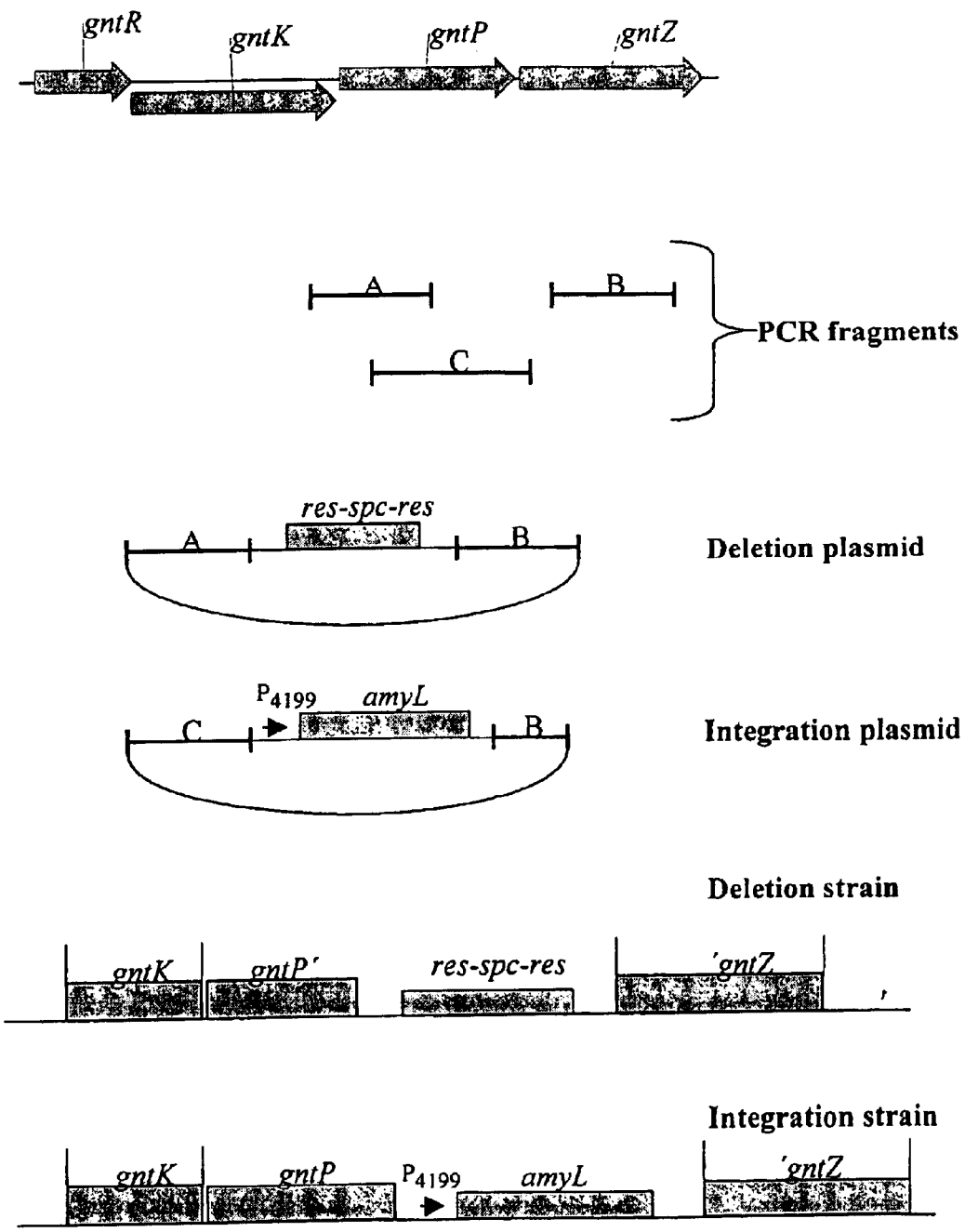

FIG. 2: Schematic representation of the *B. licheniformis* gluconat region, PCR fragments, Deletion and Integration plasmids and strains.

Figure 3:
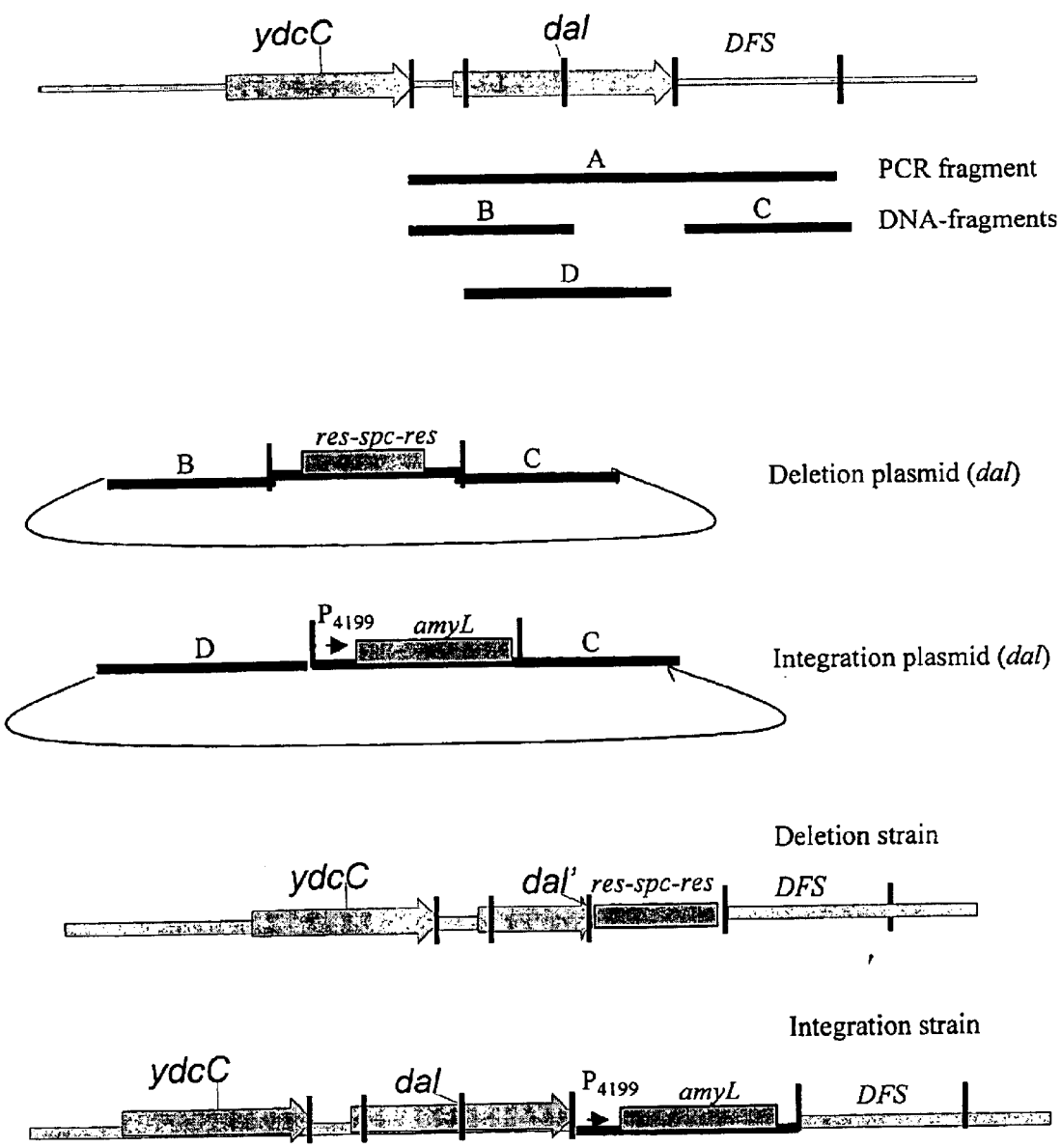

FIG. 3: Schematic representation of the *B. licheniformis* D-alanine racemase encoding region, PCR fragments, Deletion and Integration plasmids and strains.

DEFINITIONS

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989") *DNA Cloning: A Practical Approach*, Volumes I and II/D. N. Glover ed. 1985); *Oligonucleotide Synthesis* (M. J. Gait ed. 1984); *Nucleic Acid Hybridization* (B. D. Hames & S. J. Higgins eds (1985)); *Transcription And Translation* (B. D. Hames & S. J. Higgins, eds. (1984)); *Animal Cell Culture* (R. I. Freshney, ed. (1986)); *Immobilized Cells And Enzymes* (IRL Press, (1986)); B. Perbal, *A Practical Guide To Molecular Cloning* (1984).

A "polynucleotide" is a single- or double-stranded polymer of deoxyribonucleotide or ribonucleotide bases, the sequence of the polynucleotide is the actual sequence of the bases read from the 5' to the 3' end of the polymer. Polynucleotides include RNA and DNA, and may be isolated from natural sources, synthesized in vitro, or prepared from a combination of natural and synthetic molecules.

A "nucleic acid molecule" or "nucleotide sequence" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules") in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary or quaternary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A DNA "coding sequence" or an "open reading frame (ORF)" is a double-stranded DNA sequence which is transcribed and translated into a polypeptide in a cell in vitro or in vivo when placed under the control of appropriate regulatory sequences. The ORF "encodes" the polypeptide. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

An expression vector is a DNA molecule, linear or circular, that comprises a segment encoding a polypeptide of interest operably linked to additional segments that provide for its transcription. Such additional segments may include promoter and terminator sequences, and optionally one or more origins of replication, one or more selectable markers, an enhancer, a polyadenylation signal, and the like. Expression vectors are generally derived from plasmid or viral DNA, or may contain elements of both.

Transcriptional and translational control sequences are DNA regulatory sequences, such as promoters, enhancers, terminators, and the like, that provide for the expression of a coding sequence in a host cell e.g. in eukaryotic cells, polyadenylation signals are control sequences.

A "secretory signal sequence" is a DNA sequence that encodes a polypeptide (a "secretory peptide" that, as a component of a larger polypeptide, directs the larger polypeptide through a secretory pathway of a cell in which it is synthesized. The larger polypeptide is commonly cleaved to remove the secretory peptide during transit through the secretory pathway.

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A chromosomal gene is rendered "non-functional" if the polypeptide that the gene encodes can no longer be expressed in a functional form. Such non-functionality of a gene can be induced by a wide variety of genetic manipulations or alterations as known in the art, some of which are described in Sambrook et al. vide supra. Partial deletions within the ORF of a gene will often render the gene non-functional, as will mutations e.g. substitutions, insertions, frameshifts etc.

"Operably linked", when referring to DNA segments, indicates that the segments are arranged so that they function in concert e.g. the transcription process takes place via the RNA-polymerase binding to the promoter segment and proceeding with the transcription through the coding segment until the polymerase stops when it encounters a transcription terminator segment.

"Heterologous" DNA in a host cell, in the present context refers to exogenous DNA not originating from the cell.

As used herein the term "nucleic acid construct" is intended to indicate any nucleic acid molecule of cDNA, genomic DNA, synthetic DNA or RNA origin. The term "construct" is intended to indicate a nucleic acid segment which may be single- or double-stranded, and which may be based on a complete or partial naturally occurring nucleotide sequence encoding a polypeptide of interest. The construct may optionally contain other nucleic acid segments.

The nucleic acid construct of the invention encoding the polypeptide of the invention may suitably be of genomic or cDNA origin, for instance obtained by preparing a genomic or cDNA library and screening for DNA sequences coding for all or part of the polypeptide by hybridization using synthetic oligonucleotide probes in accordance with standard techniques (cf. Sambrook et al., supra).

The nucleic acid construct of the invention encoding the polypeptide may also be prepared synthetically by established standard methods, e.g. the phosphoamidite method described by Beaucage and Caruthers, Tetrahedron Letters 22 (1981), 1859–1869, or the method described by Matthes et al., EMBO Journal 3 (1984), 801–805. According to the phosphoamidite method, oligonucleotides are synthesized, e.g. in an automatic DNA synthesizer, purified, annealed, ligated and cloned in suitable vectors.

Furthermore, the nucleic acid construct may be of mixed synthetic and genomic, mixed synthetic and cDNA or mixed genomic and cDNA origin prepared by ligating fragments of synthetic, genomic or cDNA origin (as appropriate), the fragments corresponding to various parts of the entire nucleic acid construct, in accordance with standard techniques. The nucleic acid construct may also be prepared by polymerase chain reaction using specific primers, for instance as described in U.S. Pat. No. 4,683,202 or Saiki et al., Science 239 (1988), 487–491.

The term nucleic acid construct may be synonymous with the term "expression cassette" when the nucleic acid construct contains the control sequences necessary for expression of a coding sequence of the present invention.

The term "control sequences" is defined herein to include all components that are necessary or advantageous for expression of the coding sequence of the nucleic acid sequence. Each control sequence may be native or foreign to the nucleic acid sequence encoding the polypeptide. Such control sequences include, but are not limited to, a leader, a polyadenylation sequence, a propeptide sequence, a promoter, a signal sequence, and a transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide.

The control sequence may be an appropriate promoter sequence, a nucleic acid sequence that is recognized by a host cell for expression of the nucleic acid sequence. The promoter sequence contains transcription and translation control sequences that mediate the expression of the polypeptide. The promoter may be any nucleic acid sequence that shows transcriptional activity in the host cell of choice and may be obtained from genes encoding extracellular or intracellular polypeptides either homologous or heterologous to the host cell.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

The control sequence may also be a polyadenylation sequence, a sequence which is operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention.

The control sequence may also be a signal peptide-coding region, which codes for an amino acid sequence linked to the amino terminus of the polypeptide which can direct the expressed polypeptide into the cell's secretory pathway of the host cell. The 5' end of the coding sequence of the nucleic acid sequence may inherently contain a signal peptide-coding region naturally linked in translation reading frame with the segment of the coding region which encodes the secreted polypeptide. Alternatively, the 5' end of the coding sequence may contain a signal peptide-coding region which is foreign to that portion of the coding sequence which encodes the secreted polypeptide. A foreign signal peptide-coding region may be required where the coding sequence does not normally contain a signal peptide-coding region. Alternatively, the foreign signal peptide coding region may simply replace the natural signal peptide coding region in order to obtain enhanced secretion of the polypeptide relative to the natural signal peptide coding region normally associated with the coding sequence. The signal peptide-coding region may be obtained from a glucoamylase or an amylase gene from an *Aspergillus* species, a lipase or proteinase gene from a *Rhizomucor* species, the gene for the alpha-factor from *Saccharomyces cerevisiae*, an amylase or a protease gene from a *Bacillus* species, or the calf prepro-chymosin gene. However, any signal peptide coding region capable of directing the expressed polypeptide into the secretory pathway of a host cell of choice may be used in the present invention.

The control sequence may also be a propeptide coding region, which codes for an amino acid sequence positioned at the amino terminus of a polypeptide. The resultant polypeptide is known as a proenzyme or propolypeptide (or a zymogen in some cases). A propolypeptide is generally inactive and can be converted to mature active polypeptide by catalytic or autocatalytic cleavage of the propeptide from the propolypeptide. The propeptide coding region may be obtained from the *Bacillus subtilis* alkaline protease gene (aprE), the *Bacillus subtilis* neutral protease gene (nprT), the *Saccharomyces cerevisiae* alpha-factor gene, or the *Myceliophthora thermophilum* laccase gene (WO 95/33836).

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems would include the lac, tac, and trp operator systems. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be placed in tandem with the regulatory sequence.

Examples of suitable promoters for directing the transcription of the nucleic acid constructs of the present invention, especially in a bacterial host cell, are the promoters obtained from the *E. coli* lac operon, the *Streptomyces coelicolor* agarase gene (dagA), the *Bacillus subtilis* levansucrase gene (sacB), the *Bacillus subtilis* alkaline protease gene, the *Bacillus licheniformis* alpha-amylase gene (amyL), the *Bacillus stearothermophilus* maltogenic amylase gene (amyM), the *Bacillus amyloliquefaciens* alpha-amylase gene (amyQ), the *Bacillus amyloliquefaciens* BAN AMYLASE GENE, the *Bacillus licheniformis* penicillinase gene (penP), the *Bacillus subtilis* xylA and xylB genes, and the prokaryotic beta-lactamase gene (Villa-Kamaroff et al., 1978, *Proceedings of the National Academy of Sciences USA* 75:3727–3731), as well as the tac promoter (DeBoer et al., 1983, *Proceedings of the National Academy of Sciences USA* 80:21–25). Further promoters are described in "Useful proteins from recombinant bacteria" in *Scientific American*, 1980, 242:74–94; and in Sambrook et al., 1989, supra.

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression, and possibly secretion.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids. The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. The vector system may be a single vector or plasmid or two or more vectors or plasmids which together contain the total DNA to be introduced into the genome of the host cell, or a transposon.

The vectors of the present invention preferably contain one or more "selectable markers" which permit easy selection of transformed cells. A selectable marker is a gene the product of which provides for biocide, antibiotic or viral resistance, resistance to heavy metals, prototrophy to auxotrophs, and the like.

A "conditionally essential gene" may function as a "non-antibiotic selectable marker". Non-limiting examples of bacterial conditionally essential selectable markers are the dal genes from *Bacillus subtilis* or *Bacillus licheniformis*, that are only essential when the bacterium is cultivated in the absence of D-alanine. Also the genes encoding enzymes involved in the turnover of UDP-galactose can function as conditionally essential markers in a cell when the cell is grown in the presence of galactose or grown in a medium which gives rise to the presence of galactose. Non-limiting examples of such genes are those from *B. subtilis* or *B. licheniformis* encoding UTP-dependent phosphorylase (EC 2.7.7.10), UDP-glucose-dependent uridylyltransferase (EC 2.7.7.12), or UDP-galactose epimerase (EC 5.1.3.2). Also a xylose isomerase gene such as xylA, of Bacilli can be used as selectable markers in cells grown in minimal medium with xylose as sole carbon source. The genes necessary for utilizing gluconate, gntK, and gntP can also be used as selectable markers in cells grown in minimal medium with gluconate as sole carbon source. Other non-limiting examples of conditionally essential genes are given below.

Antibiotic selectable markers confer antibiotic resistance to such antibiotics as ampicillin, kanamycin, chloramphenicol, erythromycin, tetracycline, neomycin, hygromycin or methotrexate.

Furthermore, selection may be accomplished by co-transformation, e.g., as described in WO 91/17243, where the selectable marker is on a separate vector.

The vectors of the present invention preferably contain an element(s) that permits stable integration of the vector, or of a smaller part of the vector, into the host cell genome or autonomous replication of the vector in the cell independent of the genome of the cell.

The vectors, or smaller parts of the vectors, may be integrated into the host cell genome when introduced into a host cell. For chromosomal integration, the vector may rely on the nucleic acid sequence encoding the polypeptide or any other element of the vector for stable integration of the vector into the genome by homologous or nonhomologous recombination.

Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences.

The copy number of a vector, an expression cassette, an amplification unit, a gene or indeed any defined nucleotide sequence is the number of identical copies that are present in a host cell at any time. A gene or another defined chromosomal nucleotide sequence may be present in one, two, or more copies on the chromosome. An autonomously replicating vector may be present in one, or several hundred copies per host cell.

For autonomous replication, the vector may further comprise an origin of replication enabling the vector to replicate autonomously in the host cell in question. Examples of bacterial origins of replication are the origins of replication of plasmids pBR322, pUC19, pACYC177, pACYC184, pUB110, pE194, pTA1060, and pAMβ1. The origin of replication may be one having a mutation which makes its functioning temperature-sensitive in the host cell (see, e.g., Ehrlich, 1978, *Proceedings of the National Academy of Sciences USA* 75:1433).

The present invention also relates to recombinant host cells, comprising a nucleic acid sequence of the invention, which are advantageously used in the recombinant production of the polypeptides. The term "host cell" encompasses any progeny of a parent cell which is not identical to the parent cell due to mutations that occur during replication.

The cell is preferably transformed with a vector comprising a nucleic acid sequence of the invention followed by integration of the vector into the host chromosome. "Transformation" means introducing a vector comprising a nucleic acid sequence of the present invention into a host cell so that the vector is maintained as a chromosomal integrant or as a self-replicating extra-chromosomal vector. Integration is generally considered to be an advantage as the nucleic acid sequence is more likely to be stably maintained in the cell. Integration of the vector into the host chromosome may occur by homologous or non-homologous recombination as described above.

The choice of a host cell will to a large extent depend upon the gene encoding the polypeptide and its source. The host cell may be a unicellular microorganism, e.g., a prokaryote, or a non-unicellular microorganism, e.g., a eukaryote. Useful unicellular cells are bacterial cells such as gram positive bacteria including, but not limited to, a *Bacillus* cell, e.g., *Bacillus alkalophilus*, *Bacillus* amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis, and Bacillus thuringiensis; or a Streptomyces cell, e.g., Streptomyces lividans or Streptomyces murinus, or gram negative bacteria such as E. coli and Pseudomonas sp. In a preferred embodiment, the bacterial host cell is a Bacillus lentus, Bacillus licheniformis, Bacillus stearothermophilus or Bacillus subtilis cell.

The transformation of a bacterial host cell may, for instance, be effected by protoplast transformation (see, e.g., Chang and Cohen, 1979, Molecular General Genetics 168:111–115), by using competent cells (see, e.g., Young and Spizizin, 1961, Journal of Bacteriology 81:823–829, or Dubnar and Davidoff-Abelson, 1971, Journal of Molecular Biology 56:209–221), by electroporation (see, e.g., Shigekawa and Dower, 1988, Biotechniques 6:742–751), or by conjugation (see, e.g., Koehler and Thorne, 1987, Journal of Bacteriology 169:5771–5278).

The transformed or transfected host cells described above are cultured in a suitable nutrient medium under conditions permitting the expression of the desired polypeptide, after which the resulting polypeptide is recovered from the cells, or the culture broth.

The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The media are prepared using procedures known in the art (see, e.g., references for bacteria and yeast; Bennett, J. W. and LaSure, L., editors, More Gene Manipulations in Fungi, Academic Press, CA, 1991).

If the polypeptide is secreted into the nutrient medium, the polypeptide can be recovered directly from the medium. If the polypeptide is not secreted, it is recovered from cell lysates. The polypeptide are recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e.g. ion exchange chromatography, gelfiltration chromatography, affinity chromatography, or the like, dependent on the type of polypeptide in question.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., Protein Purification, J. -C. Janson and Lars Ryden, editors, VCH Publishers, New York, 1989).

DETAILED DESCRIPTION OF THE INVENTION

A method for constructing a cell comprising at least two copies of a gene of interest stably integrated into the chromosome in different positions according to the first aspect of the invention.

In the method of the invention it is envisioned that after the directed and selectable integration of the DNA construct into the chromosome of the host cell by the first homologous recombination, a second recombination can take place between a DNA fragment comprised in the construct and a homologous host cell DNA sequence located adjecent to the gene(s) of step b) of the method of the first aspect, where the DNA fragment of the construct is homologous to said host cell DNA sequence.

Accordingly a preferred embodiment of the invention relates to the method of the first aspect, wherein subsequent to the step of introducing the DNA construct and cultivating the cell under selective conditions, or subsequent to the step of selecting a host cell, a second recombination takes place between the DNA fragment and the homologous host cell DNA sequence.

A preferred embodiment of the invention relates to the method of the first aspect, wherein subsequent to step d) and prior to step e) a second recombination takes place between the DNA fragment and the homologous host cell DNA sequence.

Further it is envisioned that one might add a marker gene to the DNA construct, which could ease selection of first recombination integrants, where the marker gene would be excised from the host cell chromosome again by the second recombination as described above.

In a preferred embodiment the invention relates to the method of the first aspect, where the DNA construct further comprises at least one marker gene which is located in the construct such that it is recombined out of the chromosome by the second recombination; preferably the at least one marker gene confers resistance to an antibiotic, more preferably the antibiotic is chosen from the group consisting of chloramphenicol, kanamycin, ampicillin, erythromycin, spectinomycin and tetracycline; and most preferably a host cell is selected which grows under the selective conditions, and which does not contain the at least one marker gene in the chromosome.

The method of the invention can also be carried out by including a marker gene in that part of the DNA construct which remains integrated in the chromosome after the second recombination event. However as it is preferred not to have marker genes in the chromosome, an alternative way of removing the marker gene must be employed after the integration has been carried out. Specific restriction enzymes or resolvases that excise portions of DNA, if it is flanked on both sides by certain recognition sequences known as resolvase sites or res-sites, are well known in the art, see e.g. WO 96/23073 (Novo Nordisk A/S) which is included herein by reference.

A preferred embodiment of the invention relates to the method of the first aspect, where the DNA construct further comprises at least one marker gene located between the altered copy and the DNA fragment, and wherein the at least one marker gene is flanked by nucleotide sequences that are recognized by a specific resolvase, preferably the nucleotide sequences are res; even more preferably the at least one marker gene is excised from the chromosome by the action of a resolvase enzyme subsequent to selecting a host cell that grows under the selective conditions.

The gene of interest may encode an enzyme that is naturally produced by the host cell, indeed one may simply want to increase the number of copies of a gene endogenous to the host cell.

Accordingly a preferred embodiment of the invention relates to the method of the first aspect, wherein the gene of interest originates from the host cell.

In another preferred embodiment the invention relates to the method of the first aspect, wherein the gene of interest encodes an enzyme, preferably an amylolytic enzyme, a lipolytic enzyme, a proteolytic enzyme, a cellulytic enzyme, an oxidoreductase or a plant cell-wall degrading enzyme, and more preferably an enzyme with an activity selected from the group consisting of aminopeptidase, amylase, amyloglucosidase, carbohydrase, carboxypeptidase, catalase, cellulase, chitinase, cutinase, cyclodextrin glycosyltransferase, deoxyribonuclease, esterase, galactosidase, beta-galactosidase, glucoamylase, glucose oxidase, glucosidase, haloperoxidase, hemicellulase, invertase, isomerase, laccase, ligase, lipase, lyase, mannosidase, oxidase, pectinase, peroxidase, phytase, phenoloxidase, polyphenoloxidase, protease, ribonuclease, transferase, transglutaminase, or xylanase.

As mentioned above, the gene of interest may be endogenous to the host cell, however it may be advantageous if the production cell obtained by the method of the invention contains as little exogenous, foreign, or heterologous DNA as possible when the integration procedure is completed.

Consequently a preferred embodiment of the invention relates to the method of the first aspect, wherein the selected host cell that grows under the selective conditions comprises substantially no exogenous DNA, preferably less than 500 basepairs per integrated gene of interest, more preferably less than 300 bp, even more preferably less than 100 bp, still more preferably less than 50 bp, more preferably less than 25 bp per integrated gene of interest, or most preferably no exogenous DNA.

Yet a preferred embodiment of the invention relates to the method of the first aspect, wherein the selected host cell that grows under the selective conditions comprises DNA only of endogenous origin.

Another embodiment relates to the method, wherein the host cell selected in step e) of the first aspect comprises DNA only of endogenous origin.

Many ways exist in the art of rendering a gene non-functional by alteration or manipulation, such as partially deleting the gene or the promoter of the gene, or by introducing mutations in the gene or the promoter region of the gene.

A preferred embodiment of the invention relates to the method of the first aspect, wherein the conditionally essential chromosomal gene(s) of the host cell is altered by partially deleting the gene(s), or by introducing one or more mutations in the gene(s).

The present invention relies on rendering at least one conditionally essential chromosomal gene(s) in the host cell non-functional in a step, and in particular relies on a number of conditionally essential genes to be rendered non-functional. The gene(s) may be rendered non-functional by a partial deletion or a mutation as known in the art; specifically the gene(s) may be rendered non-functional through the use of a "Deletion plasmid(s)" as shown herein in non-limiting examples below. For each of the preferred embodiments relating to the altered chromosomal gene(s) of step b) of the method of the first aspect, the most preferred embodiment is shown by non-limiting examples herein and reference is made to the genetic tools constructed for that purpose, such as the PCR primer sequences used for constructing the "Deletion plasmid(s)".

Accordingly a preferred embodiment of the invention relates to the method of the first aspect, wherein the conditionally essential chromosomal gene(s) of the host cell that is altered encodes a D-alanine racemase, preferably the gene(s) is a dal homologue from a *Bacillus* cell, more preferably the gene is homologous to dal from *Bacillus subtilis*, and most preferably the gene(s) is the dal gene of *Bacillus licheniformis*.

Another preferred embodiment of the invention relates to the method of the first aspect, wherein the conditionally essential chromosomal gene(s) of the host cell that is altered encodes a D-alanine racemase and is at least 75% identical, preferably 80% identical, or preferably 85% identical, more preferably 90% identical, or more preferably 95% and most preferably at least 97% identical to the dal sequence of *Bacillus licheniformis* shown in positions 1303 to 2469 in SEQ ID NO:12.

The conditionally essential gene(s) may encode polypeptides involved in the utilization of specific carbon sources such as xylose or arabinose, in which case the host cell is unable to grow in a minimal medium supplemented with only that specific carbon source when the gene(s) are non-functional.

A preferred embodiment of the invention relates to the method of the first aspect, wherein the conditionally essential chromosomal gene(s) of the host cell that is altered is one or more genes that are required for the host cell to grow on minimal medium supplemented with only one specific main carbon-source.

A preferred embodiment of the invention relates to the method of the first aspect, wherein the conditionally essential chromosomal gene(s) of the host cell that is altered is of a xylose operon, preferably the gene(s) is homologous to the xylA gene from *Bacillus subtilis*, and most preferably the gene(s) is homologous to one or more genes of the xylose isomerase operon of *Bacillus licheniformis*.

A preferred embodiment of the invention relates to the method of the first aspect, wherein the conditionally essential chromosomal gene(s) of the host cell that is altered encodes a galactokinase (EC 2.7.1.6), an UTP-dependent pyrophosphorylase (EC 2.7.7.10), an UDP-glucose-dependent uridylyltransferase (EC 2.7.7.12), or an UDP-galactose epimerase (EC 5.1.2.3), preferably the gene(s) encodes an UDP-galactose epimerase (EC 5.1.2.3), more preferably the gene(s) is homologous to galE of a *Bacillus*, and most preferably the gene is galE of *Bacillus licheniformis*.

A preferred embodiment of the invention relates to the method of the first aspect, wherein the conditionally essential chromosomal gene(s) of the host cell that is altered is one or more gene(s) of a gluconate operon, preferably the gene(s) encodes a gluconate kinase (EC 2.7.1.12) or a gluconate permease or both, more preferably the gene(s) is one or more genes homologous to the gntk or gntp genes from *Bacillus subtilis*, and most preferably the gene(s) is the gntk or gntP gene from *Bacillus licheniformis*.

Another preferred embodiment of the invention relates to the method of the first aspect, wherein the conditionally essential chromosomal gene(s) of the host cell that is altered is one or more gene(s) of a gluconate operon, preferably the gene(s) encodes a gluconate kinase (EC 2.7.1.12) or a gluconate permease or both and is at least 75% identical, preferably 85% identical, more preferably 95% and most preferably at least 97% identical to any of the gntk and gntP sequences of *Bacillus licheniformis*.

Another preferred embodiment of the invention relates to the method of the first aspect, wherein the conditionally essential chromosomal gene(s) of the host cell that is altered is one or more gene(s) of a glycerol operon, preferably the gene(s) encodes a glycerol uptake facilitator (permease), a glycerol kinase, or a glycerol dehydrogenase, more preferably the gene(s) is one or more genes homologous to the glpP, glpF, glpK, and glpD genes from *Bacillus subtilis*, and most preferably the gene(s) is one or more genes of glpP, glpF, glpK, and glpD genes from *Bacillus licheniformis* shown in SEQ ID NO:26.

Still another preferred embodiment of the invention relates to the method of the first aspect, wherein the conditionally essential chromosomal gene(s) of the host cell that is altered is one or more gene(s) of a glycerol operon, preferably the gene(s) encodes a glycerol uptake facilitator (permease), a glycerol kinase, or a glycerol dehydrogenase, and is at least 75% identical, preferably 85% identical, more preferably 95% and most preferably at least 97% identical to any of the glpP, glpF, glpk, and glpD sequences of *Bacillus licheniformis* shown in SEQ ID NO:26.

One preferred embodiment of the invention relates to the method of the first aspect, wherein the conditionally essential chromosomal gene(s) of the host cell that is altered is one or more gene(s) of an arabinose operon, preferably the gene(s) encodes an arabinose isomerase, more preferably the gene(s) is homologous to the araA gene from *Bacillus subtilis*, and most preferably the gene(s) is the araA gene from *Bacillus licheniformis* shown in SEQ ID NO:38.

A preferred embodiment of the invention relates to the method of the first aspect, wherein the conditionally essential chromosomal gene(s) of the host cell that is altered is one or more gene(s) of an arabinose operon, preferably the gene(s) encodes an arabinose isomerase, and is at least 75% identical, preferably 85% identical, more preferably 95% and most preferably at least 97% identical to the araA sequence of *Bacillus licheniformis* shown in SEQ ID NO:38.

Other conditionally essential genes are well-described in the literature, for instance genes that are required for a cell to synthesize one or more amino acids, where a nonfunctional gene encoding a polypeptide required for synthesis of an amino acid renders the cell auxotrophic for that amino acid, and the cell can only grow if the amino acid is supplied to the growth medium. Restoration of the functionality of such a gene allows the cell to synthesise the amino acid on its own, and it becomes selectable against a background of auxotrophic cells.

Consequently, a preferred embodiment of the invention relates to the method of the first aspect, wherein the conditionally essential chromosomal gene(s) of the host cell encodes one or more polypeptide(s) involved in amino acid synthesis, and the non-functionality of the gene(s) renders the cell auxotrophic for one or more amino acid(s), and wherein restoration of the functionality of the gene(s) renders the cell prototrophic for the amino acid(s).

A particularly preferred embodiment of the invention relates to the method of the first aspect, wherein the conditionally essential chromosomal gene(s) of the host cell encodes one or more polypeptide(s) involved in lysine or methionine synthesis, more preferably the gene(s) is homologous to the metC or the lysA genes from *Bacillus subtilis*, and most preferably the gene(s) is the metC or the lysA gene from *Bacillus licheniformis*.

Another particularly preferred embodiment of the invention relates to the method of the first aspect, wherein the conditionally essential chromosomal gene(s) of the host cell is at least 75% identical, preferably 85% identical, more preferably 95% identical and most preferably at least 97% identical to the metC sequence of *Bacillus licheniformis* shown in SEQ ID NO:42 or the lysA sequence of *Bacillus licheniformis* shown in SEQ ID NO:48.

As described herein the method of the invention is very relevant for the biotech industry and a number of preferred organisms are very well known in this industry, especially Gram positive host cells, and certainly host cells of the *Bacillus* genus, specifically *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis*, and *Bacillus thuringiensis*.

A preferred embodiment of the invention relates to the method of the first aspect, wherein the host cell is a Gram-positive bacterial cell, preferably a *Bacillus* cell, and most preferably a *Bacillus* cell chosen from the group consisting of *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis*, and *Bacillus thuringiensis*.

Another preferred embodiment of the invention relates to the method of the first aspect, wherein the DNA construct is a plasmid.

As described elsewhere herein, the present invention provides genetic tools for carrying out the method of the invention, such as host cells, and DNA constructs of the invention, such as a DNA construct of the second aspect comprising:

i) an altered non-functional copy of a conditionally essential chromosomal gene(s) from a host cell, preferably the copy is partially deleted; and ii) at least one copy of a gene of interest flanked on one side by i) and on the other side by a DNA fragment homologous to a host cell DNA sequence located on the host cell chromosome adjacent to the conditionally essential gene(s) of i).

A preferred embodiment of the invention relates to the DNA construct of the second aspect, wherein the conditionally essential chromosomal gene(s) of the host cell that is altered in i) encodes a D-alanine racemase, preferably the gene(s) is a dal homologue from a *Bacillus* cell, more preferably the gene is homologous to dal from *Bacillus subtilis*, and most preferably the gene is the dal gene of *Bacillus licheniformis*.

Another preferred embodiment of the invention relates to the DNA construct of the second aspect, wherein the conditionally essential chromosomal gene(s) of the host cell that is altered in i) encodes a D-alanine racemase and is at least 75% identical, preferably 80% identical, or preferably 85% identical, more preferably 90% identical, or more preferably 95% and most preferably at least 97% identical to the dal sequence of *Bacillus licheniformis* shown in positions 1303 to 2469 in SEQ ID NO:12.

Yet another preferred embodiment of the invention relates to the DNA construct of the second aspect, wherein the altered non-functional copy of a conditionally essential chromosomal gene(s) from a host cell is one or more gene(s) that is required for the host cell to grow on minimal medium supplemented with only one specific main carbon-source.

A preferred embodiment of the invention relates to the DNA construct of the second aspect, wherein the conditionally essential chromosomal gene(s) of the host cell that is altered in i) is one or more genes of a xylose operon, preferably the gene(s) is homologous to the xylA gene from

*Bacillus subtilis*, and most preferably the gene(s) is homologous to one or more genes of the xylose isomerase operon of *Bacillus licheniformis*.

Still another preferred embodiment of the invention relates to the DNA construct of the second aspect, wherein the chromosomal gene(s) of the host cell that is altered in i) encodes a galactokinase (EC 2.7.1.6), an UTP-dependent pyrophosphorylase (EC 2.7.7.10), an UDP-glucose-dependent uridylyltransferase (EC 2.7.7.12), or an UDP-galactose epimerase (EC 5.1.2.3), preferably the gene(s) encodes an UDP-galactose epimerase (EC 5.1.2.3), more preferably the gene(s) is homologous to the galE gene of *Bacillus subtilis*, and most preferably the gene(s) is the galE gene of *Bacillus licheniformis*.

One more preferred embodiment of the invention relates to the DNA construct of the second aspect, wherein the conditionally essential chromosomal gene(s) is one or more genes of a gluconate operon, preferably the gene(s) encodes a gluconate kinase (EC 2.7.1.12) or a gluconate permease or both, more preferably the gene(s) is homologous to the gntk or gntP genes from *Bacillus subtilis*, and most preferably the gene(s) is one or more genes of gntk and gntP from *Bacillus licheniformis*.

Still another preferred embodiment of the invention relates to the DNA construct of the second aspect, wherein the conditionally essential chromosomal gene(s)is one or more gene(s) of a glycerol operon, preferably the gene(s) encodes a glycerol uptake facilitator (permease), a glycerol kinase, or a glycerol dehydrogenase, more preferably the gene(s) is one or more genes homologous to the glpP, glpF, glpK, and glpD genes from *Bacillus subtilis*, and most preferably the gene(s) is one or more genes of glpP, glpF, glpk, and glpD genes from *Bacillus licheniformis* shown in SEQ ID NO:26.

A particularly preferred embodiment of the invention relates to the DNA construct of the second aspect, wherein the conditionally essential chromosomal gene(s) is one or more gene(s) of a glycerol operon, preferably the gene(s) encodes a glycerol uptake facilitator (permease), a glycerol kinase, or a glycerol dehydrogenase, and is at least 75% identical, preferably 85% identical, more preferably 95% and most preferably at least 97% identical to any of the glpP, glpF, glpk, and glpD sequences of *Bacillus licheniformis* shown in SEQ ID NO:26.

One more preferred embodiment of the invention relates to the DNA construct of the second aspect, wherein the conditionally essential chromosomal gene(s) is one or more gene(s) of an arabinose operon, preferably the gene(s) encodes an arabinose isomerase, more preferably the gene(s) is homologous to the araA gene from *Bacillus subtilis*, and most preferably the gene(s) is the araA gene from *Bacillus licheniformis* shown in SEQ ID NO:38.

A preferred embodiment of the invention relates to the DNA construct of the second aspect, wherein the conditionally essential chromosomal gene(s) is one or more gene(s) of an arabinose operon, preferably the gene(s) encodes an arabinose isomerase, and is at least 75% identical, preferably 85% identical, more preferably 95% and most preferably at least 97% identical to the araA sequence of *Bacillus licheniformis* shown in SEQ ID NO:38.

Yet another preferred embodiment of the invention relates to the DNA construct of the second aspect, wherein the conditionally essential chromosomal gene(s) encodes one or more polypeptide(s) involved in amino acid synthesis, and where the non-functionality of the gene(s) when present in a cell with no other functional copy(ies) of the gene(s) renders the cell auxotrophic for one or more amino acid(s), and wherein restoration of the functionality of the gene(s) renders the cell prototrophic for the amino acid(s); preferably the conditionally essential chromosomal gene(s) encodes one or more polypeptide(s) involved in lysine or methionine synthesis, more preferably the gene(s) is homologous to the metC or the lysA genes from *Bacillus subtilis*, and most preferably the gene(s) is the metC or the lysA gene from *Bacillus licheniformis*. Still more preferably the conditionally essential chromosomal gene(s) is at least 75% identical, preferably 85% identical, more preferably 95% and most preferably at least 97% identical to the metC sequence of *Bacillus licheniformis* shown in SEQ ID NO:42 or the lysA sequence of *Bacillus licheniformis* shown in SEQ ID NO:48.

The present invention provides a method for constructing a production host cell that is very useful to the biotech industry, such as a host cell of the third aspect comprising at least two copies of a gene of interest stably integrated into the chromosome, where at least one copy is integrated adjacent to a conditionally essential locus and wherein the cell is obtainable by any of the methods defined in the first aspects.

The method of the first aspect describes the integration of a gene of interest into the chromosome of a host cell, so that the gene of interest is integrated in a position that is adjecent to the conditionally essential locus. The exact relative positions of the gene of interest and the locus are not of major relevance for the method, however generally speaking it is of interest to minimize the distance in basepairs separating the two, both to achieve a more stable integration, but also to minimize the integration of superfluous DNA sequence into the host cell genome.

Accordingly a preferred embodiment of the invention relates to the host cell of the third aspect, wherein the gene of interest is separated from the conditionally essential locus by no more than 1000 basepairs, preferably no more than 750 basepairs, more preferably no more than 500 basepairs, even more preferably no more than 250 basepairs, and most preferably no more than 100 basepairs.

As mentioned above, it is of interest to minimize the presence of integrated or superfluous DNA sequence in the host cell genome, especially DNA of exogenous origin, and the ideal host cell contains only DNA of endogenous origin such as multiple copies of an endogenous gene of interest integrated in different well defined chromosomal locations.

Consequently a preferred embodiment of the invention relates to the host cell of the third aspect, which contains substantially no exogenous DNA, preferably less than 500 basepairs per integrated gene of interest, more preferably less than 300 bp, even more preferably less than 100 bp, still more preferably less than 50 bp, more preferably less than 25 bp per integrated gene of interest, or most preferably no exogenous DNA.

Another preferred embodiment of the invention relates to the host cell of the third aspect, which contains only endogenous DNA.

Certain bacterial strains are preferred as host cells in the biotech industry as mentioned previously.

A preferred embodiment of the invention relates to the host cell of the third aspect, which is a Gram-positive bacterial cell, preferably a *Bacillus* cell, and most preferably a *Bacillus* cell chosen from the group consisting of *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis,* and *Bacillus thuringiensis*.

Another preferred embodiment of the invention relates to the host cell of the third aspect, wherein a copy of the gene of interest is integrated adjecent to a gene encoding a D-alanine racemase, preferably a gene homologous to the dal gene from *Bacillus subtilis*, more preferably a gene at least 75% identical to the dal sequence of *Bacillus licheniformis* shown in positions 1303 to 2469 in SEQ ID NO:12, even more preferably 80% identical, or even more preferably a gene at least 85% identical, still more preferably 90% identical, more preferably at least 95% identical, and most preferably at least 97% identical to the dal sequence of *Bacillus licheniformis* shown in positions 1303 to 2469 in SEQ ID NO:12.

A particularly preferred embodiment of the invention relates to the host cell of the third aspect, wherein a copy of the gene of interest is integrated adjacent to a gene that is required for the host cell to grow on minimal medium supplemented with only one specific main carbon-source.

Yet another preferred embodiment of the invention relates to the host cell of the third aspect, wherein a copy of the gene of interest is integrated adjacent to a gene of a xylose operon, preferably adjecent to genes homologous to the xylR or xylA genes from *Bacillus subtilis*, and most preferably adjecent to xylR or xylA from *Bacillus licheniformis*.

One more preferred embodiment of the invention relates to the host cell of the third aspect, wherein a copy of the gene of interest is integrated adjecent to a gene encoding a galactokinase (EC 2.7.1.6), an UTP-dependent pyrophosphorylase (EC 2.7.7.10), an UDP-glucose-dependent uridylyltransferase (EC 2.7.7.12), or an UDP-galactose epimerase (EC 5.1.2.3), preferably adjecent to a gene encoding an UDP-galactose epimerase (EC 5.1.2.3), more preferably adjecent to a gene homologous to the galE gene from *Bacillus subtilis*, and most preferably adjecent to galE from *Bacillus licheniformis*.

An additional preferred embodiment of the invention relates to the host cell of the third aspect, wherein a copy of the gene of interest is integrated adjecent to a gene of a gluconate operon, preferably adjecent to a gene that encodes a gluconate kinase (EC 2.7.1.12) or a gluconate permease, more preferably adjecent to a gene homologous to a *Bacillus subtilis* gene chosen from the group consisting of gntR, gntK, gntP, and gntz, and most preferably adjecent to gntR, gntK, gntP, or gntz from *Bacillus licheniformis*.

Yet an additional preferred embodiment of the invention relates to the host cell of the third aspect, wherein a copy of the gene of interest is integrated adjecent to a gene of a glycerol operon, preferably the gene encodes a glycerol uptake facilitator (permease), a glycerol kinase, or a glycerol dehydrogenase, more preferably the gene is homologous to the glpp, glpF, glpk, or glpD gene from *Bacillus subtilis*, and most preferably the gene is the glpP, glpF, glpk, or glpD gene from *Bacillus licheniformis* shown in SEQ ID NO:26.

Another particularly preferred embodiment of the invention relates to the host cell of the third aspect, wherein a copy of the gene of interest is integrated adjecent to a gene of an arabinose operon, preferably the gene encodes an arabinose isomerase, more preferably the gene is homologous to the araA gene from *Bacillus subtilis*, and most preferably the gene is the araA gene from *Bacillus licheniformis* shown in SEQ ID NO:38.

Still a preferred embodiment of the invention relates to the host cell of the third aspect, wherein a copy of the gene of interest is integrated adjacent to a gene which encodes one or more polypeptide(s) involved in amino acid synthesis, and the non-functionality of the gene(s) renders the cell auxotrophic for one or more amino acid(s), and wherein restoration of the functionality of the gene(s) renders the cell prototrophic for the amino acid(s); preferably the gene of interest is integrated adjacent to a gene which encodes one or more polypeptide(s) involved in lysine or methionine synthesis, more preferably the gene(s) is homologous to the metC or the lysA genes from *Bacillus subtilis*, and most preferably the gene(s) is the metC or the lysA gene from *Bacillus licheniformis*. Also preferably the gene of interest is integrated adjacent to a gene which is at least 75% identical, preferably 85% identical, more preferably 95% and most preferably at least 97% identical to the metC sequence of *Bacillus licheniformis* shown in SEQ ID NO:42 or the lysA sequence of *Bacillus licheniformis* shown in SEQ ID NO:48.

The host cell of the third aspect is especially interesting for the industrial production of polypeptides such as enzymes.

A preferred embodiment of the invention relates to the host cell of the third aspect, wherein the gene of interest encodes an enzyme, preferably an amylolytic enzyme, a lipolytic enzyme, a proteolytic enzyme, a cellulytic enzyme, an oxidoreductase or a plant cell-wall degrading enzyme, and more preferably an enzyme selected from the group consisting of aminopeptidase, amylase, amyloglucosidase, carbohydrase, carboxypeptidase, catalase, cellulase, chitinase, cutinase, cyclodextrin glycosyltransferase, deoxyribonuclease, esterase, galactosidase, beta-galactosidase, glucoamylase, glucose oxidase, glucosidase, haloperoxidase, hemicellulase, invertase, isomerase, laccase, ligase, lipase, lyase, mannosidase, oxidase, pectinase, peroxidase, phytase, phenoloxidase, polyphenoloxidase, protease, ribonuclease, transferase, transglutaminase, or xylanase. Also preferably the gene of interest encodes an antimicrobial peptide, preferably an anti-fungal peptide or an anti-bacterial peptide; or the gene of interest encodes a peptide with biological activity in the human body, preferably a pharmaceutically active peptide, more preferably insulin/pro-insulin/pre-pro-insulin or variants thereof, growth hormone or variants thereof, or blood clotting factor VII or VIII or variants thereof.

A further preferred embodiment of the invention relates to the host cell of the third aspect, wherein no antibiotic markers are present.

The present invention teaches the construction of host cells that are suitable for use in the method of the first aspect, especially host cells wherein one, two or more conditionally essential genes are rendered non-functional. In non-limiting examples below is shown how the preferred conditionally essential genes of the invention are rendered non-functional through a partial deletion by using specific Deletion Plasmids of the invention. Specifically the present invention relates to a *Bacillus* cell of the fourth aspect, which is preferably a *Bacillus licheniformis* cell, wherein at least two conditionally essential genes are rendered non-functional, preferably the genes are chosen from the group consisting of xylA, galE, gntK, gntP, glpP, glpF, glpk, glpD, araA, metC, lysA, and dal.

The use of such a host cell of the third aspect is likewise envisioned in the method of the first aspect.

Another genetic tool provided by the present invention for the method of the first aspect, is a host cell comprising a DNA construct of the second aspect.

A final aspect of the invention relatest to a process for producing an enzyme of interest, comprising cultivating a cell of the third aspect under conditions appropriate for producing the enzyme, and optionally purifying the enzyme.

EXAMPLES

Example 1

*Bacillus licheniformis* SJ4671 (WO 99/41358) comprises two stably integrated amyL gene copies in its chromosome, inserted in opposite relative orientations in the region of the B. licheniformis alpha-amylase gene, amyL. The following example describes the insertion into this strain of a third amyL gene copy by selectable, directed integration into another defined region of the B. licheniformis chromosome resulting in a strain comprising three stable chromosomal copies of the amyL gene but which is devoid of foreign DNA.

Xylose Isomerase Deletion/Integration Outline (FIG. 1)

The sequence of the Bacillus lichenformis xylose isomerase region is available in GenBank/EMBL with accession number Z80222.

A plasmid denoted "Deletion plasmid" was constructed by cloning two PCR amplified fragments from the xylose isomerase region on a temperature-sensitive parent plasmid. The PCR fragments were denoted "A" and "B", wherein A comprises the xylR promoter and part of the xylR gene; and B comprises an internal fragment of xylA missing the promoter and the first 70 basepairs of the gene. A spectinomycin resistance gene flanked by resolvase (res) sites was introduced between fragments A and B on the plasmid. This spectinomycin resistance gene could later be removed by resolvase-mediated site-specific recombination.

The xylose isomerase deletion was transferred from the Deletion plasmid to the chromosome of a Bacillus target strain by double homologous recombination via fragments A and B, mediated by integration and excision of the temperature-sensitive plasmid. The resulting strain was denoted "Deletion strain". This strain is unable to grow on minimal media with xylose as sole carbon source.

An "Integration plasmid" was constructed for insertion of genes into the xylose isomerase region of the Deletion strain. We intended to PCR-amplify a fragment denoted "C" comprising the xylA promoter and about 1 kb of the xylA gene. However, as later described, only a smaller fragment denoted "D" comprising the xylA promoter and the first 250 basepairs of the xylA gene was succesfully amplified and cloned. The Integration plasmid comprises fragments A and D on a temperature-sensitive vector. An expression cassette was also cloned in the Integration plasmid between fragments A and D.

The temperature-sensitive Integration plasmid was transferred to the B. licheniformis Deletion strain and it integrated in the chromosome; subsequent excision of the temperature sensitive vector was ensured, and "Integration strains" could then be isolated which grow on minimal media with xylose as sole carbon source. Such Integration strains have restored the chromosomal xylA gene, by double homologous recombination via fragments A and D. In this process, the expression cassette has been integrated into the chromosome.

Plasmid Constructs

PCR amplifications were performed with Ready-To-Go PCR Beads from amersham pharmacia biotech as described in the manufacturers instructions, using an annealing temperature of 55° C.

Plasmids pSJ5128 and pSJ5129:

The A fragment (xylR promoter and part of the xylR gene) was amplified from Bacillus licheniformis PL1980 chromosomal DNA using primers:

183235; [HindIII ←Z80222 1242-1261→]

5'-GACTAAGCTTCTGCATAGTGAGAGAAGACG (SEQ ID NO:1)

183234: [EcoRI; BglII; NotI; MluI; SalI; ScaI ←Z80222 2137-2113→]

5'-GACTGAATTCAGATCTGCGGCCGCACGCGTGTCGACAGTACTGAAATAGAGGAA (SEQ ID NO:2)
AAAATAAGTTTTC

The PCR fragment was digested with EcoRI and HindIII and purified, then ligated to EcoRI and HindIII digested pUC19. The ligation mixture was transformed by electroporation into E. coli SJ2, and transformants were selected for ampicillin resistance (200 µg/ml). The PCR-fragments of three such ampicillin resistant transformants were sequenced and all were found to be correct. Two clones designated SJ5128 (SJ2/pSJ5128) and SJ5129 (SJ2/pSJ5129) were kept.

Plasmids pSJ5124 and pSJ5125:

The B fragment (an internal part of xylA, missing the promoter and the first 70 basepairs of the coding region), was amplified from B. licheniformis PL1980 chromosomal DNA using primers:

183230 [EcoRI ←Z80222 3328-3306→]

5'-GACTGAATTCCGTATCCATTCCTGCGATATGAG (SEQ ID NO:3)

183227 [BamHI; BglII ←Z80222 2318-2342→]

5'-GACTGGATCCAGATCTTATTACAACCCT-GATGAATTTGTCG (SEQ ID NO:4)

The PCR fragment was digested with EcoRI and BamHI, and purified, then ligated to EcoRI+BamHI digested pUC19 and transformed by electroporation into E. coli SJ2. Transformants were selected for ampicillin resistance (200 µg/ml). Two clones were correct as confirmed by DNA sequencing, and were kept as SJ5124 (SJ2/pSJ5124) and SJ5125 (SJ2/pSJ5125).

Plasmid pSJ5130:

The C fragment (comprising the xylA promoter and about 1 kb of the xylA gene) was PCR amplified from B. licheniformis PL1980 chromosomal DNA using primers:
183230 (SEQ ID NO:3)
183229 [BamHI; BglII; NheI; ClaI; SacII ←Z80222 2131-2156→]

5'-GACTGGATCCAGATCTGCTAGCATCGATCCGCGGCTATTTCCATTGAAAGCGATT (SEQ ID NO:5)
AATTG

The PCR fragment was digested with EcoRI and BamHI and purified, then ligated to EcoRI and BamHI digested pUC19 and transformed by electroporation, into *E. coli* SJ2. Transformants were selected for ampicillin resistance (200 µg/ml). One clone, comprising the full-length PCR fragment, was found to have a single basepair deletion in the promoter region, between the −35 and −10 sequences. This transformant was kept as SJ5130 (SJ2/pSJ5130).

Plasmid pSJ5131:

This plasmid was constructed as pSJ5130, above, but turned out to contain a 400 basepair PCR fragment only (the D fragment), comprising the xylA promoter and the first 250 basepairs of the xylA coding sequence. DNA sequencing confirmed that the no sequence errors were present in the fragment. The transformant was kept as SJ5131 (SJ2/pSJ5131).

Plasmids pSJ5197 and pSJ5198:

These plasmids comprise the A (xylR) fragment on a temperature-sensitive, mobilizable vector. They were constructed by ligating the 0.9 kb BglII-HindIII fragment from pSJ5129 to the 5.4 kb BglII-HindIII fragment from pSJ2739, and transforming *B. subtilis* DN1885 competent cells with the ligation mix followed by selecting for erythromycin resistance (5 µg/ml). Two clones were kept, SJ5197 (DN1885/pSJ5197) and SJ5198 (DN1885/pSJ5198).

Plasmids pSJ5211, pSJ5212:

These plasmids contain a res-spc-res cassette inserted next to the B fragment. They were constructed by ligating the 1.5 kb BclI-BamHI fragment from pSJ3358 into the BglII site of pSJ5124, and transforming the ligation mix into *E. coli* SJ2 and selecting for ampicillin resistance (200 µg/ml) and spectinomycin resistance (120 µg/ml) resistance. Two clones were kept, wherein the res-spc-res cassette was inserted in either of the possible orientations, SJ5211 (SJ2/pSJ5211) and SJ5212 (SJ2/pSJ5212).

The Deletion Plasmid

Plasmid pSJ5218:

This plasmid contains the res-spc-res cassette flanked by the A and B fragments. It was constructed by ligating the 2.5 kb EcoRI-BamHI fragment from pSJ5211 to the 5.3 kb EcoRI-BglII fragment from pSJ5197, and transforming the ligation mix into *B. subtilis* DN1885 and selecting for erythromycin (5 µg/ml) and spectinomycin resistance (120 µg/ml) resistance at 30° C. One transformant, SJ5218 (DN1885/pSJ5218) was kept.

The Integration Plasmids

Plasmids pSJ5247, pSJ5248:

These plasmids comprise the short 400 basepairs D fragment (PxylA-xylA) as well as the A fragment (xylR) on a temperature-sensitive, mobilizable vector. They were made by ligating the 0.4 kb BglII-EcoRI fragment from pSJ5131 to the 5.3 kb BglII-EcoRI fragment from pSJ5197, and transforming the ligation mix into *B. subtilis* DN1885 and selecting for erythromycin resistance (5 µg/ml) at 30° C. Two transformants, SJ5247 (DN1885/pSJ5247) and SJ5248 (DN1885/pSJ5248) were kept.

Construction of Strains with Chromosomal xylA Deletions

The deletion plasmid pSJ5218 was transformed into competent cells of the *B. subtilis* conjugation donor strain PP289-5 (which contains a chromosomal dal-deletion, and plasmids pBC16 and pLS20), transformants were selected for resistance to spectinomycin (120 µg/ml), erythromycin (5 µg/ml) and tetracycline (5 µg/ml) on plates with D-alanine (100 µg/ml) at 30° C. Two transformants were kept, SJ5219 and SJ5220.

The two-copy *B. licheniformis* alpha-amylase strain SJ4671, described in WO 99/41358 was used as recipient in conjugations.

Donor strains SJ5219 and SJ5220 were grown overnight at 30° C. on LBPSG plates (LB plates with phosphate (0.01 M $K_3PO_4$), glucose (0.4%), and starch (0.5%)) supplemented with D-alanine (100 µg/ml), spectinomycin (120 µg/ml), erythromycin (5 µg/ml) and tetracycline (5 µg/ml). The recipient strain was grown overnight on LBPSG plates.

An inoculation needle loopful of donor and recipient were mixed on the surface of a LBPSG plate with D-alanine (100 µg/ml), and incubated at 30° C. for 5 hours. This plate was then replicated onto LBPSG with erythromycin (5 µg/ml) and spectinomycin (120 µg/ml), and incubation was at 30° C. for 2 days. These four conjugations resulted in between 13 and 25 transconjugants.

Tetracycline-sensitive (indicating absence of pBC16) transconjugants were reisolated on LBPSG with erythromycin (5 µg/ml) and spectinomycin (120 µg/ml) at 50° C., incubated overnight, and single colonies from the 50° C. plates were inoculated into 10 ml TY liquid cultures and incubated with shaking at 26° C. for 3 days. Aliquots were then transferred into fresh 10 ml TY cultures and incubation proceeded overnight at 30° C. The cultures were plated on LBPSG with 120 µg/ml spectinomycin, after overnight incubation at 30° C. these plates were replica plated onto spectinomycin and erythromycin, respectively, and erythromycin sensitive, spectinomycin resistant isolates were obtained from all strain conjugations.

The following strains, containing the chromosomal xylA promoter and the first 70 basepairs of the xylA coding sequence replaced by the res-spc-res cassette, were kept:

SJ5231: SJ4671 recipient, SJ5219 donor.
SJ5232: SJ4671 recipient, SJ5220 donor.

Strain phenotypes were assayed on TSS minimal medium agar plates, prepared as follows. 400 ml $H_2O$ and 10 g agar is autoclaved at 121° C. for 20 minutes, and allowed to cool to 60° C. The following sterile solutions are added:

| | |
|---|---|
| 1 M Tris pH 7.5 | 25 ml |
| 2% $FeCl_3.6H_2O$ | 1 ml |
| 2% trisodium citrate dihydrate | 1 ml |
| 1 M $K_2HPO_4$ | 1.25 ml |
| 10% $MgSO_4.7H_2O$ | 1 ml |
| 10% glutamine | 10 ml; and |
| 20% glucose | 12.5 ml; or |
| 15% xylose | 16.7 ml |

*Bacillus licheniformis* SJ4671 grows well on both glucose and xylose TSS plates, forming brownish coloured colonies.

The xylA deletion strains SJ5231–SJ5232 grow well on glucose TSS plates, but only a very thin, transparent growth is formed on the TSS xylose plates, even after prolonged incubation. These strains are clearly unable to use xylose as the sole carbon source.

Directed and Selectable Integration into the xyl region.

Integration plasmid pSJ5247 (containing the D and A fragments), and as a negative control pSJ5198 (containing only the A fragment) were transformed into competent cells of the *B. subtilis* conjugation donor strain PP289-5 (which contains a chromosomal dal-deletion, and plasmids pBC16 and pLS20), transformants were selected for resistance to erythromycin (5 µg/ml) and tetracycline (5 µg/ml) on plates with D-alanine (100 µg/ml) at 30° C.

Transformants kept were:
SJ5255: PP289-5/pSJ5198.
SJ5257: PP289-5/pSJ5248.

Donor strains SJ5255 and SJ5257 were used in conjugations to recipient SJ5231. Selection of transconjugants was on erythromycin (5 µg/ml), at 30° C. Transconjugants were streaked on TSS plates with xylose, at 50° C. In parallel, SJ5221 was streaked as a xylose isomerase positive control strain (also at 50° C.).

After overnight incubation, all strains had formed a very thin, transparent growth. The control, however, was better growing and colonies were brownish.

After another day of incubation at 50° C., some brownish colonies were coming up on the background of thin, transparent growth, in transconjugants derived from SJ5257, i.e. the strain containing the Integration plasmid with the PxylA-xylA fragment (D). These colonies were steadily growing, and further colonies were coming up, during subsequent days of continued incubation at 50° C.

No brownish colonies (and no further growth than the thin, transparent growth seen after the first overnight incubation) were observed from transconjugants derived from SJ5255 (the negative control, unable to restore the chromosomal xylA gene).

Directed Integration of an Alpha-Amylase Gene into the xyl Region.

Construction of an amyL Containing Integration Plasmid

Plasmids pSJ5291 and pSJ5292 were constructed from the integration vector plasmid pSJ5247 by digestion of this plasmid with BglII, and insertion of the 1.9 kb amyL containing BglII-BclI fragment from pSJ4457 (described in WO 99/41358). The ligation mixture was transformed into B. subtilis DN1885 and two transformants were kept as SJ5291 and SJ5292.

Construction of Conjugative Donor Strains, Transfer to B. licheniformis Hosts, and Chromosomal Integration Plasmids pSJ5291 and pSJ5292 were transformed into competent cells of the B. subtilis conjugation donor strain PP289-5 (which contains a chromosomal dal-deletion, and plasmids pBC16 and pLS20), transformants were selected for resistance to erythromycin (5 μg/ml) and tetracycline (5 μg/ml) on plates with D-alanine (100 μg/ml) at 30° C.

Transformants kept were SJ5293 (PP289-5/pSJ5291) and SJ5294 (PP289-5/pSJ5292). These two strains were used as donors in conjugations to xylose isomerase deletion strains SJ5231 and SJ5232. Transconjugants were selected on LBPGA plates with erythromycin (5 μg/ml), and one or two tetracyclin-sensitive transconjugants from each conjugation were streaked on a TSS-xylose plate which was incubated at 50° C. After two days incubation, well-growing colonies were inoculated into liquid TY medium (10 ml) without antibiotics, and these cultures were incubated with shaking at 30° C. After overnight incubation, 100 μl from each culture were transferred into new 10 ml TY cultures, and incubation repeated. This procedure was repeated another two times, and in addition the cultures were plated on TSS-xylose plates at 30° C. After about a week, all plates were replicaplated onto TSS-xylose as well as LBPSG with erythromycin (5 μpg/ml). The following day, putative Em-sensitive strains were restreaked on the same plate types.

The following Em sensitive strains, which all grow well on TSS-xylose plates, were kept:

SJ5308 (from conjugation donor SJ5293, host SJ5231)
SJ5309 (from conjugation donor SJ5293, host SJ5231)
SJ5310 (from conjugation donor SJ5293, host SJ5232)
SJ5315 (from conjugation donor SJ5294, host SJ5231)

Southern Analysis

The two-copy amyL strain SJ4671, and strains SJ5308, SJ5309, SJ5310 and SJ5315, were grown overnight in TY-glucose, and chromosomal DNA was extracted. The chromosomal DNA was digested with HindIII, fragments separated by agarose gel electrophoresis, transferred to Immobilon-N® filters (Millipore®) and hybridised to a biotinylated probe based on HindIII digested pSJ5292 (using NEBlot Photope Kit and Photope Detection Kit 6K).

In the two-copy strain, the two amyL gene copies reside on a ~10 kb HindIII fragment. In addition, an ~2.8 kb fragment is hybridizing, which is due to hybridization to the xyl region. In the four strains with insertions of a third amyL gene into the xylose gene region, the ~2.8 kb fragment is missing and has been replaced by a fragment of ~4.6 kb. This is entirely as expected upon integration of the amyL gene into the xylose gene region. The ~10 kb fragment due to the two-copy insertion is retained.

In conclusion, the southern analysis shows that strains SJ5308. SJ5309, SJ5310 and SJ5315 have a correctly inserted third amyL gene copy in their chromosome.

Shake Flask Evaluation

Strains with the amyL gene integrated in the xylose isomerase region, as well as several control strains, were inoculated into 100 ml BPX medium in shake flasks and incubated at 37° C. with shaking at 300 rpm for 7 days.

Alpha-amylase activity in the culture broth was determinated by the Phadebas assay:

| Strain | Relative alpha-amylase Units/ml |
| --- | --- |
| SJ4270 (one copy amyL strain) | 100 |
| SJ4671 (two copy amyL strain) | 161 |
| SJ5231 (two copy amyL strain with xylA gene deletion) | 148 |
| SJ5308 (three-copy amyL strain) | 200 |
| SJ5309 (three-copy amyL strain) | 245 |
| SJ5310 (three-copy amyL strain) | 200 |
| SJ5315 (three-copy amyL strain) | 200 |

Aliquots from each shake flask were plated on amylase indicator plates. All colonies were amylase positive. Four single colonies from each of SJ4671, SJ5309 and SJ5315 were inoculated into fresh BPX shake flasks, which were cultured as above. Alpha-amylase activity in the culture broth was determinated by the Phadebas assay:

| Strain | Relative alpha-amylase Units/ml |
| --- | --- |
| SJ4671 (two copy amyL l strain) | 100 |
| SJ4671 | 102 |
| SJ4671 | 88 |
| SJ4671 | 84 |
| SJ5309 (three-copy amyL strain) | 149 |
| SJ5309 | 141 |
| SJ5309 | 135 |
| SJ5309 | 149 |
| SJ5315 (three-copy amyL strain) | 135 |
| SJ5315 | 147 |
| SJ5315 | 159 |
| SJ5315 | 153 |

Under these shake flask conditions, the three copy amyL strains (bold) seem to produce about 50% more alpha-amylase than the two-copy strain.

Example 2

A strain of Bacillus licheniformis having two stably integrated amyL gene copies in its chromosome, inserted in opposite relative orientations in the region of the B. licheniformis alpha-amylase gene, amyL, has been described in WO 99/41358, as SJ4671. A third copy of the amyL gene was inserted in xylRA as described above.

This describes the insertion into this three-copy strain of a fourth amyL gene copy by selectable, directed integration into another region of the B. licheniformis chromosome.

Gluconat Deletion/Integration Outline (FIG. 2)

The sequence region of the *Bacillus lichenformis* gluconate operon comprising the gntR, gntK, gntP, gntZ genes for utilization of gluconate is available in Genbank/EMBL with accession number D31631. The region can be schematically drawn as shown in FIG. 2.

A deletion was introduced by cloning, on a temperature-sensitive plasmid, the PCR amplified fragments denoted as "A" (containing part of the gntK and part of the gntP gene) and "B" (containing an internal fragment of gntz). As a help in the selection of deletion strains, a kanamycine resistance gene flanked by resolvase sites was introduced between fragments "A" and "B", resulting in the plasmid denoted "Deletion plasmid" in FIG. 2. This kanamycine resistance gene could later be removed by resolvase-mediated site-specific recombination, as described in WO 96/23073.

The deletion was transferred to the chromosome of target strains by double homologous recombination via fragments "A" and "B", mediated by integration and excision of the temperature-sensitive plasmid. The result was the strain, labelled "Deletion strain" in FIG. 2. This strain is unable to grow on minimal media with gluconate as sole carbon source.

Plasmid Constructs

To construct an Integration plasmid to be used for gene insertions, the PCR fragment "C" was amplified. This fragment contained an internal fragment of gntP of about 1 Kb. The Integration plasmid consists of fragments "B" and "C" on a temperature-sensitive vector. The expression cassette destined for integration is cloned between "B" and "C". Upon transfer to the *B. licheniformis* Deletion strain and integration and excision of the temperature-sensitive vector, strains could be isolated which grew on minimal media with gluconate as sole carbon source. Such strains had restored the chromosomal gntP gene by double homologous recombination via fragments "B" and "C". In this process, the expression cassette was integrated into the chromosome resulting in the "Integration strain" of FIG. 2.

PCR amplifications were performed with Ready-To-Go PCR Beads from amersham pharmacia biotech as described in the manufacturers instructions, using an annealing temperature of 55° C.

The Deletion Plasmids pMOL1789 and PMOL1790:

The "B" fragment (containing the internal part of the gntZ) was amplified from chromosomal DNA from *Bacillus licheniformis* using primers

187338 [AvaI ←D31631 4903-4922→]

5'-TATTTCCCGAGATTCTGTTATCGACTCGCTC (SEQ ID NO:6)

187339 [EagI ←D31631 5553-5538→]

5'-GTTTTCGGCCGCTGTCCGTTCGTCTTT (SEQ ID NO:7)

The fragment was digested with AvaI+EagI, ligated to AvaI+EagI digested pMOL1642, and the ligated plasmid was introduced, by transformation, into *B. subtilis* JA578 selecting for erythromycin resistance (5 µg/ml). The insert on three clones was sequenced, and all found to be correct. MOL1789 (JA578 (repF)/pMOL1789) and MOL1790 (JA578/pMOL1790) were kept. The endpoint of the "B" fragment relative to gntz is shown in FIG. 2.

Plasmids pMOL1820 and pMOL1821:

The "A" fragment (containing part of the gntK and part of the gntP gene), was amplified from chromosomal DNA of *Bacillus licheniformis* using primers

184733 [←D31631 3738-3712→]

5'-GTGTGACGGATAAGGCCGCCGTCATTG (SEQ ID NO:8)

184788 [←D31631 3041-3068→]

5'-CTCTTGTCTCGGAGCCTGCATTTTGGGG (SEQ ID NO:9)

The fragment was digested with ClaI+EcoRI, ligated to EcoRI+ClaI digested pMOL1789, and transformed, by transformation, into *B. subtilis* PL1801 selecting for erythromycin resistance (5 µg/ml). The insert on three clones was sequenced, and all found to be correct. MOL1820 (JA578/pMOL1820) and MOL1821 (JA578/pMOL1821) were kept. The endpoint of the "A" fragment relative to gntZ is shown in FIG. 2.

The Integration Plasmids pMOL1912 and pMOL1913:

These plasmids contain a short C-terminal part of gntK and the entire open reading frame of gntP (the "C" fragment) on a temperature-sensitive, mobilizable vector. They were made by ligating a 0.9 kb fragment amplified from chromosomal DNA of *Bacillus licheniformis* using primers:

B1656D07 [←D31631 3617-3642→]

5'-AGCATTATTCTTCGAAGTCGCATTGG (SEQ ID NO:10)

B1659F03 [BglII ←D31631 4637-4602→]

5'-TTAAGATCTTTTTTATACAAATAGGCT-TAACAATAAAGTAAATCC (SEQ ID NO: 11)

The fragment was digested with BglII+EcoRI, ligated to BglII+EcoRI digested pMOL1820, and the ligation mixture transformed, by transformation, into *B. subtilis* PL1801 selecting for erythromycin resistance (5 µg/ml). The insert on three clones was sequenced, and all found to be correct. MOL1912 (PL1801/pMOL1789) and MOL1913 (PL1801/pMOL1913) were kept. The endpoint of the "C" fragment relative to gntz is shown in FIG. 2.

These plasmids were found to express functional GntP even if they do not have a promoter sequence directly upstream of the gntP gene. In order to enable directed integration in the gntP region by selecting for growth on gluconate it was necessary to delete part of the N-terminal sequence of the gntP gene on the integration plasmid pMOL1912.

Plasmids pMOL1972 and pMOL1973:

These plasmids are Deletion derivatives of pMOL1912 which contain the entire gntP gene except for the first 158 bp coding for 53 amino acids of the N-terminal. The plasmid pMOL1912 was digested with StuI+EcoRV and re-ligated. The ligation mixture was transformed, by competence, into *B. subtilis* PL1801 selecting for erythromycin resistance (5 µg/ml). The deletion was verified by restriction digest. MOL1972 (PL1801/pMOL1972) and MOL1973 (PL1801/pMOL1973) were kept.

These plasmids do not support growth on TSS gluconate plates when introduced as free plasmids in a gntP deleted background.

Construction of Strains with Chromosomal gntP Deletions

The Deletion plasmid pMOL1920 was transformed into competent cells of the *B. subtilis* conjugation donor strain PP289-5 (which contains a chromosomal dal-deletion, and plasmids pBC16 and pLS20), selecting resistance to kanamycine (10 µg/ml), erythromycin (5 µg/ml) and tetracycline (5 μg/ml) on plates with D-alanine (100 μg/ml) at 30° C. Two transformants were kept, MOL1822 and MOL1823.

The two-copy *B. licheniformis* alpha-amylase strain SJ4671, described in WO 99/41358 was used as recipient in conjugations.

Donor strains MOL1822 and MOL1823 were grown overnight at 30° C. on LBPSG plates (LB plates with phosphate (0.01 M $K_3PO_4$), glucose (0.4%), and starch (0.5%)) supplemented with D-alanine (100 μg/ml), kanamycine (10 μg/ml), erythromycin (5 μg/ml) and tetracycline (5 μg/ml). The recipient strain was grown overnight on LBPSG plates.

A loopful of donor and recipient were mixed on the surface of a LBPSG plate with D-alanine (100 μg/ml), and incubated at 30° C. for 5 hours. This plate was then replicated onto LBPSG with erythromycin (5 μg/ml) and kanamycine (10 μg/ml), and incubation was at 30° C. for 2 days. These four conjugations resulted in between 25 and 50 transconjugants.

Tetracycline-sensitive (indicating absence of pBC16) transconjugants were reisolated on LBPSG with erythromycin (5 μg/ml) and kanamycin (10 μg/ml) at 50° C., incubated overnight, and single colonies from the 50° C. plates were inoculated into 10 ml TY liquid cultures and incubated with shaking at 26° C. for 3 days, then aliquots were transferred into fresh 10 ml TY cultures and incubation continued overnight at 30° C. The cultures were then plated on LBPSG with 10 μg/ml kanamycine, after overnight incubation at 30° C. these plates were replica plated onto kanamycine and erythromycin, respectively, and erythromycin sensitive, kanamycine resistant isolates were obtained from all strain combinations. The following strains, where part of the gntP gene coding for the C-terminal was replaced by the res-kana-res cassette, were kept:
MOL1871: SJ4671 recipient, MOL1822 donor.
MOL1872: SJ4671 recipient, MOL1823 donor.

Strain phenotypes were assayed on TSS minimal medium agar plates, prepared as follows:

400 ml $H_2O$ is added 10 g agar and is autoclaved at 121° C. for 20 minutes, and allowed to cool to 60° C. The following sterile solutions are added:

| | |
|---|---|
| 1 M Tris pH 7.5 | 25 ml |
| 2% $FeCl_3.6H_2O$ | 1 ml |
| 2% trisodium citrate dihydrate | 1 ml |
| 1 M $K_2HPO_4$ | 1.25 ml |
| 10% $MgSO_4.7H_2O$ | 1 ml |
| 10% glutamine | 10 ml, and |
| 20% glucose | 12.5 ml, or |
| 15% gluconate | 16.7 ml |

*Bacillus licheniformis* SJ4671 grows well on both glucose and gluconate TSS plates, forming brownish coloured colonies. The gntP Deletion strains MOL1871 and MOL1872 grow well on glucose TSS plates, but only a very thin, transparent growth is formed on the TSS gluconate plates, even after prolonged incubation. These strains are clearly unable to use gluconate as the sole carbon source.

The same gntP deletion procedure is performed on the three copy strain SJ5309 described earlier to prepare for integration of a fourth copy of the amylase expression cassette.

Directed and Selectable Integration into the gnt Region

Integration plasmid pMOL1972 (containing the "B" and "C" fragments), and as a negative control pMOL1789 (containing only the "B" fragment), were transformed into competent cells of the *B. subtilis* conjugation donor strain PP289-5 (which contains a chromosomal dal-deletion, and plasmids pBC16 and pLS20), selecting resistance to erythromycin (5 μg/ml) and tetracycline (5 μg/ml) on plates with D-alanine (100 μg/ml) at 30° C. Transformants kept were:
MOL1974: PP289-5/pMOL1972.
MOL1975: PP289-5/pMOL1973.

Donor strains MOL1974 and MOL1975 were used in conjugations to recipient MOL1871 and MOL1872. Selection of transconjugants was on erythromycin (5 μg/ml), at 30° C. Transconjugants were streaked on TSS plates with gluconate, at 50° C. In parallel, SJ4671 was streaked as a gluconate positive control strain (also at 50° C.).

After overnight incubation, all strains had formed a very thin, transparent growth. The control, however, was better growing and colonies were brownish. After another day of incubation at 50° C., some brownish colonies were coming up on the background of thin, transparent growth, in transconjugants derived from MOL1871 and MOL1872. These colonies were steadily growing, and further colonies appeared, during subsequent days of continued incubation at 50° C.

No colonies were observed from the gntP deleted strains MOL1871 and MOL1872.

Directed Integration of an Alpha-Amylase Gene into the gnt Region

Construction of an amyL Containing Integration Plasmid.

The following is a construction plan for integrating an expression cassette with the alpha-amylase gene in the gnt region making use of the selection principle described above. The integration plasmid pMOL1972 is digested with BglII, and a 1.9 kb BglII-BclI fragment containing amyL from pSJ4457 (described in WO 99/41358) is inserted by ligation. The ligation mixture is then transformed into *B. subtilis* DN1885 and transformants selected on LBPSG plates with erythromycin (5 μg/ml) are verified by restriction digestion of plasmid DNA.

Conjugative Donor Strains, Transfer to *B. licheniformis*, and Chromosomal Integration.

The Integration plasmid with the expression cassette is transformed into competent cells of the *B. subtilis* conjugation donor strain PP289-5 (which contains a chromosomal dal-deletion, and plasmids pBC16 and pLS20), selecting resistance to erythromycin (5 μg/ml) and tetracycline (5 μg/ml) on plates with D-alanine (100 μg/ml) at 30° C.

Transformants comprising the Integration plasmid with the expression cassette are preserved and used as donors in conjugations with a gntP Deletion recipient of the three-copy strain SJ5309, which in turn was constructed as described for the Deletion strains MOL1871 and MOL1872 described above.

Transconjugants are selected on LBPGA plates with erythromycin (5 μg/ml), and one or two tetracyclin-sensitive transconjugants from each conjugation is streaked on a TSS-gluconate plate which is incubated at 50° C. After two days incubation, well-growing colonies are inoculated into liquid TY medium (10 ml) without antibiotics, and these cultures are incubated with shaking at 30° C. After overnight incubation, 100 μl from each culture is transferred into new 10 ml TY cultures, and incubated. This procedure is repeated twice, and in addition the cultures are plated on TSS-gluconate plates at 30° C.

After about a week, all plates are replica-plated onto TSS-gluconate as well as LBPSG with erythromycin (5 μg/ml) and incubated. The following day putative Em-sensitive strains are restreaked on the same plate types.

As for integration in the xylose region described earlier, Southern analysis and shake flask evaluation is performed to verify the site of integration in the gnt region of the alpha-amylase expression cassette and the increased yield from this four copy strain.

Example 3

Bacillus licheniformis SJ4671 (WO 99/41358) comprises two stably integrated amyL gene copies in its chromosome, inserted in opposite relative orientations in the region of the B. licheniformis alpha-amylase gene, amyL. The following example describes the insertion into this strain of a third amyL gene copy by selectable, directed integration into another region of the B. licheniformis chromosome.

D-alanine Racemase Deletion/Integration Outline

The DNA sequence of the Bacillus lichenformis D-alanine racemase region was determined in this work and is shown in positions 1303 to 2469 in SEQ ID NO:12. A plasmid denoted "Dal-Deletion plasmid" was constructed by cloning one 2281 bp PCR amplified fragment from the D-alanine racemase region of Bacillus lichenformis on a temperature-sensitive parent plasmid. The PCR 2281 bp fragment was denoted "A", wherein A comprises the sequence from 245 basepairs upstream of the ATG start codon of the dal gene to 867 basepairs downstream of the dal gene.

A deletion of 586 basepairs of the C-terminal part of the dal gene on the cloned fragment A was done resulting in a plasmid containing the fragments "B" and "C" as shown below. A spectinomycin resistance gene flanked by resolvase (res) sites was introduced between fragments "B" and "C" on the plasmid. This spectinomycin resistance gene could later be removed by resolvase-mediated site-specific recombination.

The D-alanine racemase deletion was transferred from the Dal-Deletion plasmid to the chromosome of a Bacillus target strain by double homologous recombination via fragments "B" and "C", mediated by integration and excision of the temperature-sensitive Dal-Deletion plasmid. The resulting strain was denoted "Dal-Deletion strain". This strain was unable to grow on media without D-alanine.

An Integration plasmid was constructed for insertion of genes into the D-alanine region of the Deletion strain. We intended to PCR-amplify a fragment denoted "D" comprising 1117 basepairs of the dal gene starting from 41 basepairs downstream of the ATG start codon. The promoter region was substituted with the T1 and T2 terminators from the 3'-terminal sequence of the Escherichia coli rrnB ribosome RNA operon (EMBL/e09023: basepair 197-295).

The Integration plasmid comprises fragments D and C on a temperature-sensitive vector. An expression cassette destined for integration was cloned between the fragments D and C. Upon transfer to the B. licheniformis deletion strain, integration, and excision of the temperature-sensitive vector, strains could be isolated which grow on media without D-alanine. Such "Integration strains" have restored the chromosomal dal gene, by double homologous recombination via fragments D and C. In this process, the expression cassette was integrated into the chromosome.

Plasmid Constructs

PCR amplifications were performed with Ready-To-Go PCR Beads from amersham pharmacia biotech as described in the manufacturers instructions, using an annealing temperature of 55° C.

Plasmids pJA744:

The A fragment (dal-region) was amplified from Bacillus licheniformis SJ4671 chromosomal DNA using primers:
148779; [Upstream of a SphI site in the dal region]

5'-GATGAACTTCTGATGGTTGC (SEQ ID NO:14)

148780: [BamHI<dal]

5'-AAAGGATCCCCCTGACTACATCTGGC (SEQ ID NO:15)

The PCR fragment was digested with SphI and BamHI and purified, then ligated to SphI and BamHI digested pPL2438. Transforming B. subtilis JA691 (repF+, dal−) competent cells with the ligation mix followed by selecting for kanamycin resistance (10 μg/ml). Correct clones could complement the JA691 dal phenotype.

Plasmid pJA770:

This plasmid contains a res-spc-res cassette inserted between the B and C fragments. It was constructed by ligating the 1.5 kb BclI-BamHI fragment from pSJ3358 into the BclI-BclI sites of pJA744. Transforming B. subtilis JA691 competent cells with the ligation mix followed by selecting for kanamycin resistance (10 μg/ml) and spectinomycin resistance (120 μg/ml). Orientation of the spectinomycin resistance gene was could be determined by cutting with BclI and BamHI.

Dal Deletion Plasmid

Plasmid pJA851

A fragment (comprising the ermC gene and the replication origin of pE194) was PCR amplified from pSJ2739 plasmid DNA using primers:
170046 [NotI; <ermC gene and the replication origin of pE194>]

5'-AAAGCGGCCGCGAGACTGTGACGGAT-GAATTGAAAAAGC (SEQ ID NO:16)

170047 [EcoRI; ←ermC gene and the replication origin of pE194→]

5'-AAAGAATTCGTGAAATCAGCTGGACTAAAAGG (SEQ ID NO:17)

The PCR fragment was digested with EcoRI and NotI and purified, then ligated to EcoRI and NotI digested pJA770. Transforming B. subtilis JA691 competent cells with the ligation mix followed by selecting for erythromycin resistance (5 μg/ml) and spectinomycin resistance (120 μg/ml).

Plasmid PJA748

A fragment (comprising the dal gene without the promotor region) was PCR amplified from Bacillus licheniformis SJ4671 DNA using primers:
150506 [BamHI; <dal gene]

5'-AAAGGATCCCGCAAGCAAAGTTGTTTTTCCGC (SEQ ID NO: 18)

150507 [KpnI; <–dal gene]

5'-AAAGGTACCGAAAGACATGGGCCGAAATCG (SEQ ID NO:19)

The PCR fragment was digested with KpnI and BamHI and purified, then ligated to KpnI and BamHI digested pPL2438. Transforming B. subtilis JA691 competent cells with the ligation mix followed by selecting for kanamycin resistance (10 μg/ml).

Plasmid PJA762

A fragment (comprising the $T_1$ and $T_2$ Terminators from the E. coli rrnB terminal sequence EMBL[e09023] from basepair 197 to 295) was PCR amplified from Escherichia coli SJ2 DNA using primers:

158089 [KpnI; <T$_1$ and T$_2$Terminators of rrnB]

5'-AAAGGTACCGGTAATGACTCTCTAGCTTGAGG (SEQ ID NO:20)

158090 [ClaI; <T$_1$ and T$_2$ Terminators of rrnB]

5'-CAAATCGATCATCACCGAAACGCGGCAGGCAGC (SEQ ID NO:21)

The PCR fragment was digested with KpnI and ClaI and purified, then ligated to KpnI and ClaI digested pJA748. Transforming B. subtilis JA691 competent cells with the ligation mix followed by selecting for kanamycin resistance (10 µg/ml).

Plasmid PJA767

A fragment (comprising the 0.7 kbp DNA sequence downstream of dal (DFS)) was PCR amplified from B. licheniformis SJ4671 (WO 99/41358) DNA using primers:

150508 [HindIII; <DFS]

5'-ATTAAGCTTGATATGATTATGAATGGAATGG (SEQ ID NO:22)

150509 [NheI; <DFS]

5'-AAAGCTAGCATCCCCCTGACTACATCTGGC (SEQ ID NO:23)

The PCR fragment was digested with HindIII and NheI and purified, then ligated to KpnI and ClaI digested pJA762. Transforming B. subtilis JA691 competent cells with the ligation mix followed by selecting for kanamycin resistance (10 µg/ml).

Plasmid pJA776

This plasmid contains the amyL cassette flanked by the D and C fragments. It was constructed by ligating the 2.8 kb HindIII-NheI fragment from pSJ4457 to the 4.2 kb BamHI-HindIII fragment from pJA767, and transforming the ligation mix into B. subtilis JA691 competent cells followed by selecting for kanamycin resistance (10 µg/ml).

Dal Integration Plasmid

Plasmid pJA1020

This plasmid contains the amyL cassette flanked by the D and C fragments. Further the plasmid contains the plasmid pE194 replication origin, repF and the Em$^r$-gene. It was constructed by ligating the 2.7 kb EcoRI-NheI fragment of pJA776 to the 3.8 kb EcoRI-NheI fragment of pJA851, and transforming the ligation mix into B. subtilis JA691 competent cells followed by selecting for erythromycin resistance (5 ||g/ml).

Construction of Chromosomal dal Deletions

The Deletion plasmid pJA851 was transformed into competent cells of the B. subtilis conjugation donor strain PP289-5 (which contains a chromosomal dal-deletion, and plasmids pBC16 and pLS20), and transformants were selected for resistance to spectinomycin (120 µg/ml), erythromycin (5 µg/ml), and tetracycline (5 µg/ml) on plates with D-alanine (100 µg/ml) at 30° C. Transformants were kept as JA954 and used as donor in the following conjugation experiments.

The two-copy amyL B. licheniformis SJ4671 (WO 99/41358) was used as recipient in the following conjugation experiments.

Donor strain JA954 were grown overnight at 30° C. on LBPSG plates (LB plates with phosphate (0.01 M K$_3$PO$_4$), glucose (0.4%), and starch (0.5%)) supplemented with D-alanine (100 µg/ml), spectinomycin (120 µg/ml), erythromycin (5 µg/ml) and tetracycline (5 µg/ml). The recipient strain SJ4671 was grown overnight on LBPSG plates.

Approx. one loop of an inoculation needle of donor and recipient each were mixed on the surface of a LBPSG plate with D-alanine (100 µg/ml), and incubated at 30° C. for 5 hours. This plate was then replicated onto LBPSG with erythromycin (5 µg/ml) and spectinomycin (120 µg/ml), and was incubated at 30° C. for 2 days. These four conjugations resulted in 13–25 transconjugants.

Tetracycline-sensitive (indicating absence of pBC16) transconjugants were reisolated on LBPSG plates with erythromycin (5 µg/ml) and spectinomycin (120 µg/ml) at 50° C., and incubated overnight. Single colonies from the 50° C. plates were inoculated into 10 ml TY liquid medium with D-alanine (100 µg/ml) and incubated with shaking at 26° C. for 3 days, whereafter aliquots were transferred into fresh 10 ml TY cultures and incubation was continued overnight at 30° C. The cultures were plated on LBPSG with 120 µg/ml spectinomycin and D-alanine (100 µg/ml), after overnight incubation at 30° C. these plates were replica plated onto LBPSG with/without D-alanine (100 µg/ml), spectinomycin and erythromycin, respectively.

D-Alanine autotrophic, erythromycin sensitive, and spectinomycin resistant isolates were obtained from all strain combinations. The following strain comprising the chromosomal dal promoter and the first 672 basepairs of the dal coding sequence replaced by the res-spc-res cassette, was kept:

B. licheniformis JA967: SJ4671 recipient, JA954 donor.

Strain phenotypes were assayed on LBPG with 120 µg spectinomycin supplemented with or without D-alanine (100 pg/ml)

Bacillus licheniformis SJ4671 grows well on both plates with or without D-alanine. The dal deletion strain JA967 growth well on LBPG D-alanine plates, but not on LBPG plates without D-alanine. These strains are clearly unable to grow without adding D-alanine to the media.

The Sequence of the B. licheniformis dal-region (SEQ ID NO:12):

The dal-region (comprising the ydcC gene, a terminator, the dal gene and the sequence downstream of dal (DFS)) was PCR amplified from Bacillus licheniformis ATCC14580 chromosomal DNA using the primers:

145507 [<ydcC–dal-DFS>]

5'-GCGTACCGTTAAAGTCGAACAGCG (SEQ ID NO:24)

150509 [NheI; <ydcC–dal-DFS>]

5'-AAAGCTAGCATCCCCCTGACTACATCTGGC (SEQ ID NO:25)

Sequencing of the D-alanine encoding sequence of Bacillus licheniformis that is shown in positions 1303–2469 of SEQ ID NO:12 and a subsequent homology search in the public databases revealed that the newly isolated dal gene has a sequence identity of only approx. 67% with the dal gene of Bacillus subtilis, no other D-alanine racemase encoding genes show a higher homolgoy to this new B. licheniformis dal gene.

Conjugative Donor Strains, Transfer to B. licheniformis, and Chromosomal Integration The Integration plasmid pJA1020 with the expression cassette is transformed into competent cells of the B. subtilis conjugation donor strain PP289-5 (which contains a chromosomal dal-deletion, and plasmids pBC16 and pLS20), selecting resistance to erythromycin (5 µg/ml) and tetracycline (5 µg/ml) on plates with D-alanine (100 µg/ml) at 30° C.

Transformants comprising the Integration plasmid with the expression cassette are preserved and used as donors in conjugations with a dal deletion recipient of the two-copy strain JA967.

Transconjugants are selected on LBPGA plates with erythromycin (5 µg/ml), and one or two tetracyclin-sensitive transconjugants from each conjugation is streaked on LBPG plate which is incubated at 50° C. After two days incubation, well-growing colonies are inoculated into liquid TY medium (10 ml) without antibiotics, and these cultures are incubated with shaking at 30° C. After overnight incubation, 100 µl from each culture is transferred into new 10 ml TY cultures, and incubated. This procedure is repeated twice, and in addition the cultures are plated on LBPG plates at 30° C.

All plates are replica-plated onto LBPGS, LBPGS with spectinomycine(120 µg/ml) and LBPSG with erythromycin (5 µg/ml) and incubated. The following day putative Spectinomycin- and erythromycin-sensitive strains are restreaked on the same plate types.

As for integration in the xylose region described earlier, Southern analysis and shake flask evaluation is performed to verify the site of integration in the dal region of the alpha-amylase expression cassette and the increased yield from this three copy strain.

Example 4

In this work we did a homology study on the *Bacillus subtilis* genome and a particular region of the *B. licheniformis* chromosome (SEQ ID NO:26), and we found that the *B. licheniformis* region contains the genes glpP, glpF, glpK and glpD. The size of the analyzed region is 5761 nucleotides, and the DNA sequence is shown in SEQ ID NO:26.

The glpP coding region extends from pos. 261 to pos. 818 in SEQ ID NO:26. A search of EMBL and Swiss-prot databases using the blast program revealed the closest homolog to be the *B. subtilis* glpP gene (on the DNA level) and the *B. subtilis* GlpP protein (on the protein level). The identity, on the DNA level, to the *B. subtilis* glpP coding region was 72.4% in an alignment constructed using the GAP program in the GCG program package (Wisconsin Package Version 10.0, Genetics Computer Group (GCG), Madison, Wis.). The identity of the deduced GlpP protein to the *B. subtilis* GlpP protein was 78.9%.

The glpF coding region extends from pos. 1048 to pos. 1863 in SEQ ID NO:26. A search of EMBL ans Swiss-prot databases using the blast algorithm revealed the closest homolog to be the *B. subtilis* glpF gene (on DNA level) and the *B. subtilis* GlpF protein (on the protein level). The identity, on the DNA level, to the *B. subtilis* glpF coding region was 72.8%. The identity of the deduced GlpF protein to the *B. subtilis* GlpF protein was 79.3%.

The glpk coding region extends from pos. 1905 to pos. 3395 in SEQ ID NO:26. A search of EMBL and Swiss-prot databases using the blast program revealed the closest homolog to be the *B. subtilis* glpk gene (on the DNA level) and the *B. subtilis* GlpK protein (on the protein level). The identity, on the DNA level, to the *B. subtilis* glpK coding region was 75.6%. The identity of the deduced GlpK protein to the *B. subtilis* GlpK protein was 85.9%.

The glpD coding region extends from pos. 3542 to pos. 5209 in SEQ ID NO:26. A search of EMBL and Swiss-prot databases using the blast program revealed the closest homolog to be the *B. subtilis* glpD gene (on the DNA level) and the *B. subtilis* GlpD protein (on the protein level). The identity, on the DNA level, to the *B. subtilis* glpD coding region was 72.9%. The identity of the deduced GlpD protein to the *B. subtilis* GlpD protein was 81.9%.

The *B. licheniformis* region in addition contains a part of the yhxB gene, with the coding region starting at pos. 5394 and extending beyond the end of the sequenced fragment shown in SEQ ID NO:26.

Use of the glpD Gene for Directed Chromosomal Integration

In analogy with the strategy of the previous examples, segments of the glpD gene and the downstream region were PCR amplified from chromosomal DNA of *B. licheniformis*, and combined to provide vectors useful for, in a first step, deletion of the 3' end of the glpD gene, and, in a second step, restoration of the glpD gene and the simultaneous insertion of an expression cassette for a gene of interest into the chromosome.

An internal fragment of the glpD gene, denoted 'glpD', was PCR amplified using the two primers below, according to standard PCR protocol also described elsewhere herein.

5'-GACTGAATTCGCAATTTGAAGTGAAAATGGTAGC (SEQ ID NO:27), and

5'-GACTGGATCCAGATCTCATCTTTTCGGGAATC (SEQ ID NO:28).

The resulting fragment was purified and digested with EcoRI and BamHI, ligated to pUC19 digested with EcoRI and BamHI, and the ligation mixture transformed into *E. coli* SJ2 with selection for ampicillin resistance (200 µg/ml). A clone with the correct sequence was kept and denoted SJ5767 (SJ2/pSJ5767).

A fragment of DNA, derived from the *B. licheniformis* chromosome 55 to 555 basepairs downstream of the 3'-end of the glpD gene, was amplified using primers:

```
5'-GACTGAATTCAGATCTGCGGCCGCACGCGTAGTACTCCCGGCGTGAGGCTGTCTTG (SEQ ID NO:29) and

5'-GACTAAGCTTCAGTTACGCTCAAACACGTACG                         (SEQ ID NO:30).
```

The resulting fragment was purified and digested with EcoRI and HindIII, ligated to pUC19 digested with EcoRI and HindIII, and the ligation mixture transformed into *E. coli* SJ2 selecting ampicillin resistance (200 µg/ml). A clone with the correct sequence was kept as SJ5789 (SJ2/pSJ5789).

The internal fragment of the glpD gene was then combined with a spectinomycin resistance gene, flanked by resolvase sites, by excision of a 1.5 kb BcII-BamHI fragment from pSJ3358 and insertion of this into pSJ5767 which had been digested with BglII. The ligation mixture was transformed into *E. coli* SJ2 selecting ampicillin (200 µg/ml) and spectinomycin (120 µg/ml) resistance. A clone with the correct sequence was kept and denoted SJ5779 (SJ2/pSJ5779).

To construct the final plasmid for deletion of the 3'-end of glpD in the *B. licheniformis* chromosome, pSJ5789 is digested with HindIII and BglII, and the 0.5 kb fragment is ligated to the 5.5 kb HindIII-BglII fragment of pSJ2739. The ligation mixture is transformed into *B. subtilis* DN1885, selecting for erythromycin resistance (5 μg/ml) at 30° C. The resulting plasmid is digested with EcoRI and BglII, the 4.8 kb fragment is ligated to the 2.4 kb EcoRI-BamHI fragment excised from pSJ5779, and the ligation mixture is transformed into *B. subtilis* DN1885 selecting for erythromycin resistance (5 μg/ml) and spectinomycin resistance (120 μg/ml) at 30° C.

The deletion plasmid is transferred into *B. licheniformis* by use of the *B. subtilis* conjugation donor strain PP289-5, as described in previous examples, and the deletion is transferred to the chromosome using essentially the same procedures as described in previous examples.

The resulting glpD deletion strain is tested for growth on TSS minimal medium agar plates with glycerol as the sole carbon source.

The integration plasmid was designed to be able to repair the chromosomal glpD gene by homologous recombination, and carries a fragment containing the complete 3'-end of the glpD gene. It was useful to remove a BglII site present within the glpD gene by site-specific mutation designed to retain the amino acid sequence of the GlpD protein. This mutation was introduced by PCR, as follows.

An internal fragment of the glpD gene was amplified using primers SEQ ID NO:27 and SEQ ID NO:28.

The 3-'end of the glpD gene was amplified using primers

```
5'-CCGAGATTTCCCGAAAAGATGAAATTTGGACTTCTGAATCCGGACTG      (SEQ ID NO:31), and

5'-GACTAAGCTTAGATCTGCTAGCATCGATTGATTATTAACGAAAATTCACC   (SEQ ID NO:32).
```

The two amplified fragments were mixed, and the mixture used as template for a PCR amplification using primers SEQ ID NO:27 and SEQ ID NO:32.

```
5'-GACTAAGCTTGTGAAGGAGATGGAACATGAG                              (SEQ ID NO:33), and 5'-GACTGGATCCAGATCTGCGGCCGCACGCGTCGACAGTACTATTTTTAGTTCCAGTATTTT  (SEQ ID NO:34).
TTCC
```

The resulting fragment was digested with EcoRI and HindIII, ligated to EcoRI and HindIII digested pUC19, and the ligation mixture transformed into *E. coli* SJ2 selecting ampicillin resistance (200 μg/ml). A clone with the correct sequence was identified and designated SJ5775 (SJ2/pSJ5775).

To construct the final integration vector plasmid, pSJ5789 is digested with HindIII and BglII, and the 0.5 kb fragment is ligated to the 5.5 kb HindIII-BglII fragment of pSJ2739. The ligation mixture is transformed into *B. subtilis* DN1885, selecting for erythromycin resistance (5 μg/ml) at 30° C. The resulting plasmid is digested with EcoRI and BglII, ligated to the 1.5 kb BglII-EcoRI fragment excised from pSJ5775, and the ligation mixture is transformed into *B. subtilis* DN1885 selecting for erythromycin resistance (5 μg/ml) at 30° C.

This integration vector plasmid has a number of restriction enzyme sites immediately downstream from the 3'-end of the glpD gene, into which an expression cassette is inserted.

The resulting integration plasmid is transferred into the *B. licheniformis* glpD deletion strain by use of the *B. subtilis* conjugation donor strain PP289-5, as described in previous examples.

Cells, in which the integration plasmid has integrated into the chromosome via the glpD sequences are isolated by their ability to grow on glycerol minimal media plates at 50° C. Such cells are used as a starting point for isolation of a strain, which by a second recombination event has lost the integrated plasmid, but has retained the repaired version of the glpD gene, together with the expression cassette on the chromosome.

The procedure for obtaining such a strain is equivalent to the procedure described in previous examples used to isolate strains with an expression cassette integrated at the xylose isomerase region of the chromosome.

Use of the glpFK Genes for Directed Chromosomal Integration

In analogy with the strategy of the previous examples, segments of the glpF gene and the upstream glpP region were PCR amplified from chromosomal DNA of *B. licheniformis*, and combined to provide vectors useful for, in a first step, deletion of the promoter and 5' end of the glpF gene, and, in a second step, restoration of the promoter and glpF gene and the simultaneous insertion of an expression cassette for a gene of interest into the chromosome, upstream of the glpF promoter. Deletion of the glpF promoter is expected to abolish expression of the glpF gene and the downstream glpk gene. PCR amplifications were performed as previously described.

A DNA fragment containing the glpP gene was amplified using primers

The resulting fragment was purified and digested with HindIII and BamHI, ligated to HindIII and BamHI digested pUC19, and the ligation mixture transformed into *E. coli* SJ2 selecting ampicillin resistance (200 μg/ml). A correct clone kept was SJ5753 (SJ2/pSJ5753).

A DNA fragment containing most of the glpF gene, but lacking the first 160 basepairs of the coding sequence, was amplified using primers 5'-GAGCTCTAGATCTTCGGCGGCATCAGCGGAGC (SEQ ID NO:35), and

5'-GACTGAATTCCTTTTGCGCAATATGGAC (SEQ ID NO:36).

The resulting fragment was digested with XbaI and EcoRI, ligated to XbaI and EcoRI digested pUC19, and the ligation mixture transformed into *E. coli* SJ2 selecting ampicillin resistance (200 μg/ml). A correct clone was kept as SJ5765 (SJ2/pSJ5765).

In order to construct a plasmid useful for the deletion of the promoter and 5'-end of the glpF gene, the glpP containing fragment is excised from pSJ5753 as a HindIII-BglII fragment, the glpF fragment is excised from pSJ5765 as a BglII-EcoRI fragment, and these fragments ligated to the HindIII-EcoRI fragment of pSJ2739. The ligation mixture is transformed into *B. subtilis* DN1885, selecting for erythromycin resistance (5 µg/ml) at 30° C.

The resulting plasmid is digested with BglII, and ligated to a 1.5 kb BclI-BamHI fragment from pSJ3358, containing a spectinomycin resistance gene flanked by resolvase recognition sites. The ligation mixture is transformed into *B. subtilis* DN1885 selecting erythromycin resistance (5 µg/ml) and spectinomycin resistance (120 µg/ml) at 30° C.

The deletion plasmid thus constructed is transferred into *B. licheniformis* by use of the *B. subtilis* conjugation donor strain PP289-5, as described in previous examples, and the deletion is transferred to the chromosome using essentially the same procedures as described in previous examples.

The resulting glpF deletion strain is tested for growth on TSS minimal medium agar plates with glycerol as the sole carbon source.

The integration plasmid is designed to be able to repair the glpFK gene region by homologous recombination, and carries the glpF promoter and intact glpF gene. This fragment is amplified from chromosomal *B. licheniformis* DNA using primers: SEQ ID NO:36 and glycerol-3-phosphate. This inserts a copy of the expression cassette next to the glpD gene.

In a second step, another copy of the expression cassette can be inserted between the glpP and glpF genes using the integration vector designed to repair the glpF gene, and selecting for proper integration using growth on minimal media with glycerol.

If the two expression cassettes are identical (or strongly homologous, or containing homologous regions), it may be advantageous to insert these expression cassettes into the vector plasmids in such an orientation, that they in the final strain would be integrated in opposite orientation relative to each other, thus preventing their loss from the strain by homologous recombination under conditions in which there is no selection for growth on glycerol.

Example 5

In this work we did a homology study on the *Bacillus subtilis* genome and a second particular region of the *B. licheniformis* chromosome (SEQ ID NO:38), and we found that the region contains the 3'-end of the abnA gene, and the 5'-end of the araA gene of *B. licheniformis*. The size of the analyzed region is 1500 nucleotides, and the DNA sequence is shown in SEQ ID NO:38.

5'-GAGCTCTAGATCTGCTAGCATCGATCCGCGGTTAAAATGTGAAAAATTATTGACAACG (SEQ ID NO:37).

The resulting fragment is digested with XbaI and EcoRI, ligated to pUC19 digested with XbaI and EcoRI, and the ligation mixture transformed into *E. coli* SJ2 selecting ampicillin resistance (200 µg/ml). The amplified fragment is subsequently excised from this plasmid as a BglII-EcoRI fragment, which is ligated to the glpP containing fragment which is excised from pSJ5753 as a HindIII-BglII fragment, and to the HindIII-EcoRI fragment of pSJ2739. The ligation mixture is transformed into *B. subtilis* DN1885, selecting for erythromycin resistance (5 µg/ml) at 30° C. An expression cassette of interest is subsequently inserted into the linker region between the end of the glpP gene and the glpF promoter.

The resulting integration plasmid is transferred into the *B. licheniformis* glpF deletion strain by use of the *B. subtilis* conjugation donor strain PP289-5, as described in previous examples.

Colonies, in which the integration plasmid has integrated into the chromosome via the glpF sequences are isolated by their ability to grow on glycerol minimal media plates at 50° C. Such colonies are used as starting point for isolation of strains, which by a second recombination event has lost the integrated plasmid, but has retained the repaired version of the glpF gene, together with the expression cassette.

The procedure for obtaining such strains is equivalent to the previously described procedure to isolate strains with an expression cassette integrated at the xylose isomerase region of the chromosome.

Sequential Use of glpD and glpFK for Chromosomal Integration

This procedure envisages use of a strain having both the glpD gene deletion, and the glpF gene deletion, as the starting strain, and takes advantage of the ability of a strain, which is unable to express the glpK gene product, to grow on minimal media supplemented with glycerol-3-phosphate, whereas the strain deficient in glpD is unable to grow on this substrate.

The procedure is then to first introduce the integration plasmid designed to repair the glpD gene, and to select for proper integration using growth on minimal media with The 3'-end of the abnA coding region extends from position 1 to position 592 in SEQ ID NO:38. A search of EMBL and Swiss-prot databases using the blast program revealed the closest homolog to be the *B. subtilis* abnA gene (on the DNA level) and the *B. subtilis* AbnA protein (on the protein level). The identity, on the DNA level, to the corresponding *B. subtilis* abnA coding region was 68.9%. The identity of the deduced AbnA protein fragment to the corresponding *B. subtilis* AbnA protein fragment was 75.8%.

The 5'-end of the araA coding region extends from position 859 to position 1500 in SEQ ID NO:38. A search of EMBL and Swiss-prot databases using the blast program revealed the closest homolog to be the *B. subtilis* araA gene (on the DNA level) and *Bacillus* AraA proteins (on the protein level). The identity, on the DNA level, to the corresponding *B. subtilis* araA coding region was 68.2%. The identity of the deduced AraA protein fragment to the corresponding *B. subtilis* AraA protein fragment was 62.6%. The highest identity, scored in an alignment to a *Bacillus stearothermophilus* AraA protein fragment, was 68.4%.

Use of the araA Gene for Directed Chromosomal Integration

In analogy with the strategy of the previous examples, segments of the araA gene and the upstream abnA region were PCR amplified from chromosomal DNA of *B. licheniformis*, and combined to provide vectors useful for, in a first step, deletion of the promoter and 5' end of the araA gene, and, in a second step, restoration of the promoter and araA gene and the simultaneous insertion of an expression cassette for a gene of interest into the chromosome, upstream of the araA promoter. PCR amplifications were performed as previously described.

A fragment of the abnA gene upstream of araA was amplified using primers:

```
5'-GACTAAGCTTCATCCGGCGATCAGTTTAATGC        (SEQ ID NO:39), and

5'-GACTGAATTCAGATCTGCGGCCGCACGCGTCGACAGTACTATTTTTTTTTGACAG    (SEQ ID NO:40).
ATTTCAGAAC
```

The resulting fragment was digested with HindIII and EcoRI, ligated to HindIII and EcoRI digested pUC19, the ligation mixture transformed into E. coli SJ2 selecting ampicillin resistance (200 µg/ml), and a correct transformant kept as SJ5751 (SJ2/pSJ5751).

A fragment containing an internal part of the araA gene was amplified using primers:

5'-GACTGGATCCAGATCTAGTCGAGTACAAAGCGGTGGC (SEQ ID NO:41), and

5'-GACTGAATTCGACCAGCCAAGCTGAATCTGC (SEQ ID NO:42).

The resulting fragment was digested with BamHI and EcoRI, ligated to BamHI and EcoRI digested pUC19, the ligation mixture transformed into E. coli SJ2 selecting ampicillin resistance (200 µg/ml), and a correct transformant kept as SJ5752 (SJ2/pSJ5760).

The abnA gene fragment was excised from pSJ5751 as a HindIII-BglII fragment, ligated to the 5.5 kb HindIII-BglII fragment of pSJ2739, and the ligation mixture transformed into B. subtilis DN1885, selecting for erythromycin resistance (5 µg/ml) at 30° C. A transformant kept was SJ5756 (DN1885/pSJ5756).

Plasmid pSJ5760 was digested with BglII, and a 1.5 kb BamHI-BclI fragment from pSJ3358, containing a spectinomycin resistance gene flanked by resolvase recognition sites, was inserted. A clone was kept as SJ5777 (SJ2/pSJ5777).

The final deletion plasmid was constructed by excision of the araA-res-spc-res fragment from pSJ5777 as a EcoRI-BamHI fragment, and ligation of this to the large EcoRI-BglII fragment of pSJ5756. The ligation mixture was transformed into B. subtilis DN1885, selecting erythromycin resistance (5 µg/ml) and spectinomycin resistance (120 µg/ml) at 30° C. A correct transformant kept was SJ5803 (SJ2/pSJ5803).

The deletion plasmid pSJ5803 is transferred into B. licheniformis by use of the B. subtilis conjugation donor strain PP289-5, as described in previous examples, and the deletion is transferred to the chromosome using essentially the same procedures as described in previous examples.

The resulting araA deletion strain is tested for growth on TSS minimal medium agar plates with arabinose as the sole carbon source.

An integration vector plasmid is designed to be able to repair the araA gene region by homologous recombination, and carries the araA promoter and the 5'-end of the araA gene in addition to the abnA gene fragment of pSJ5756. The araA promoter fragment is amplified from chromosomal B. licheniformis DNA using primers synthesized based on the sequence given as SEQ ID NO:26. The plasmid is constructed, so that an expression cassette for a gene of interest can be inserted downstream from the abnA gene, but upstream of the araA promoter.

The resulting integration plasmid is transferred into the B. licheniformis araA deletion strain by use of the B. subtilis conjugation donor strain PP289-5, as described in previous examples. Colonies, in which the integration plasmid has integrated into the chromosome via the araA sequences are isolated by their ability to grow on arabinose minimal media plates at 50° C. Such colonies are used as starting point for isolation of strains, which by a second recombination event has lost the integrated plasmid, but has retained the repaired version of the araA gene, together with the expression cassette.

The procedure for obtaining such strains is equivalent to the previously described procedure to isolate strains with an expression cassette integrated at the xylose isomerase region of the chromosome.

Example 6

In this work we did a homology study on the Bacillus subtilis genome and a third particular region of the B. licheniformis chromosome (SEQ ID NO:42), and we found that the B. licheniformis region contains the 3'-end of the ispA gene and the metC gene. The size of the analyzed region is 4078 nucleotides, and the DNA sequence is shown in SEQ ID NO:42.

The 3'-end of the ispA coding region extends from pos. 1 to pos. 647 in SEQ ID NO:42. A BLAST search of the EMBL and Swiss-prot databases using this particular sequence revealed the closest homologue (on the DNA level) to be the B. subtilis ispA gene and (on the protein level) the B. subtilis IspA protein. The identity, on the DNA level, to the corresponding B. subtilis ispA coding region was 72.6% in an alignment constructed using the AlignX™ program in the Vector NTI™ 6.0 program package (Informax™, Inc.). The identity of the deduced IspA protein fragment to the corresponding B. subtilis IspA protein fragment was 82.3%.

The metC coding region extends from pos. 1121 to pos. 3406 in SEQ ID NO:42. A BLAST search of EMBL and Swiss-prot databases using this particular sequence revealed the closest homologue to be the B. subtilis metC gene (on the DNA level) and the B. subtilis MetC protein (on the protein level). The identity, on the DNA level, to the B. subtilis metC coding region was 72.6%. The identity of the deduced MetC protein to the B. subtilis MetC protein was 84.6%.

Use of the metC Gene for Directed Chromosomal Integration

Segments of the metC gene and the downstream region were PCR amplified from chromosomal DNA of B. licheniformis, and combined to provide a vector useful for deletion of the 3' end of the metC gene.

A fragment of DNA, derived from the B. licheniformis chromosome, 4 to 671 basepairs downstream of the 3'-end of the metC gene, was amplified using primers:

5'-AAAAAACCCGAGTTTCACAAAAATCCAC-TACAAACGCCGCC (SEQ ID NO:44), and

5'-TTTTTTTTAAGCTTATGCCGCATGTTCCTTGCTGTTTTCAC (SEQ ID NO:45).

The resulting fragment was digested with AvaI and HindIII, ligated to pMOL1887 digested with AvaI and HindIII, and the ligation mixture transformed into B. subtilis PL1801 with selection for erythromycin (5 µg/ml) and kanamycin (10 µg/ml) at 30° C. One clone was kept as CLO57 (PL1801/pCLO57).

An internal fragment of the metC gene, derived from the B. licheniformis chromosome, 247 to 754 basepairs into the metC open reading frame, was amplified using primers:

5'-AAAAAATCGATTCAGGGATATAAACGATCCG (SEQ ID NO:46), and

5'-TTTTTTTTTTCCATCGCACTGGGATAT-CAGCTCTTCATAAGCATC (SEQ ID NO:47).

The resulting fragment was digested with ClaI and BstXI, ligated to pCLO57 digested with ClaI and BstXI, and the ligation mixture transformed into B. subtilis PL1801 with selection for erythromycin (5 μg/ml) and kanamycin (10 μg/ml) at 30° C. One clone was kept as CLO58 (PL1801/pCLO58).

The resulting deletion plasmid pCLO58 has a cassette consisting of the internal metC fragment followed by the kanamycin resistance gene flanked by resolvase sites, which finally is followed by the DNA fragment downstream of the metC gene. The deletion plasmid pCLO58 was transferred to the conjugation donor strain PP1060-1, which is isogen to PP289-5 that previously has been described, except that the gene encoding green flourescent protein (GFP) has been integrated onto the chromosome. The resulting strain CLO71 (PP1060-1/pCLO58) was selected for erythromycin resistance at 30° C. The donor strain CLO71 was mated with the B. licheniformis recipient SJ3047, selecting conjugants for erythromycin resistance and a dal+ phenotype at 30° C.

One conjugant CLO74 was streaked on kanamycine (20 μg/ml) selecting for cells having plasmids integrated into the chromosome. Plating a resulting strain CLO78 onto SMS-glucose minimal plates revealed that the plasmid had integrated in the internal part of the metC gene resulting in a requirement for methionine. CLO78 was used as a starting point for isolation of strains, which by a second recombination event had lost the integrated plasmid, but had retained the deleted version of the metC gene.

Such a strain, denoted, CLO80 is appropriate to be used as a recipient for a plasmid carrying a cassette, which can be directed for integration at the metC locus essentially as described in previous examples, under conditions selective for an intact metC gene.

Example 7

In this work we did a homology study on the Bacillus subtilis genome and a fourth particular region of the B. licheniformis chromosome (SEQ ID NO:48), and we found that the B. licheniformis region contains the 3'-end of the spoVAF gene and the lysA gene. The size of the analyzed region is 3952 nucleotides, and the DNA sequence is shown in SEQ ID NO:48.

The 3'-end of the spoVAF coding region extends from pos. 1 to pos. 310 in SEQ ID NO:42. The identity, on the DNA level to the B. subtilis spoVAF coding region was 62.7%. The identity of the deduced SpoVAF protein to the B. subtilis SpoVAF protein was 55.2%.

The lysA coding region extends from pos. 1048 to pos. 2367 in SEQ ID NO:48. A BLAST search of EMBL and Swiss-prot databases using this particular sequence revealed the closest homologue to be the B. subtilis lysA gene (on the DNA level) and the B. subtilis LysA protein (on the protein level). The identity, on the DNA level, to the B. subtilis lysA coding region was 73.0%. The identity of the deduced LysA protein to the B. subtilis LysA protein was 82.2%.

Use of the lysA Gene for Directed Chromosomal Integration

In analogy with the strategy of the previous examples herein, segments of the lysA gene is PCR amplified from chromosomal DNA of B. licheniformis, and combined to provide vectors useful for, in a first step, partial deletion of the lysA gene, rendering a cell auxotrophic for lysine, and, in a second step, restoration of the lysA gene and the simultaneous insertion of an expression cassette for a gene of interest into the chromosome. Based on the strategies of the previous examples it is well within the skilled persons knowledge to determine the necessary primers and selective conditions for performing this procedure.

General Materials and Methods

In vitro DNA work, transformation of bacterial strains etc. were performed using standard methods of molecular biology (Maniatis, T., Fritsch, E. F., Sambrook, J. "Molecular Cloning. A laboratory manual". Cold Spring Harbor Laboratories, 1982; Ausubel, F. M., et al. (eds.) "Current Protocols in Molecular Biology". John Wiley and Sons, 1995; Harwood, C. R., and Cutting, S. M. (eds.) "Molecular Biological Methods for Bacillus". John Wiley and Sons, 1990).

If not otherwise mentioned, enzymes for DNA manipulations were used according to the specifications of the suppliers. Media used (TY, BPX and LB agar) have been described in EP 0 506 780.

Amylase activity was determined with the Phadebas$^R$ Amylase Test from Pharmacia & Upjohn as described by the supplier.

The use of a resistance gene, e.g. spectinomycin resistance or kanamycin resistance, flanked by recognition sites for a site specific recombination enzyme (res sites recognized by Resolvase from plasmid pAMbeta1) for easy deletion, has been described in U.S. Pat. No. 5,882,888. In the same patent are described plasmid pSJ3358, and strain B. subtilis PP289-5.

pUC19 is described in Yanisch-Perron, C., Vieira, J., Messing, J. (1985) Improved M13 phage cloning vectors and host strains: nucleotide sequences of the M13 mp18 and pUC19 vectors. Gene 33, 103–119.

pE194 is described in Horinouchi, S., and Weisblum, B. (1982). Nucleotide sequence and functional map of pE194, a plasmid that specifies inducible resistance to macrolide, lincosamide, and streptogramin type B antibiotics. J. Bacteriol., 150, 804–814.

Plasmid pSJ2739 is described in U.S. Pat. No. 6,100,063.

Plasmid pMOL1642 is shown in SEQ ID NO:49 and the following table:

| Feature | Basepairs | Reference |
|---|---|---|
| res-site | 5870 ... 6061 | EMBL: AF007787/4852 ... 4951 |
| Kan (R) | 6241 ... 162 | EMBL: SA110KAR/1390 ... 2151 |
| res-site | 203 ... 376 | EMBL: AF007787/4852 ... 4951 |
| Promoter PamyQ | 378 ... 396 | EMBL: A00607/67 ... 181 |
| prsA' | 492 ... 1008 | B. licheniformis |
| Ery (R) | 1133 ... 1864 (compl.) | EMBL: SAE194/2857 ... 2004 |
| Pre | 2276 ... 3484 | EMBL: SAE194/join(3150 ... 3728, 1 ... 633 |
| repF | 4113 ... 4709 | EMBL: SAE194/1244 ... 1594 |
| oriT | 4805 ... 5368 | EMBL: PP110CG/1021 ... 1575 |
| ups prsA | 5375 ... 5869 | B. licheniformis |

Strains Escherichia coli SJ2 and Bacillus subtilis DN1885 are described in Diderichsen, B., Wedsted, U., Hedegaard, L., Jensen, B. R., Sjøholm, C. (1990). Cloning of aldB, which encodes acetolactate decarboxylase, an exoenzyme from Bacillus brevis. Journal of Bacteriology 172, 4315–4321.

*Bacillus subtilis* PL1801 is the *B. subtilis* DN1885 with disrupted apr and npr genes.

*Bacillus licheniformis* PL1980 is a strain of *B. licheniformis*, which was made unable to produce the alkaline protease by insertion of a chloramphenicol resistance gene into the alkaline protease gene.

*Bacillus subtilis* JA578 is a *B. subtilis* 168 spo, amyE with a repF expression cassette (SEQ ID NO:50) inserted downstream of the dal gene (EMBL:BSDAL, Accession# M16207) on the chromosome. The repF expression cassette shown in SEQ ID NO:50 comprises the maltogenic amylase promoter PamyM (position 1-181 in SEQ ID NO:50) from *Bacillus Stearotermophilus* (EMBL:BSAMYL02, Accession #M36539), a linker (position 182-211 in SEQ ID NO:50) containing the RBS, fused to the the repF gene (position 212-808 in SEQ ID NO:50) from the plasmid pE194 (EMBL:PPCG2, accession #J01755), with the RepF start-codon in position 212 and Stop-codon in position 809 of SEQ ID NO:50.

*Bacillus subtilis* JA691 is *B. subtilis* JA578 dal⁻.

What is claimed is:

1. A method for producing a protein, comprising:
    (a) culturing a bacterial host cell comprising at least two copies of the gene encoding the protein stably integrated into the chromosome in different positions, wherein at least one DNA construct is integrated into a non-functional conditionally essential chromosomal gene(s) of the bacterial host, wherein the DNA construct comprises:
        (i) a non-functional copy of the conditionally essential gene(s); and
        (ii) at least one copy of the gene encoding the protein located between the non-functional copy and a DNA fragment homologous to a DNA sequence located adjacent to the non-functional conditionally essential gene(s) of the chromosome;
    wherein a first recombination between the non-functional conditionally essential gene and the non-functional copy results in a functional conditionally essential gene(s) located on the chromosome, and wherein the bacterial host cell had a copy of the gene of interest in the chromosome prior to integration of the at least one DNA construct; and
    (b) recovering the protein.

2. The method of claim 1, wherein the host cell further comprises at least one additional DNA construct(s) integrated into at least one different non-functional conditionally essential chromosomal gene(s) of the host cell.

3. The method of claim 1, wherein the non-functional conditionally essential chromosomal gene(s) of the host cell are non-functional due to a partial deletion of the gene(s), or an introduction of one or more mutations in the gene(s).

4. The method of claim 1, wherein the DNA construct further comprises at least one marker gene located between the non-functional copy and the DNA fragment and wherein the at least one marker gene is located between nucleotide sequences that are recognized by a resolvase.

5. The method of claim 4, wherein the at least one marker gene is excised from the chromosome by the resolvase.

6. The method of claim 1, wherein the host cell is a *Bacillus* host cell.

7. The method of claim 6, wherein the host cell is a *Bacillus licheniformis* host cell.

8. The method of claim 1, wherein a second recombination between the DNA fragment and the DNA sequence located adjacent to the non-functional conditionally essential gene(s) occurs.

9. The method of claim 8, wherein the DNA construct further comprises at least one marker gene which is located in the construct so that it is removed from the chromosome by the second recombination.

10. The method of claim 9, wherein the at least one marker gene confers resistance to an antibiotic selected from the group consisting of chloramphenicol, kanamycin, ampicillin, erythromycin, spectinomycin and tetracycline.

11. A method for producing a bacterial host cell comprising at least two copies of a gene of interest stably integrated into the chromosome at different positions, comprising;
  (a) introducing a DNA construct into the bacterial host cell, wherein the host cell comprises at least one chromosomal copy of the gene of interest and one or more non-functional conditionally essential chromosomal gene(s), and wherein the DNA construct comprises:
    (I) a non-functional copy of the conditionally essential gene(s); and
    (II) at least one copy of the gene of interest located between the non-functional copy and a DNA fragment homologous to a DNA sequence located adjacent to the non-functional conditionally essential gene(s) of the chromosome; p1 wherein a first recombination between the non-functional conditionally essential gene and the non-functional copy results in a functional conditionally essential gene(s) located on the chromosome, whereby a bacterial host cell comprising at least two copies of a gene of interest stably integrated into the chromosome at different positions is produced.

12. The method of claim 11, further comprising integrating at least one additional DNA construct(s) into at least one different non-functional conditionally essential chromosomal gene(s) of the host cell.

13. The method of claim 11, wherein the non-functional conditionally essential chromosomal gene(s) of the host cell are non-functional due to a partial deletion of the gene(s), or an introduction of one or more mutations in the gene(s).

14. The method of claim 11, wherein the DNA construct further comprises at least one marker gene located between the non-functional copy and the DNA fragment, and wherein the at least one marker gene is located between nucleotide sequences that are recognized by a resolvase.

15. The method of claim 14, further comprising the excission of the at least one marker gene from the chromosome by the resolvase.

16. The method of claim 11, wherein the host cell is a *Bacillus* host cell.

17. The method of claim 16, wherein the host cell is a *Bacillus licheniformis* host cell.

18. The method of claim 11, further comprising a second recombination between the DNA fragment and the DNA sequence located adjacent to the non-functional conditionally essential gene(s).

19. The method of claim 18, wherein the DNA construct further comprises at least one marker gene which is located in the construct so that it is removed from the chromosome by the second recombination.

20. The method of claim 19, wherein the at least one marker gene confers resistance to an antibiotic selected from the group consisting of chloramphenicol, kanamycin, ampicillin, erythromycin, spectinomycin and tetracycline.

21. A host cell produced by the method of claim 11.

* * * * *

SEQUENCE LISTING

```
<160> NUMBER OF SEQ ID NOS: 50

<210> SEQ ID NO 1
<211> LENGTH: 30
<212> TYPE: DNA
<213> ORGANISM: Artificial Sequence
<220> FEATURE:
<223> OTHER INFORMATION: Primer

<400> SEQUENCE: 1
gactaagctt ctgcatagtg agagaagacg                                         30

<210> SEQ ID NO 2
<211> LENGTH: 67
<212> TYPE: DNA
<213> ORGANISM: Artificial Sequence
<220> FEATURE:
<223> OTHER INFORMATION: Primer

<400> SEQUENCE: 2
gactgaattc agatctgcgg ccgcacgcgt gtcgacagta ctgaaataga ggaaaaaata      60
agttttc                                                                 67

<210> SEQ ID NO 3
<211> LENGTH: 33
<212> TYPE: DNA
<213> ORGANISM: Artificial Sequence
<220> FEATURE:
<223> OTHER INFORMATION: Primer

<400> SEQUENCE: 3
gactgaattc cgtatccatt cctgcgatat gag                                    33

<210> SEQ ID NO 4
<211> LENGTH: 41
<212> TYPE: DNA
<213> ORGANISM: Artificial Sequence
<220> FEATURE:
<223> OTHER INFORMATION: Primer

<400> SEQUENCE: 4
gactggatcc agatcttatt acaaccctga tgaatttgtc g                           41

<210> SEQ ID NO 5
<211> LENGTH: 60
<212> TYPE: DNA
<213> ORGANISM: Artificial Sequence
<220> FEATURE:
<223> OTHER INFORMATION: Primer

<400> SEQUENCE: 5
gactggatcc agatctgcta gcatcgatcc gcggctattt ccattgaaag cgattaattg      60
```

```
<210> SEQ ID NO 6
<211> LENGTH: 31
<212> TYPE: DNA
<213> ORGANISM: Artificial Sequence
<220> FEATURE:
<223> OTHER INFORMATION: Primer

<400> SEQUENCE: 6
tatttcccga gattctgtta tcgactcgct c                          31

<210> SEQ ID NO 7
<211> LENGTH: 27
<212> TYPE: DNA
<213> ORGANISM: Artificial Sequence
<220> FEATURE:
<223> OTHER INFORMATION: Primer

<400> SEQUENCE: 7
gttttcggcc gctgtccgtt cgtcttt                               27

<210> SEQ ID NO 8
<211> LENGTH: 27
<212> TYPE: DNA
<213> ORGANISM: Artificial Sequence
<220> FEATURE:
<223> OTHER INFORMATION: Primer

<400> SEQUENCE: 8
gtgtgacgga taaggccgcc gtcattg                               27

<210> SEQ ID NO 9
<211> LENGTH: 28
<212> TYPE: DNA
<213> ORGANISM: Artificial Sequence
<220> FEATURE:
<223> OTHER INFORMATION: Primer

<400> SEQUENCE: 9
ctcttgtctc ggagcctgca ttttgggg                              28

<210> SEQ ID NO 10
<211> LENGTH: 26
<212> TYPE: DNA
<213> ORGANISM: Artificial Sequence
<220> FEATURE:
<223> OTHER INFORMATION: Primer

<400> SEQUENCE: 10
agcattattc ttcgaagtcg cattgg                                26

<210> SEQ ID NO 11
<211> LENGTH: 45
<212> TYPE: DNA
<213> ORGANISM: Artificial Sequence
<220> FEATURE:
<223> OTHER INFORMATION: Primer

<400> SEQUENCE: 11
ttaagatctt ttttatacaa ataggcttaa caataaagta aatcc            45

<210> SEQ ID NO 12
<211> LENGTH: 3342
<212> TYPE: DNA
<213> ORGANISM: Bacillus licheniformis
<220> FEATURE:
```

```
<221> NAME/KEY: CDS
<222> LOCATION: (1303)..(2469)
<223> OTHER INFORMATION:
<220> FEATURE:
<221> NAME/KEY: misc_feature
<222> LOCATION: (2685)..(2685)
<223> OTHER INFORMATION: n denotes an undetermined nucleotide

<400> SEQUENCE: 12
```

| | | | | | |
|---|---|---|---|---|---|
| gcgtaccgtt | aaagtcgaac | agcggtttct | tccttttttac | atccatggat | taaaaagggg | 60 |
| ttgaaaaaag | gtgagaaaaa | gctttgtttt | gcttttaacg | gggctgcatg | taatccttat | 120 |
| gctttctgcc | tgcggccaaa | aatcgcaaga | agatgttgtg | acggggctcg | acaagaaggc | 180 |
| aaaagaatac | acgtcctata | aggcaaaagc | gaaaatgacc | attgaaacgg | ggaatgaccc | 240 |
| gcaggagtac | aacgtggaaa | tctggcataa | aaaaccttct | ctttaccggg | tctatttgga | 300 |
| aaacccgaaa | aaagaccaga | gccaggtgat | cttgcgcaat | gaaaacggcg | tgtttgtttt | 360 |
| gactccgtcg | ctgaataaaa | gcttccgctt | tcacagcgac | tggcccaata | acagcagcca | 420 |
| ggtatactta | ttcgaatcgc | tcgtaaagga | tgtcaaaaat | gatggggaag | cttcttttc | 480 |
| cgcaaaggat | tcaaaataca | ttttttgaaac | gaaaacgaat | tatcagcata | atcagatgct | 540 |
| gccgactcag | gaaatcgttt | tccataaaaa | gaccatggct | ccttcatcgg | ttaaagtgat | 600 |
| ggataccgac | cgcaaaccga | tggtaaaggt | tgagtttaca | agctttgaat | tcgataagcc | 660 |
| gctcgataaa | gactcttttg | atgaaaagaa | aaatatgacg | ctgtctcaaa | ttgacgtagc | 720 |
| gacaagcgct | gacgtgtcag | actctttcgc | tgtcaaaacg | ccgctcgatg | tgcctcaggg | 780 |
| cgtgaaaaag | cttgaagaga | aagagatggc | gactgaagac | ggcaaacgga | tcgtcatcac | 840 |
| atatggcggt | gaaaaatcct | ttacattgat | tcaggaaaaa | gcccgcgtcg | ccaaaacatc | 900 |
| cacttccgta | tccatgaacg | gagagcccgt | tgacctcggc | ttcacggtcg | gcgcactgac | 960 |
| ggataaatcg | ttgtcatgga | catatgacgg | agtcgattac | ttatctcat | cagaagatct | 1020 |
| ttctcaagat | gaacttctga | tggttgcaaa | aagcatgcag | ggacagtctt | cgaaatagac | 1080 |
| tgtgccgtat | ccggcagcct | gttttccgcc | cggaagcgga | aagcaggctt | ttttatattt | 1140 |
| gcgtcgcaag | cgtatgattt | cgacagcttt | tccgtaaaat | gtataccgtg | ccagcaattt | 1200 |
| ttctttttgtt | cagggctgat | gatcccgtgc | aaaatttccc | tttctccgaa | cttttagta | 1260 |
| tgatgggaag | gacgagtgaa | acaaggaaca | ggaagtgtca | tg atg agc tta aaa | | 1314 |

```
                                            Met Ser Leu Lys
                                              1
cca ttc tat aga aag aca tgg gcc gaa atc gat tta acg gct tta aaa    1362
Pro Phe Tyr Arg Lys Thr Trp Ala Glu Ile Asp Leu Thr Ala Leu Lys
 5              10                  15                  20
gaa aac gtc cgc aat atg aag cgg cac atc ggc gag cat gtc cgc ctg    1410
Glu Asn Val Arg Asn Met Lys Arg His Ile Gly Glu His Val Arg Leu
            25                  30                  35
atg gcc gtc gtt aaa gcg aat gcc tac gga cac ggg gat gca cag gta    1458
Met Ala Val Val Lys Ala Asn Ala Tyr Gly His Gly Asp Ala Gln Val
        40                  45                  50
gcg aag gcg gct ctt gca gaa ggg gcg tcc att ctt gct gtg gct tta    1506
Ala Lys Ala Ala Leu Ala Glu Gly Ala Ser Ile Leu Ala Val Ala Leu
    55                  60                  65
ttg gat gaa gcg ctt tcg ctg agg gcg cag ggg att gaa gaa ccg att    1554
Leu Asp Glu Ala Leu Ser Leu Arg Ala Gln Gly Ile Glu Glu Pro Ile
70                  75                  80
ctt gtc ctc ggt gca gtg ccg acc gaa tat gca agc att gcc gcg gaa    1602
Leu Val Leu Gly Ala Val Pro Thr Glu Tyr Ala Ser Ile Ala Ala Glu
85                  90                  95                 100
```

-continued

```
aag cgc att atc gtg act ggc tac tcc gtc ggc tgg ctg aaa gac gtg      1650
Lys Arg Ile Ile Val Thr Gly Tyr Ser Val Gly Trp Leu Lys Asp Val
            105                 110                 115 ctc ggt ttt ctg aat gag gcc gaa gct cct ctt gaa tat cat ttg aag      1698
Leu Gly Phe Leu Asn Glu Ala Glu Ala Pro Leu Glu Tyr His Leu Lys
            120                 125                 130 atc gac acg ggc atg ggc cgc ctt ggc tgc aaa acg gaa gaa gag atc      1746
Ile Asp Thr Gly Met Gly Arg Leu Gly Cys Lys Thr Glu Glu Glu Ile
            135                 140                 145 aaa gaa atg atg gag atg acc gaa tcg aac gat aag ctc aat tgt acg      1794
Lys Glu Met Met Glu Met Thr Glu Ser Asn Asp Lys Leu Asn Cys Thr
150                 155                 160 ggc gtg ttc act cat ttc gcc acg gcg gac gaa aag gac acc gat tat      1842
Gly Val Phe Thr His Phe Ala Thr Ala Asp Glu Lys Asp Thr Asp Tyr
165                 170                 175                 180 ttc aac atg cat ctt gac cgc ttt aaa gag ctg atc agc ccc ttc ccg      1890
Phe Asn Met His Leu Asp Arg Phe Lys Glu Leu Ile Ser Pro Phe Pro
                185                 190                 195 ctt gac cgt ttg atg gtg cat tcg tca aac agc gcc gcg ggt ctg cgc      1938
Leu Asp Arg Leu Met Val His Ser Ser Asn Ser Ala Ala Gly Leu Arg
            200                 205                 210 ttc agg gaa cag cta ttt aat gcc gtc cgc ttc ggc atc ggc atg tac      1986
Phe Arg Glu Gln Leu Phe Asn Ala Val Arg Phe Gly Ile Gly Met Tyr
            215                 220                 225 ggt ttg gcg ccg tca acc gaa ata aaa gac gag ctg ccg ttt cgt ctg      2034
Gly Leu Ala Pro Ser Thr Glu Ile Lys Asp Glu Leu Pro Phe Arg Leu
            230                 235                 240 cgg gaa gtg ttt tcg ctt cat acc gaa ctc acc cat gtg aaa aaa att      2082
Arg Glu Val Phe Ser Leu His Thr Glu Leu Thr His Val Lys Lys Ile
245                 250                 255                 260 aaa aaa ggc gag agc gtc agc tac ggg gcg aca tat aca gct cag cgc      2130
Lys Lys Gly Glu Ser Val Ser Tyr Gly Ala Thr Tyr Thr Ala Gln Arg
                265                 270                 275 gac gaa tgg atc ggg aca gtc ccc gtc ggg tat gcc gac gga tgg ctg      2178
Asp Glu Trp Ile Gly Thr Val Pro Val Gly Tyr Ala Asp Gly Trp Leu
            280                 285                 290 agg cgc ctg gcc gga acg gaa gtg ctg atc gac gga aaa cgc caa aaa      2226
Arg Arg Leu Ala Gly Thr Glu Val Leu Ile Asp Gly Lys Arg Gln Lys
            295                 300                 305 ata gca ggg aga atc tgc atg gac cag ttc atg att tcc ctt gcc gaa      2274
Ile Ala Gly Arg Ile Cys Met Asp Gln Phe Met Ile Ser Leu Ala Glu
            310                 315                 320 gaa tac cct gtc ggc aca aag gtt acc ttg atc gga aag caa aaa gac      2322
Glu Tyr Pro Val Gly Thr Lys Val Thr Leu Ile Gly Lys Gln Lys Asp
325                 330                 335                 340 gaa tgg atc tca gtc gac gaa atc gcc caa aat ttg cag acg atc aat      2370
Glu Trp Ile Ser Val Asp Glu Ile Ala Gln Asn Leu Gln Thr Ile Asn
                345                 350                 355 tat gaa att acc tgt atg ata agt tca agg gtg ccc cgt atg ttt ttg      2418
Tyr Glu Ile Thr Cys Met Ile Ser Ser Arg Val Pro Arg Met Phe Leu
            360                 365                 370 gaa aat ggg agt ata atg gaa ata agg aat ccg atc ttg cct gat caa      2466
Glu Asn Gly Ser Ile Met Glu Ile Arg Asn Pro Ile Leu Pro Asp Gln
            375                 380                 385 tcc tgaaaattga tgaattagcg gaaaaacaac tttgcttgcg aaaagaataa           2519
Ser tgatatgatt atgaatggaa tgatagagt gttgtatccg taagtttggt ggaggtgtat    2579 gttttttgtct gaatccagcg caacaactga atatattgatt cgcttgccag aagctttagt 2639
```

-continued

```
atcagaactg gatggtgtcg tcatgcgaga taaccgggag cagganatga actgatttta      2699
ccaagccaca aaaatgtagg aacgcgaacg caaaaaatcg acaaattcgg ggaatcgatg      2759
agaagcggtt atatggagat ggccaagatc caatttgaac atctcttctg aggctcaatt      2819
tgcagagtat gaggctgaaa acacagtaga gcgcttacta agcggatgat aatcatttga      2879
ttgttaaacg cggcgatgtt tattttgctg acctatctcc tgttgttggc tcagaacaag      2939
gcggggtgcg cccggtttta gtgattcaaa acaacatcgg caatcgcttc agcccaactg      2999
ctattgttgc agccataaca gcccaaatac agaaagcaaa attacctacc cacgtcgaaa      3059
ttgatgcgaa acgctacggt tttgaaagag actccgttat attgctcgaa caaattcgga      3119
cgattgacaa gcaaagatta acggacaaaa tcacccatct cgatgatgaa atgatggaaa      3179
aggtcaacga agccttacaa atcagtttgg cactcattga ttttttaatat tgatgaaagt      3239 tgctcgaggc gaaagagcaa ctttttttgt gttcaaaaat aacaatacga tataatggta      3299
actgttagtc ctaaaaatgt tagccagatg tagtcagggg gat                       3342
```

<210> SEQ ID NO 13
<211> LENGTH: 389
<212> TYPE: PRT
<213> ORGANISM: Bacillus licheniformis

<400> SEQUENCE: 13

```
Met Ser Leu Lys Pro Phe Tyr Arg Lys Thr Trp Ala Glu Ile Asp Leu
1               5                   10                  15

Thr Ala Leu Lys Glu Asn Val Arg Asn Met Lys Arg His Ile Gly Glu
            20                  25                  30

His Val Arg Leu Met Ala Val Val Lys Ala Asn Ala Tyr Gly His Gly
        35                  40                  45

Asp Ala Gln Val Ala Lys Ala Ala Leu Ala Glu Gly Ala Ser Ile Leu
    50                  55                  60

Ala Val Ala Leu Leu Asp Glu Ala Leu Ser Leu Arg Ala Gln Gly Ile
65                  70                  75                  80

Glu Glu Pro Ile Leu Val Leu Gly Ala Val Pro Thr Glu Tyr Ala Ser
                85                  90                  95

Ile Ala Ala Glu Lys Arg Ile Ile Val Thr Gly Tyr Ser Val Gly Trp
            100                 105                 110

Leu Lys Asp Val Leu Gly Phe Leu Asn Glu Ala Glu Ala Pro Leu Glu
        115                 120                 125

Tyr His Leu Lys Ile Asp Thr Gly Met Gly Arg Leu Gly Cys Lys Thr
    130                 135                 140

Glu Glu Glu Ile Lys Glu Met Met Glu Met Thr Glu Ser Asn Asp Lys
145                 150                 155                 160

Leu Asn Cys Thr Gly Val Phe Thr His Phe Ala Thr Ala Asp Glu Lys
                165                 170                 175

Asp Thr Asp Tyr Phe Asn Met His Leu Asp Arg Phe Lys Glu Leu Ile
            180                 185                 190

Ser Pro Phe Pro Leu Asp Arg Leu Met Val His Ser Ser Asn Ser Ala
        195                 200                 205

Ala Gly Leu Arg Phe Arg Glu Gln Leu Phe Asn Ala Val Arg Phe Gly
    210                 215                 220

Ile Gly Met Tyr Gly Leu Ala Pro Ser Thr Glu Ile Lys Asp Glu Leu
225                 230                 235                 240

Pro Phe Arg Leu Arg Glu Val Phe Ser Leu His Thr Glu Leu Thr His
```

-continued

```
                 245                 250                 255
Val Lys Lys Ile Lys Gly Glu Ser Val Ser Tyr Gly Ala Thr Tyr
            260                 265                 270
Thr Ala Gln Arg Asp Glu Trp Ile Gly Thr Val Pro Val Gly Tyr Ala
        275                 280                 285
Asp Gly Trp Leu Arg Arg Leu Ala Gly Thr Glu Val Leu Ile Asp Gly
        290                 295                 300
Lys Arg Gln Lys Ile Ala Gly Arg Ile Cys Met Asp Gln Phe Met Ile
305                 310                 315                 320
Ser Leu Ala Glu Glu Tyr Pro Val Gly Thr Lys Val Thr Leu Ile Gly
                325                 330                 335
Lys Gln Lys Asp Glu Trp Ile Ser Val Asp Glu Ile Ala Gln Asn Leu
            340                 345                 350
Gln Thr Ile Asn Tyr Glu Ile Thr Cys Met Ile Ser Ser Arg Val Pro
        355                 360                 365
Arg Met Phe Leu Glu Asn Gly Ser Ile Met Glu Ile Arg Asn Pro Ile
    370                 375                 380
Leu Pro Asp Gln Ser
385

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
gatgaacttc tgatggttgc                                              20

<210> SEQ ID NO 15
<211> LENGTH: 26
<212> TYPE: DNA
<213> ORGANISM: Artificial Sequence
<220> FEATURE:
<223> OTHER INFORMATION: Primer

<400> SEQUENCE: 15
aaaggatccc cctgactaca tctggc                                       26

<210> SEQ ID NO 16
<211> LENGTH: 39
<212> TYPE: DNA
<213> ORGANISM: Artificial Sequence
<220> FEATURE:
<223> OTHER INFORMATION: Primer

<400> SEQUENCE: 16
aaagcggccg cgagactgtg acggatgaat tgaaaaagc                         39

<210> SEQ ID NO 17
<211> LENGTH: 32
<212> TYPE: DNA
<213> ORGANISM: Artificial Sequence
<220> FEATURE:
<223> OTHER INFORMATION: Primer

<400> SEQUENCE: 17
aaagaattcg tgaaatcagc tggactaaaa gg                                32

<210> SEQ ID NO 18
```

```
<211> LENGTH: 32
<212> TYPE: DNA
<213> ORGANISM: Artificial Sequence
<220> FEATURE:
<223> OTHER INFORMATION: Primer

<400> SEQUENCE: 18
aaaggatccc gcaagcaaag ttgtttttcc gc                              32

<210> SEQ ID NO 19
<211> LENGTH: 30
<212> TYPE: DNA
<213> ORGANISM: Artificial Sequence
<220> FEATURE:
<223> OTHER INFORMATION: Primer

<400> SEQUENCE: 19
aaaggtaccg aaagacatgg gccgaaatcg                                 30

<210> SEQ ID NO 20
<211> LENGTH: 32
<212> TYPE: DNA
<213> ORGANISM: Artificial Sequence
<220> FEATURE:
<223> OTHER INFORMATION: Primer

<400> SEQUENCE: 20
aaaggtaccg gtaatgactc tctagcttga gg                              32

<210> SEQ ID NO 21
<211> LENGTH: 33
<212> TYPE: DNA
<213> ORGANISM: Artificial Sequence
<220> FEATURE:
<223> OTHER INFORMATION: Primer

<400> SEQUENCE: 21
caaatcgatc atcaccgaaa cgcggcaggc agc                             33

<210> SEQ ID NO 22
<211> LENGTH: 31
<212> TYPE: DNA
<213> ORGANISM: Artificial Sequence
<220> FEATURE:
<223> OTHER INFORMATION: Primer

<400> SEQUENCE: 22
attaagcttg atatgattat gaatggaatg g                               31

<210> SEQ ID NO 23
<211> LENGTH: 30
<212> TYPE: DNA
<213> ORGANISM: Artificial Sequence
<220> FEATURE:
<223> OTHER INFORMATION: Primer

<400> SEQUENCE: 23
aaagctagca tcccctgac tacatctggc                                  30

<210> SEQ ID NO 24
<211> LENGTH: 24
<212> TYPE: DNA
<213> ORGANISM: Artificial Sequence
<220> FEATURE:
<223> OTHER INFORMATION: Primer

<400> SEQUENCE: 24
```

```
gcgtaccgtt aaagtcgaac agcg                                           24

<210> SEQ ID NO 25
<211> LENGTH: 30
<212> TYPE: DNA
<213> ORGANISM: Artificial Sequence
<220> FEATURE:
<223> OTHER INFORMATION: Primer

<400> SEQUENCE: 25
aaagctagca tccccctgac tacatctggc                                     30

<210> SEQ ID NO 26
<211> LENGTH: 5761
<212> TYPE: DNA
<213> ORGANISM: Bacillus licheniformis

<400> SEQUENCE: 26
accggggccg gcgttttgt cggcaacgtc tgtatatttc agccttgaaa ggcccttgat      60
tccttcatgg atgatcgctt tcataaaaaa attcccccca ttcgagttgg ttgtgttaaa    120
ttatggacat gaatgaaggt aaatgtaaaa tgatttgccc ggggccgctt agaggccttc    180
tgttttataa aggattgcaa tgaggcgaaa attccattag tgtaatacag aagcaagcta    240
gcaagtgaag gagatggaac atgagttttc acgatcaaaa tatttacct gcggtacgca     300 atatgaagca gttcgataca ttcctggaca gccttttc atcggggtg ctgcttgaca       360 tccatcttgg acagctggga ggcgtgatca gcgcggcaag atcccatggg aaaaaaatgt    420
ttgttcacgt cgatctgatc caaggaatta agcatgatga atacggtgcg gaattcattt    480
gccaggaaat gaaaccggcg gcattctttt ctacgagatc aagcgttatc gccaaagcaa    540
agcagaagaa agtgtatgcg atccagcgca tgttttaat agacacaagc gccatgaaga    600
agagcattga attggtgaaa aagcacagac ccgactatat agaagtgctt cccggagtag    660
tgccggaatt gatcagggaa gtcaaagaaa taaccggcat tccgatcttt gcgggcgggt   720
ttatccgtac cgaaaaagac gtcgagcagg cgcttgcagc aggggcgtcc gcagtcacca    780
cctcagacac tgatttatgg aaaaaatact ggaactaaaa atttaaaatg tgaaaaatta    840
ttgacaacgc tttcactata cgatacgatc ttactaagtt aatacattgt gacgagacc    900 cggagaccac agcagttctt tactcagtat gatgtaaaga aagtttgctg tgttttttta    960
tggtctttta gacacagtgg agaaggtgaa cttatggcgt tcatctatta gaataatact   1020
tcataataga ttttaggagg gatagccttg acagcatttt gggggaagt tatcggaacg    1080 atgctgctca tcgtctttgg agctggagtt tgtgcaggag ttaatttgaa aaaatcgctg   1140
tcccatcaat ccggatggat tgtgatcgtc ttcggctggg gcttggcgt ggccatggcg    1200 gtatatgccg tcgcggcat cagcggagcg catttaaatc cggccgttac attgggctg    1260 gcatttgtcg gagattttcc ttgggaagaa gtgccttcat atattttggg acagatgatc   1320
ggcgcatttt taggagcggt gctcgttttt cttcactact tgccgcactg gaagaaacc   1380 gaggatcaag gcgcgaagct tggagtattt tcgacaggtc cggcgattcc aaatacatt    1440 gcaaacctgt tcagtgaaac attggggact tttattctcg ttctcggact tttaacgatc   1500
ggtgcaaaca agtttactga cggactgaat cctcttgttg tcggatttct gatcgtggcg   1560
atcggtatct cgctcggcgg aacaacaggc tatgcgatta accctgcccg cgatctgggg   1620
ccgagaattg cccattttgt ccttccgatt gcaggcaaag ggagttcaaa ctggaagtac   1680
```

-continued

| | |
|---|---|
| gcgtggatcc ctgttttagg accggcgctt ggcggttcat ttgcaggcgt tttttacaac | 1740 |
| gccgtattca aagggcatat cacaaacaca ttttggattg taagcgttat actagttgtg | 1800 |
| atattgttag gtttctatat tcatatgaaa aacaagcag ttgatcaatc ggtcaacatt | 1860 |
| taaaaaaag caatcttaac agacatataa gggggagttt caaaatggaa aagtacattt | 1920 |
| tgtctcttga tcaaggcacc acaagcacaa gggcgattgt tttcaacaaa gcaggcgaaa | 1980 |
| tcgtccatat tgcgcaaaag gaattccagc aatattttcc aaaccccggc tgggttgaac | 2040 |
| acaatgcaaa cgaaatctgg ggctctgttc tgtcggtgat cgcttcagcg ctttcagaat | 2100 |
| cggggatcga agccggacaa attgccgaa tcgggatcac aaaccagcgg gaaacgaccg | 2160 |
| tggtttggga taaacatacc ggcaaaccgg tctacaacgc gattgtgtgg cagtcccgcc | 2220 |
| aatcggctga gatatgccag gaattaaaag agaaaggcta tgaagagacg atcagagaaa | 2280 |
| aaacagggct tttaatcgat ccttattttt caggcacgaa agtgaaatgg atcctggatc | 2340 |
| atgtggaagg ggcaagggag aaagccgaaa acggcgacct tctcttcggt acgatcgatt | 2400 |
| cttggctgat ctggaaaatg tccggcggaa aagcgcatgt gacagattat tcaaacgcct | 2460 |
| caagaacatt gatgttcaac atctatgacc taaaatggga tgatgaactt ctcgatattc | 2520 |
| tcggcgtgcc gaaatcgatg gttccggaag tcaagccttc atcgcatgta tacgctgaaa | 2580 |
| cggtcgatta tcatttcttc ggcaaaaaca ttccgattgc aggtgcagcc ggcgaccagc | 2640 |
| aggcagcatt gttcgggcag gcttgctttg aagaaggaat ggttaagaac acgtatggaa | 2700 |
| caggctgctt tatgctgatg aacaccggcg agaaagcgat taaatcagag cacggcctgc | 2760 |
| tgacgacaat cgcttggggc atcgacggaa aggtggaata tgcgctggaa ggcagcgtct | 2820 |
| tcgtcgcggg ttccgctatt caatggctgc gtgatgggct gagaatgttt aaagacgcca | 2880 |
| aagaaagtga aaaatacgct gtaagagcag aatctgccga tggtgtttat gtggtccctg | 2940 |
| catttgtagg tttaggcacg ccttattggg acagcgatgt ccgcggcgct gtattcggac | 3000 |
| tgacccgggg tacgacgaaa gagcattta tcagagcaac gcttgaagcg cttgcctatc | 3060 |
| aaacgaaaga cgtgctggac gcaatgaagg aagactccgg gatcccggtt aaaacgctga | 3120 |
| gagtcgacgg cggagctgtc aaaaacaact tcctgatgga ttttcagggc gacattttag | 3180 |
| atgtccctgt agaacgtcct gaaatcaatg aaacaacagc gcttggttca gcctatttag | 3240 |
| cgggccttgc tgtcggcttc tggagcgatc gttccgagat caaagaccag tggcagcttg | 3300 |
| acaaacgttt tgaaccgaaa atggaagaaa aagagcgtga gagcctgtac aacgggtgga | 3360 |
| agaaagctgt aaatgcagct agggctttta aataagctgc atgtatgtta caatctaatt | 3420 |
| aagttaatag aaacggttgg agaagaggag agaccgcaga caccaaagca gtatcagcgc | 3480 |
| tttggatgtt tgtggtctct ttttctattt tttaccgtga caacaaggga ggacatgaaa | 3540 |
| catggaatca ttattttcaa gccgtaaacg ggacgacatt ttacagaata tgacgaagca | 3600 |
| gaagtatgac gtgtttatta tcggcggagg tattactggg gctgggacgg cattggatgc | 3660 |
| cgcatcgcgc ggaatgaaaa cggcgctttg cgaaatgcag actttgcag ccggaacgtc | 3720 |
| aagccgttcc acgaaacttg tacacggcgg gcttcgctat ttaaagcaat ttgaagtgaa | 3780 |
| aatggtagcc gaggtcggca agagcgggc gatcgtctat gaaaacgggc cgcacgttac | 3840 |
| aacgcccgaa tggatgctgc ttccgatgca taagggaggg actttcggca aattcagcac | 3900 |
| ttcaatcgga ctgagggtgt acgactttt ggcaggcgtc aaaaaagctg agcggaggag | 3960 |
| catgctgact gccgaagaaa cgcttcaaaa agagccgctc gtgaaaaaga acggcctgaa | 4020 |
| gggcggcggc tattatgtcg aataccggac ggatgatgcc agattgacga tcgaagtcat | 4080 |

```
gaaagaagcc gttaaattcg gagccgaggc cgtcaattat gcaaaagtaa gcgattttat    4140
atatgaaaac ggcaaggtca ccggcgtggt cattgaagac gtcttcacga aaaaaacgta    4200
ccgcgtctac gcgaaaaaaa ttgtcaatgc cgcggggccg tgggtcgacc gtctgcggga    4260
aaaagaccat tcaaaagaag gcaaacacct tcagcataca aaaggcgtgc atcttgtttt    4320
tgatcaatcg gtctttcctt aaaacaagc cgtttatttt gatacgcctg acggccgcat    4380
ggtgttcgcc attccgagag acggaaaggc atatgtcggc acaacagaca ccgtctacaa    4440
cgagaatttg gaacaccctc gaatgacgac agcagacagg gattatgtca tcaatgcaat    4500
caactatatg ttccctgaac ttggaatcaa agccgaagat gtcgaatcaa gctgggctgg    4560
cctcagaccg ctgattcatg aagaaggaaa agacccgtcc gagatttccc gaaaagatga    4620
gatctggact tctgaatccg gactgatcac gatcgccggc ggaaagctga caggctacag    4680
aaaaatggct gagcatatcg tcgatcttgt cagagaccga ttaaaagaag agggcgacag    4740
agacttcggg ccttgcagaa caaaaacgat gccgatttca ggcggccata tcggcggctc    4800
caaaaatctg gaggctttta ttcaagcgaa agcagccgaa gggattgagg ccggactgtc    4860
cgaagagacg gccaaacaaa tcgccgcacg atacggttcg aacgcagacc gcctgtttga    4920
tcgtattcca tcgctgaaag atgaagcagc aaaacgccgc atccctgtcc atgtactagc    4980
agaaatggat tacgggatcg aggaagaaat ggcagccgtc ccggcagact tcttcgtccg    5040
cagaaccggt gcgctgttct ttgacatcaa ttgggtccgc acttacaaag agagccttac    5100
ggactacatg agcgagaagc tgaactggga tggcgaaacg aaggcccggc atgtcaaggc    5160
attggaagga ctactacacg atgctgttgt cccgctggaa agcaaatgat ttattaggtc    5220
aaataacctt ggtgaatttt cgttaataat caatcgaatg gcccggcgtg aggctgtctt    5280
gaacaggcag cctcattttt ttcatttggc atgctaaatt tggacaaagc ggcggtttgt    5340
cgatatgata aaagaaaagc tgcaattact tagctagaac attggaggta atcatgagct    5400
ggagaacgag ctatgaacgc tggagaaaca aagaaaactt agattccgaa ttaaaagcgc    5460
ttcttttgga agcggaagga aatgaaaaag aactagagga ttgctttat aaaaaacttg    5520 agtttggtac agccggtatg cgcggtgaga tcggaccggg cccgaaccgc atgaacgttt    5580
atacggttcg caaagcatcg gcgggccttg ccgcatacat aggagcgaac ggcggcgaag    5640
caaaaaagcg cggcgttgtg atcgcgtacg attcccgcca caaatcgcct gaatttgcaa    5700
tggaagctgc taagacgctc gcagaaaacg gcgttcaaac gtacgtgttt gagcgtaact    5760
g                                                                  5761

<210> SEQ ID NO 27
<211> LENGTH: 34
<212> TYPE: DNA
<213> ORGANISM: Artificial Sequence
<220> FEATURE:
<223> OTHER INFORMATION: Primer

<400> SEQUENCE: 27
gactgaattc gcaatttgaa gtgaaaatgg tagc                                  34

<210> SEQ ID NO 28
<211> LENGTH: 33
<212> TYPE: DNA
<213> ORGANISM: Artificial Sequence
<220> FEATURE:
<223> OTHER INFORMATION: Primer
```

```
<400> SEQUENCE: 28
gactggatcc agatctcatc ttttcgggaa atc                          33

<210> SEQ ID NO 29
<211> LENGTH: 56
<212> TYPE: DNA
<213> ORGANISM: Artificial Sequence
<220> FEATURE:
<223> OTHER INFORMATION: Primer

<400> SEQUENCE: 29
gactgaattc agatctgcgg ccgcacgcgt agtactcccg gcgtgaggct gtcttg    56

<210> SEQ ID NO 30
<211> LENGTH: 32
<212> TYPE: DNA
<213> ORGANISM: Artificial Sequence
<220> FEATURE:
<223> OTHER INFORMATION: Primer

<400> SEQUENCE: 30
gactaagctt cagttacgct caaacacgta cg                           32

<210> SEQ ID NO 31
<211> LENGTH: 47
<212> TYPE: DNA
<213> ORGANISM: Artificial Sequence
<220> FEATURE:
<223> OTHER INFORMATION: Primer

<400> SEQUENCE: 31
ccgagatttc ccgaaaagat gaaatttgga cttctgaatc cggactg            47

<210> SEQ ID NO 32
<211> LENGTH: 50
<212> TYPE: DNA
<213> ORGANISM: Artificial Sequence
<220> FEATURE:
<223> OTHER INFORMATION: Primer

<400> SEQUENCE: 32
gactaagctt agatctgcta gcatcgattg attattaacg aaaattcacc         50

<210> SEQ ID NO 33
<211> LENGTH: 31
<212> TYPE: DNA
<213> ORGANISM: Artificial Sequence
<220> FEATURE:
<223> OTHER INFORMATION: Primer

<400> SEQUENCE: 33
gactaagctt gtgaaggaga tggaacatga g                             31

<210> SEQ ID NO 34
<211> LENGTH: 64
<212> TYPE: DNA
<213> ORGANISM: Artificial Sequence
<220> FEATURE:
<223> OTHER INFORMATION: Primer

<400> SEQUENCE: 34
gactggatcc agatctgcgg ccgcacgcgt cgacagtact attttttagtt ccagtatttt  60 ttcc                                                          64
```

```
<210> SEQ ID NO 35
<211> LENGTH: 32
<212> TYPE: DNA
<213> ORGANISM: Artificial Sequence
<220> FEATURE:
<223> OTHER INFORMATION: Primer

<400> SEQUENCE: 35
gagctctaga tcttcggcgg catcagcgga gc                                     32

<210> SEQ ID NO 36
<211> LENGTH: 28
<212> TYPE: DNA
<213> ORGANISM: Artificial Sequence
<220> FEATURE:
<223> OTHER INFORMATION: Primer

<400> SEQUENCE: 36
gactgaattc cttttgcgca atatggac                                          28

<210> SEQ ID NO 37
<211> LENGTH: 58
<212> TYPE: DNA
<213> ORGANISM: Artificial Sequence
<220> FEATURE:
<223> OTHER INFORMATION: Primer

<400> SEQUENCE: 37
gagctctaga tctgctagca tcgatccgcg gttaaaatgt gaaaaattat tgacaacg         58

<210> SEQ ID NO 38
<211> LENGTH: 1500
<212> TYPE: DNA
<213> ORGANISM: Bacillus licheniformis

<400> SEQUENCE: 38
atcagcgata gggctcgcat cgacagaccg gatttcatcc ggccaatggc gggatgacgg       60
gctggtcatc aggtcgacat ccggcgatca gtttaatgcc attgaccctg atctggtcat      120
tgacaaagac ggaaagccct ggctctcatt cggttccttc tggagcggca ttaagctgac      180
aaggcttgat aaaaacacga tgaaaccgac gggaagcctg tattcgatcg cctcaaggcc      240
gaataacgga ggagcggttg aagccccgaa cattacctac aaagacggct actattactt      300
atttgtctcg tttgacagct gctgcaaagg ggtggacagc acatataaaa tagcctatgg      360
ccgttcaacg agcattacgg gaccctatta tgataaaagc ggcaaaaata tgatgaacgg      420
cggagggacg atcctggact ccggcaatga ccgctggaaa gggccgggac atcaggatgt      480
tctgaacaac tcgatccttg tcaggcatgc ttacgacgcg ctggacaatg gtgtatcaaa      540
gctgctcatc aatgacttgt actgggattc ccaaggatgg ccgacttatt aacagcagat      600 gacggcggt ttccgcccgg ttttttttgt tctgaaatct gtcaaaaaaa aataaaaaac       660
ataccggaaa ttaaattgac agttttttc ataatgatat aatgaagttg ttcgtacaaa      720 tatgttttt atgttagttg tacgtacata taatcgcgat acagtttgag atcaaggtat      780
gatttatgtt ttttgtaag cgtttaata gttttgctatt ctacacagac accataaaga      840
cgaggaggag gaagctattt gattcaggca aagacgcatg tgttttggtt tgtgacaggc      900
agccagcatt tatatggcga agaggcggta caagaggtag aagagcattc caaaatgatc      960
tgcaacggat taaatgacgg agatttaagg tttcaagtcg agtacaaagc ggtggccact     1020
tcgctggacg gcgtcagaaa actgtttgaa gaggcgaacc gggacgatga gtgcgcaggc     1080
```

-continued

```
atcatcacct ggatgcatac gttttcaccg gccaaaatgt ggattcccgg cctttccgag      1140
ctgaataagc cgctgctcca ttttcatacc cagtttaacc gggacattcc gtgggataaa      1200
atcgacatgg atttcatgaa tattaatcag tctgcccacg gcgaccgcga atacggtttt      1260
atcggagcga gattgggcat tcctcgaaaa gtaatcgccg gatattggga agacagagaa      1320
gtaaagcgct cgatcgacaa atggatgagc gcagcggtcg catatattga aagccgccat      1380
atcaaagtcg cccgatttgg ggacaacatg cggaatgtgg cggtaacaga aggagataag      1440
attgaagcgc agattcagct tggctggtct gtcgacggat atggaatcgg cgatctcgtc      1500

<210> SEQ ID NO 39
<211> LENGTH: 32
<212> TYPE: DNA
<213> ORGANISM: Artificial Sequence
<220> FEATURE:
<223> OTHER INFORMATION: Primer

<400> SEQUENCE: 39
gactaagctt catccggcga tcagtttaat gc                                    32

<210> SEQ ID NO 40
<211> LENGTH: 65
<212> TYPE: DNA
<213> ORGANISM: Artificial Sequence
<220> FEATURE:
<223> OTHER INFORMATION: Primer

<400> SEQUENCE: 40
gactgaattc agatctgcgg ccgcacgcgt cgacagtact atttttttt gacagatttc       60 agaac                                                                  65

<210> SEQ ID NO 41
<211> LENGTH: 37
<212> TYPE: DNA
<213> ORGANISM: Artificial Sequence
<220> FEATURE:
<223> OTHER INFORMATION: Primer

<400> SEQUENCE: 41
gactggatcc agatctagtc gagtacaaag cggtggc                               37

<210> SEQ ID NO 42
<211> LENGTH: 31
<212> TYPE: DNA
<213> ORGANISM: Artificial Sequence
<220> FEATURE:
<223> OTHER INFORMATION: Primer

<400> SEQUENCE: 42
gactgaattc gaccagccaa gctgaatctg c                                     31

<210> SEQ ID NO 43
<211> LENGTH: 4078
<212> TYPE: DNA
<213> ORGANISM: Bacillus licheniformis

<400> SEQUENCE: 43
tttccggcgt agcacccgaa gcgaacctat taatcgtcaa ggtgctcggc ggtgaagacg       60
gcagcgggga ttatgaatgg atcatcaacg ggatcaacta cgccgttgag caaaaagccg      120
acattatttc aatgtcgctc ggcggtcctg ccgacgttcc ggagttgaag gaagcggtga      180
caaacgccgt gaagagcgga gtgctcgtcg tctgcgccgc aggaaacgaa ggcgacggca      240
```

-continued

```
atgaccgtac agaggagtac tcataccctg ctgcatacaa cgaagtcatc gccgtcggat    300
ccgtgtcatt gacgcgtgag tcttccgaat tttcaaatgc gaacaaagaa attgaccttg    360
ttgcacctgg agaagaaatc ctctctacat tgcccgacca tcaatacgga aagctgacgg    420
gaacatcgat ggctacaccg cacgtcagcg gcgcgctcgc tctcatcaag tcagctgaag    480
aagaggcgtt taaacggaaa ctgacagaac ccgaactgta tgctcagtta atccgccgca    540
cccttcctct tgattactca aaagcgctga tcggcaacgg attcttatat tgtcagcgc     600 cggaggtact ggcggaaaaa gccggcgaag caaaacttct ttccctttaa cagtctaaag    660
gaggctgccg acaatgtcgg cggccttttt catggccatg tataaagctg aatctttta    720 attgcaagaa ttcaaaaatt attttgacta aagatcgcg gcggtatata atctactaaa    780
caatttcatc gccgggaaca tggtaatcta acgaggttag attttaaaag ggaagtttgg    840
tgaaaatcca acgcggtccc gccactgtga atgaggaggt tatttcataa acccactgt    900 ttctatatgg aaggggaa ataaccgtcg attcatgagc caggagacct gcctgttctg     960
acgcaccata aacctacggt cgataggagg tgttcgagtt gacgtaacaa tcgctacgtt   1020
tatttctcgt tcgcaacatg ctgttttcag gcattcacct tctcattgtc cgaagtgtga   1080
gtgtcttttt ttattgaaca ctaaaaggag gagaccagac atgactaatg taaaaacgag   1140
cagcttgggc tttccaagaa tcggcttgaa cagagaatgg aaaaaatcgc ttgaggctta   1200
ttggaaagga acacggacc gcgagacctt tttgaaagaa atggatgaac aatttttagc    1260
agcgctccag actcagcttg atcagcaaat cgatatcata ccggtttccg actttacaat   1320
gtacgaccat gttcttgaca cggcggtgat gttcaactgg attccagatc gattcaagga   1380
tataaacgat ccgttagata cttatttcgc aatggcgaga ggcacgaaag atgctgtatc   1440
gagtgaaatg acaaaatggt ttaatacaaa ctaccattat attgtgcctg aatatgaaaa   1500
aggtgcacaa taccgcgtga cgagaaacaa accgcttcaa gattaccaaa gagcaaaagc   1560
agcattggga acagaaacga agcccgtcat actcggcctt tacactttcg tagcccttgc   1620
aaaaggctat gaacaacagg atattaaaga tatttataac caaatgacac ctctttacat   1680
ccaggttttg aaagagcttg agcaggaagg cgtcaaatgg gtgcaaattg acgagcctgc   1740
tcttgtgacg gcttcacctg aagaagcggc tgctgtcaaa gaaatctatc agacgattac   1800
agaagaagtc tctgaactga acatccttct gcaaacctac tttgactcgg ttgatgctta   1860
tgaagagctg atatcgtttc ctgtcgcagg aattggtctt gattttgttc atgataaagg   1920
gaaaaacttc gaacacctga agcgcacgg ttttcctaaa gacaaagtcc ttgccgccgg    1980
cattttagac ggacgcaaca tttggaaagc caatctcgaa gagcgcctcg acctgacgct   2040
tgaactgatc cagagagcgg gtgttgacga agtctggatt cagccttcaa acagcctgct   2100
tcatgtccct gtcgcaaaac acccgggcga acatcttgcc gacgatctct tgaacggttt   2160
atctttcgca aaagagaaac ttctggagct tacactgctg aagaacggac ttgtttccgg   2220
aaaagcggcc atccaagcgg aaatcgatga agcgcacgga caccttcaag atctcaaaca   2280
gtacggtgca gcgacaaatt cggcctttgc cgaagaaaga ggcaagctga ctgaggaaga   2340
ctttaaacgc ccgacagctt ttgaagaaag gctgcggatt caaatgact ctctcggact    2400 tcccctattg ccgacaacaa cgatcggcag cttcccgcag acggcggatg tgcggagcgc   2460
gcggcaaaaa tggcggaaaa agaatggtc cgacgagcag tatgaagcat ttattcagga   2520
agaaacaaag aaatggattg atattcagga agatctcgga cttgacgttc tcgttcacgg   2580
```

-continued

```
agaattcgaa cggacagaca tggttgagta tttcggcgaa aagctcggag gattcgcctt    2640
tactaaatac gcctgggttc agtcatacgg ttcccgctgc gtccggccgc cggtcatcta    2700
cggagatgtc gagtttaaag agccgatgac ggtaaaagaa acggtttacg cccaatcctt    2760
gacctcgaag aaagtcaagg gcatgctgac agggcctgtt accattttaa actggtcctt    2820
tgcccgctat gacctgccga gaaaagagat cgccttccaa atcgcctgcg ccctccgcaa    2880
agaggttgaa gcgcttgaaa aagcaggaat tcaaatcatt caggtcgatg aacctgcctt    2940
gagagaaggc ctgccgctta agaacgggga ttgggacgag tatctcaaat gggctgcaga    3000
agcgttcaga ctgtccactt catctgtgga agatacgacg caaatccata cgcatatgtg    3060
ctacagcaac tttgaagata tcgtagacgc gatcgaagat cttgacgcag acgtcattac    3120
gatcgagcac agcagaagcc acggcggatt tcttgattat ctggaacagc acccttacct    3180
gaaagggctt ggtcttggcg tatatgatat tcacagccct cgcgtcccct tccagcgatga   3240 aatgctcacg atcatagaag acgcgctgaa agtctgcccg gctgatcgct tctgggtaaa    3300
ccctgactgc ggtttaaaaa cgagacagcc agaggaaacg atcgcagcgc ttaagaatat    3360
ggttgaagca gccaaacaag caagaggcaa actggctcag actgtttaat tcacaaaaa    3420 atccactaca aacgccgcct gttcacacgg gcggctcttt tcatggctcc agccctttt    3480 aggccaaaag aaccgttata caaggtatgt ccgcccaaaa acattaaga cttttgattc    3540 attcgtacga tttccttccg tatccttttc ttttaacata tttgtagtag atgatggaag    3600
ggaaggaaaa tatgtagtga ttgacgatgg aatagcgtta gaacgaaaaa tcaagcgaaa    3660
aatatatcag gaagacattc actctcttca gctatacgta aaagatgtga atgccgccat    3720
tgatgagctg aggcaggaaa gttcttctat tttaaaagca caccaaacgt atatcaacgg    3780
atggcgcgga caggcgcgcg aaatgtatga cgcgcttttg gacgatctcg accgggcgga    3840
atcgcgcgtg tatgacaagc tgaggaccat taaagagcag gcggacgaag aaattgaacg    3900
gcttcagctg aaagccgagg agctgatatg acgatccggc tgaacatcaa tgatctgcac    3960
gccctcgccc gccaatttcg ttattcccac cagcgaatca gcgatttaat acgccttttg    4020
aaccgtcatt ttcatggttc ttttctccag cgtgaaaaca gcaaggaaca tgcggcat     4078
```

<210> SEQ ID NO 44
<211> LENGTH: 42
<212> TYPE: DNA
<213> ORGANISM: Artificial Sequence
<220> FEATURE:
<223> OTHER INFORMATION: Primer

<400> SEQUENCE: 44

```
aaaaaacccg agtttcacaa aaatccact acaaacgccg cc                       42
```

<210> SEQ ID NO 45
<211> LENGTH: 41
<212> TYPE: DNA
<213> ORGANISM: Artificial Sequence
<220> FEATURE:
<223> OTHER INFORMATION: Primer

<400> SEQUENCE: 45

```
ttttttttaa gcttatgccg catgttcctt gctgttttca c                        41
```

<210> SEQ ID NO 46
<211> LENGTH: 32
<212> TYPE: DNA
<213> ORGANISM: Artificial Sequence
<220> FEATURE:
<223> OTHER INFORMATION: Primer

<400> SEQUENCE: 46
aaaaaaatcg attcagggat ataaacgatc cg        32

<210> SEQ ID NO 47
<211> LENGTH: 45
<212> TYPE: DNA
<213> ORGANISM: Artificial Sequence
<220> FEATURE:
<223> OTHER INFORMATION: Primer

<400> SEQUENCE: 47
tttttttttt ccatcgcact gggatatcag ctcttcataa gcatc        45

<210> SEQ ID NO 48
<211> LENGTH: 3952
<212> TYPE: DNA
<213> ORGANISM: Artificial Sequence
<220> FEATURE:
<223> OTHER INFORMATION: Primer

<400> SEQUENCE: 48
tttatacgtt tccctctcgg caatcggagc ctacacgaca ccaagctacg agctgagcct        60
ggcgaataaa atggtgaagc tgtttatgct gatattggtg gcgcttttta aagtggaggg       120
atttgtcatc ggattaacga tcttaactat agtgatgact tcgatcaggt cattgcgaac       180
gccttactta tggcctctcc tcccgttcaa tggaaaagcg ttttggcatg ttctcgtgcg       240
cacgtccgtt ccaggggaaa agtcaggcc gagcatcgtt catccgagaa accgctccag        300
acagccgtga agccggcatt cgaagaggct ttccccggg gaaaagcctc tttttcaata        360
atcgaattcc ggtctttgag taccgatgcc tttgtattca ttggcagaga tcgcgactgc       420
ccggaggctg cagatgttgt tctgtcttct gatcggatag acgacataca gcatttcgcg       480
gccgtacggg tcaatcgttg acgaatgaag gaaaacctca gttcctctcc gccaaaatct       540
cgtattcgcc ggagctgtaa taatctgccc ttcataaggc tcataaattc tctgttcata       600
atgcgcagcc ggctgataag gggcgtatac atcttcaggt gcatagccgg gagcgggggt       660
gtagggataa cgatttggat acatatgata acctctttcc cacttcgttt tttggttttc       720
atctttaaga ttatattcag gtaaatgcct atttgtatgg gcgaaaatct cagcttttcg       780
gctcttttt tattgaatgg acgttgtgta tgcctatttc tatcaagcgc tgttttctgt       840
tattctataa tcaatagaat ggattagttg tttagggaat catttccttt ataaatcaag       900
aaaatttgga caaatggtgg tttagttttt aaaacgaaat gttataatac aacataagaa       960
tcgcactatc atgaagccgg aagatgcatc gggcagcaac cggagcgccc cttgcacctt      1020
tgtcgataga gaaagaggga atgacaattg tttttacacg gtactagcag acaaaatgaa      1080
agagggcacc tcgaaatcgg cggtgtcgat gttctatcat tggcagaaag atacggaaca      1140
cctctttatg tatacgatgt cgcgctgatt agagagcgcg cccgaaaatt ccagaaggca      1200
ttcaaggaag ccggtttaaa agcgcaggta gcgtatgcaa gcaaggcgtt ttcatcggtt      1260
gccatgattc agcttgccga acaagagggg ctgtctctgg atgtggtatc gggaggagag      1320
cttttcactg cgatcaaagc agggttccca gctgagcgga ttcattttca cggaaacaat      1380
aagagccctg aagaactagc catggcgctg agcatcaaa tcggctgcat cgtgctcgat      1440
aactttcacg agatcgccat tacagaagat ctttgcaagc gatcaggaca aactgtagac      1500

```
gttttgctca gaatcactcc gggagttgaa gcgcacacgc acgattatat tacgacgggg    1560
caggaagatt ccaaattcgg ttttgatctg cataatggac aggtcgaaca agccatcgaa    1620
caagtccgcc gctcgtctgc gtttaagctc ctcggcgtgc actgccacat cggttcgcaa    1680 attttttgata cggcaggatt tgtccttgca gcagacaaga ttttcgagaa gcttgcggaa    1740
tggcgggaga cttactcttt cattccgaaa gtgctcaatc ttggcggggg cttcggcatc    1800
cgctatacaa aagacgacga gccgcttgca gctgatgttt atgttgaaaa aatcatcgag    1860
gcggtcaaag caaatgccga gcatttcggc tttgacatcc ctgagatttg gatcgaacca    1920
ggccggtctc tcgtcggtga tgcggggact acgctgtaca cgatcggttc tcaaaaagag    1980
gtgccgggca ttcgcaaata tgtagccatc gacggcggca tgagcgataa tatcaggccg    2040
gcgctttatg aggcaaaata tgaagcagcc gtcgccaaca ggatgaacga tgcttgtcat    2100
gataccgcat caatcgcagg aaaatgctgc gaaagcggag atatgctgat ttgggatttg    2160
gaaatccccg aagttcgcga cggagatgtg ctcgccgttt tctgcaccgg tgcgtacggc    2220
tacagcatgg ccaacaacta caaccgcatt ccgcgcccgg ccgtcgtctt tgtcgaggac    2280
ggggaagcgc agctcgtcat tcagagagag acgtatgagg atatcgtcaa gctggatctg    2340
ccgctgaaat cgaaagtcaa acaataaaaa aatggagatt ccctaagagg ggggtctcca    2400
tttttaattc aagcacgaaa aacacttccc ggtgatcggg aggtgttttt tgttaaaaag    2460
atcatgacat gcatagaaca gcgaccgggc tagttgtata taatattgtg aatttaacaa    2520
aaaatttaca aaggagatga taaaggcaat gaccagggtg aaaaggatga gatttgctga    2580
tttgttggat ttagaggcgg agtagatgaa accggccaaa gtatccctac tccaccgatt    2640
gctccagtgc ctgaagcaat gtgttgattg taacacagta aatcgtttta cagcaataaa    2700 cattttgtg aatattttat tgattttggc tgtgatctca ttcccatatt ctgctgcggc    2760
ccatggcgca acacagtccg gcgatcaata ttcaagcttt gaagaattgg agcggaatga    2820
agatccagct tcttaccgaa ttacggagaa gaacgcaaga gtgccgatgc tcatcatggc    2880
catccatgga ggcggcatcg aacccggaac gagcgaaatc gccaatgaag tgtccaaaaa    2940
ctattccctg tacttgtttg aagggctgaa atcatcaggc aatacggacc ttcacattac    3000
aagcacgcgt tttgacgagc cagcggcgct cgcaattact gcaagccacc agtatgtcat    3060
gtcgctccac ggctattaca gtgaagaccg cgatattaaa gtaggcggca cagaccgcgc    3120
taaaatcaga atattggttg atgagctgaa ccgctcgggg tttgccgctg aaatgctggg    3180
gacagatgac aagtatgccg gaacccatcc gaataacatc gccaacaagt cgctttccgg    3240
gctgagcatt cagcttgaaa tgagcacggg ttttccgcaaa tctttattcg accggtttac    3300
actaaaagac agggcggcga cgcaaaacga aacgttttac cgatttacaa agctgctgac    3360
agattttatt catgaaaact atgaagaaga cggaggggat ttcccctctg caaaaataaa    3420 acacccccctt caagtgaaaa aaggaggtgt ttcggcggtt gtgttaaccg ttggactctg    3480
aggtgccgcc gccggtgaat acggaaacga tggcgttcca cagagacaca aagaagtcga    3540 tcagttttg aagaaagttt tgtccttctt cagaatccaa gaatttcgtg attttatcct    3600
ttgctttgtc aagctggtct ccaacctggt tccagtcgat attaatatt ttcatgttat    3660 taaataaaga tataagagag ttttctgat cttctgtgag tgtcacgcca agttcggaag    3720
cagccgaatc aatcgttttc tccaattcct cttttgactc gggaactccg tttttcgaga    3780
tttcttcctt gactttggcc atcagcgctg acgcgtttttc actgccgatt ttctcgccaa    3840
gctctgaagt ggtgacaagc tcttcattcg cgaccttttt cacatcttcg gaaattttttt    3900
```

-continued

```
cgcccgaagt cgtttcatac gctttcatca atccggttaa agcggctgtg cc        3952

<210> SEQ ID NO 49
<211> LENGTH: 6837
<212> TYPE: DNA
<213> ORGANISM: Artificial Sequence
<220> FEATURE:
<223> OTHER INFORMATION: Plasmid pMOL 1642
<220> FEATURE:
<221> NAME/KEY: misc_feature
<222> LOCATION: (669)..(669)
<223> OTHER INFORMATION: n denotes an undetermined nucleotide

<400> SEQUENCE: 49
gatcttcctt caggttatga ccatctgtgc cagttcgtaa tgtctggtca actttccgac    60
tctgagaaac ttctggaatc gctagagaat ttctggaatg ggattcagga gtggacagaa   120
cgacacggat atatagtgga tgtgtcaaaa cgcataccat tttgaacgat gacctctaat   180
aattgttaat catgttggag ctcagtgaga gcgaagcgaa cacttgattt tttaattttc   240
tatcttttat aggtcattag agtatactta tttgtcctat aaactattta gcagcataat   300
agatttattg aataggtcat ttaagttgag catattagag gaggaaaatc ttggagaaat   360
atttgaagaa cccgaggatc catgctgtcc agactgtccg ctgtgtaaaa ataggaata    420 aaggggggtt gttattattt tactgatatg taaaatataa tttgtataag aaaatgagag   480
ggagaggaaa catgaagaag attgcaattg cggcgattac agcgacaagc gtgctggctc   540
tcagcgcatg cagcggggga gattctgagg ttgttgcgga acaaaagct ggaaatatta   600 caaaagaaga cctttatcaa acattaaaag acaatgccgg agcggacgca ctgaacatgc   660
ttgttcagna aaagtactc gatgataaat acgatgtctc cgacaaagaa atcgacaaaa   720
agctgaacga gtacaaaaaa tcaatgggtg accagctcaa ccagctcatt gaccaaaag   780 gcgaagactt cgtcaagaa cagatcaat acgaacttct gatgcaaaaa gccgcaaagg   840
ataacataaa agtaaccgat gatgacgtaa agaatatta tgacggcctg aaaggcaaaa   900
tccacttaag ccacattctt gtgaaagaaa agaaaacggc tgaagaagtt gagaaaaagc   960
tgaaaaaagg cgaaaaattc gaagaccttg caaagagta ttcggtaccc gggtctagag  1020
tcgacgcggc cgcaaccatt tgatcaaagc ttgcatgcct gcaggtcgat tcacaaaaa   1080 taggcacacg aaaacaagt taagggatgc agtttatgca tcccttaact tacttattaa  1140
ataatttata gctattgaaa agagataaga attgttcaaa gctaatattg tttaaatcgt   1200
caattcctgc atgttttaag gaattgttaa attgatttt tgtaaatatt ttcttgtatt   1260
ctttgttaac ccattcata acgaaataat tatacttttg tttatctttg tgtgatattc    1320 ttgattttt tctacttaat ctgataagtg agctattcac tttaggttta ggatgaaaat  1380
attctcttgg aaccatactt aatatagaaa tatcaacttc tgccattaaa agtaatgcca  1440
atgagcgttt tgtatttaat aatcttttag caaacccgta ttccacgatt aaataaatct  1500
cattagctat actatcaaaa acaattttgc gtattatatc cgtacttatg ttataaggta  1560
tattaccata tattttatag gattggtttt taggaaattt aaactgcaat atatccttgt   1620 ttaaacttg gaattatcg tgatcaacaa gtttatttc tgtagttttg cataatttat   1680
ggtctatttc aatggcagtt acgaaattac acctctttac taattcaagg gtaaaatggc   1740
cttttcctga gccgatttca agatattat catgttcatt taatcтттata tttgtcatta  1800

tttatcttat attatgtttt gaagtaataa agttttgact gtgttttata tttttctcgt  1860
```

-continued

```
tcattataac cctctttaat ttggttatat gaattttgct tattaacgat tcattataac    1920
cacttatttt ttgtttggtt gataatgaac tgtgctgatt acaaaaatac taaaaatgcc    1980
catatttttt cctccttata aaattagtat aattatagca cgagctctga taaatatgaa    2040
catgatgagt gatcgttaaa tttatactgc aatcggatgc gattattgaa taaaagatat    2100
gagagattta tctaatttct tttttcttgt aaaaaaagaa agttcttaaa ggttttatag    2160
ttttggtcgt agagcacacg gtttaacgac ttaattacga agtaaataag tctagtgtgt    2220
tagactttat gaaatctata tacgtttata tatatttatt atccggaggt gtagcatgtc    2280
tcattcaatt ttgagggttg ccagagttaa aggatcaagt aatacaaacg ggatacaaag    2340
acataatcaa agagagaata aaaactataa taataaagac ataaatcatg aggaaacata    2400
taaaaattat gatttgatta acgcacaaaa tataaagtat aaagataaaa ttgatgaaac    2460
gattgatgag aattattcag ggaaacgtaa aattcggtca gatgcaattc gacatgtgga    2520
cggactggtt acaagtgata aagatttctt tgatgattta agcggagaag aaatagaacg    2580
attttttaaa gatagcttgg agtttctaga aaatgaatac ggtaaggaaa atatgctgta    2640
tgcgactgtc catctggatg aaagagtccc acatatgcac tttggttttg tccctttaac    2700
agaggacggg agattgtctg caaaagaaca gttaggcaac aagaaagact ttactcaatt    2760
acaagataga tttaatgagt atgtgaatga aaaggttat gaacttgaaa gaggcacgtc    2820
caaagaggtt acagaacgag aacataaagc gatggatcag tacaagaaag atactgtatt    2880
tcataaacag gaactgcaag aagttaagga tgagttacag aaggcaaata agcagttaca    2940
gagtggaata gagcatatga ggtctacgaa acccttttgat tatgaaaatg agcgtacagg    3000
tttgttctct ggacgtgaag agactggtag aaagatatta actgctgatg aatttgaacg    3060
cctgcaagaa acaatctctt ctgcagaacg gattgttgat gattacgaaa atattaagag    3120
cacagactat tacacagaaa atcaagaatt aaaaaaacgt agagagagtt tgaaagaagt    3180
agtgaataca tggaaagagg ggtatcacga aaaaagtaaa gaggttaata aattaaagcg    3240
agagaatgat agtttgaatg agcagttgaa tgtatcagag aaatttcaag ctagtacagt    3300
gactttatat cgtgctgcga gggcgaattt ccctgggttt gagaaagggt ttaataggct    3360
taaagagaaa ttcttaatg attccaaatt tgagcgtgtg ggacagttta tggatgttgt    3420
acaggataat gtccagaagg tcgatagaaa gcgtgagaaa cagcgtacag acgatttaga    3480
gatgtagagg tactttatg ccgagaaaac ttttgcgtg tgacagtcct taaaatatac    3540
ttagagcgta agcgaaagta gtagcgacag ctattaactt tcggtttcaa agctctagga    3600
tttttaatgg acgcagcgca tcacacgcaa aaaggaaatt ggaataaatg cgaaatttga    3660
gatgttaatt aaagaccttt ttgaggtctt tttttcttag attttttgggg ttatttaggg    3720 gagaaaacat aggggggtac tacgacctcc cccctaggtg tccattgtcc attgtccaaa    3780 caaataaaata aatattgggt ttttaatgtt aaaaggttgt tttttatgtt aaagtgaaaa    3840
aaacagatgt tgggaggtac agtgatggtt gtagatagaa agaagagaa aaagttgct    3900 gttactttaa gacttacaac agaagaaaat gagatattaa atagaatcaa agaaaaatat    3960
aatattagca aatcagatgc aaccggtatt ctaataaaaa aatatgcaaa ggaggaatac    4020
ggtgcatttt aaacaaaaaa agatagacag cactggcatg ctgcctatct atgactaaat    4080
tttgttaagt gtattagcac cgttattata tcatgagcga aaatgtaata aagaaactg    4140 aaaacaagaa aaattcaaga ggacgtaatt ggacatttgt tttatatcca gaatcagcaa    4200
aagccgagtg gttagagtat ttaaaagagt tacacattca atttgtagtg tctccattac    4260
```

```
atgataggga tactgataca gaaggtagga tgaaaaaaga gcattatcat attctagtga    4320
tgtatgaggg taataaatct tatgaacaga taaaaataat tacagaagaa ttgaatgcga    4380
ctattccgca gattgcagga agtgtgaaag gtcttgtgag atatatgctt cacatggacg    4440
atcctaataa atttaaatat caaaaagaag atatgatagt ttatggcggt gtagatgttg    4500
atgaattatt aaagaaaaca acaacagata gatataaatt aattaaagaa atgattgagt    4560
ttattgatga acaaggaatc gtagaattta agagtttaat ggattatgca atgaagttta    4620
aatttgatga ttggttcccg cttttatgtg ataactcggc gtatgttatt caagaatata    4680
taaaatcaaa tcggtataaa tctgaccgat agattttgaa tttaggtgtc acaagacact    4740
cttttttcgc accagcgaaa actggtttaa gccgactgcg caaaagacat aatcgactct    4800
agaggatcct tttagtccag ctgatttcac tttttgcatt ctacaaactg cataactcat    4860
atgtaaatcg ctccttttta ggtggcacaa atgtgaggca ttttcgctct ttccggcaac    4920
cacttccaag taaagtataa cacactatac tttatattca taaagtgtgt gctctgcgag    4980
gctgtcggca gtgccgacca aaaccataaa acctttaaga cctttctttt ttttacgaga    5040
aaaaagaaac aaaaaaacct gccctctgcc acctcagcaa aggggggttt tgctctcgtg    5100
ctcgtttaaa aatcagcaag ggacaggtag tattttttga agatcact caaaaaatct    5160
ccacctttaa acccttgcca attttttattt tgtccgtttt gtctagctta ccgaaagcca    5220
gactcagcaa gaataaaatt tttattgtct ttcggttttc tagtgtaacg gacaaaacca    5280
ctcaaaataa aaagataca agagaggtct ctcgtatctt ttattcagca atcgcgcccg    5340
attgctgaac agattaataa tgagccgcgg atatcgatgc cttgtcagag agattcctga    5400
agagcggcag gataaggtat ttagaatgat taatgtgctg atcttaattt tattgatctc    5460
atcattcatt gagatttcct ttacggtgta aagaaaaagg atagctgccg atcgtattga    5520
tccggcagct atccttttgt ttattagcat atccaagaag caccaataat aattaataag    5580
atgaacagca ccacaagcag cgcaaagccg ccagcgaaac ctcctgcata accgtcgccc    5640
atattgacac ctcctctgcc ccagtcgtta cattagtgta tgcacgaatg tcatgaaacg    5700
attaggctat cgtccaaaag aaaagaaccg cctgaaaaaa tgacggttct tttctcattt    5760
tctaaggttt tagtacagat aagctgcacc aacgatgatt aataaaatga acaacacgac    5820
caataaagca aaaccgcttg agtatcctcc gctcatgtta ttgacctcga attctgatca    5880
aatggttcag tgagagcgaa gcgaacactt gattttttaa ttttctatct tttataggtc    5940
attagagtat acttatttgt cctataaact atttagcagc ataatagatt tattgaatag    6000
gtcatttaag ttgagcatat tagaggagga aaatcttgga gaaatatttg aagaacccga    6060
acgcgtgagt agttcaacaa acgggccagt ttgttgaaga ttagatgcta taattgttat    6120
taaaaggatt gaaggatgct taggaagacg agttattaat agctgaataa gaacggtgct    6180
ctccaaatat tcttatttag aaaagcaaat ctaaaattat ctgaaagggg aatgagaata    6240
gtgaatggac caataataat gactagagaa gaaagaatga agattgttca tgaaattaag    6300
gaacgaatat tggataaata tggggatgat gttaaggcta ttggtgttta tggctctctt    6360
ggtcgtcaga ctgatgggcc ctattcggat attgagatga tgtgtgtcat gtcaacagag    6420
gaagcagagt tcagccatga atggacaacc ggtgagtgga aggtggaagt gaattttgat    6480
agcgaagaga ttctactaga ttatgcatct caggtggaat cagattggcc gcttacacat    6540
ggtcaatttt tctctatttt gccgattta gattcaggtg gatacttaga gaaagtgtat    6600
```

-continued

```
caaactgcta aatcggtaga agcccaaacg ttccacgatg cgatttgtgc ccttatcgta      6660
gaagagctgt ttgaatatgc aggcaaatgg cgtaatattc gtgtgcaagg accgacaaca      6720
tttctaccat ccttgactgt acaggtagca atggcaggtg ccatgttgat tggtctgcat      6780
catcgcatct gttatacgac gagcgcttcg gtcttaactg aagcagttaa gcaatca        6837
```

<210> SEQ ID NO 50
<211> LENGTH: 817
<212> TYPE: DNA
<213> ORGANISM: Artificial Sequence
<220> FEATURE:
<223> OTHER INFORMATION: Primer

<400> SEQUENCE: 50

```
gaattccggc ccaacgatgg ctgatttccg ggttgacggc cggcggaacc aagggtgat       60 cggtcggcgg aaatgaaggc ctgcggcgag tgcgggcctt ctgttttgag gattataatc     120
agagtatatt gaaagtttcg cgatcttttc gtataattgt tttaggcata gtgcaatcga     180
taagcttgaa ttcggaggcc gttattatat catgagcgaa aatgtaataa aagaaactga     240
aaacaagaaa aattcaagag gacgtaattg gacatttgtt ttatatccag aatcagcaaa     300
agccgagtgg ttagagtatt taaaagagtt acacattcaa tttgtagtgt ctccattaca     360
tgatagggat actgatacag aaggtaggat gaaaaaagag cattatcata ttctagtgat     420
gtatgagggt aataaatctt atgaacagat aaaaataatt acagaagaat tgaatgcgac     480
tattccgcag attgcaggaa gtgtgaaagg tcttgtgaga tatatgcttc acatggacga     540
tcctaataaa tttaaatatc aaaaagaaga tatgatagtt tatggcggtg tagatgttga     600
tgaattatta aagaaaacaa caacagatag atataaatta attaaagaaa tgattgagtt     660
tattgatgaa caaggaatcg tagaatttaa gagtttaatg gattatgcaa tgaagtttaa     720
atttgatgat tggttcccgc ttttatgtga taactcggcg tatgttattc aagaatatat     780
aaaatcaaat cggtataaat ctgaccgata gggatcc                              817
```